US012788759B2

(12) United States Patent
Gillis et al.

(10) Patent No.: US 12,788,759 B2
(45) Date of Patent: Nov. 10, 2026

(54) INHIBITORS OF HUMAN IMMUNODEFICIENCY VIRUS REPLICATION

(71) Applicant: VIIV HEALTHCARE UK (NO.5) LIMITED, Middlesex (GB)

(72) Inventors: Eric P. Gillis, Branford, CT (US); Christiana Iwuagwu, Wallingford, CT (US)

(73) Assignee: VIIV HEALTHCARE UK (No. 5) LIMITED, Stevenage (GB)

( * ) Notice: Subject to any disclaimer, the term of this patent is extended or adjusted under 35 U.S.C. 154(b) by 742 days.

(21) Appl. No.: 17/802,194

(22) PCT Filed: Mar. 3, 2021

(86) PCT No.: PCT/IB2021/051764
§ 371 (c)(1),
(2) Date: Aug. 25, 2022

(87) PCT Pub. No.: WO2021/176366
PCT Pub. Date: Sep. 10, 2021

(65) Prior Publication Data
US 2023/0355626 A1 Nov. 9, 2023

Related U.S. Application Data
(60) Provisional application No. 63/040,051, filed on Jun. 17, 2020, provisional application No. 62/985,937, filed on Mar. 6, 2020.

(51) Int. Cl.

| | |
|---|---|
| ***A61K 31/519*** | (2006.01) |
| ***A61K 31/4985*** | (2006.01) |
| ***A61K 31/513*** | (2006.01) |
| ***A61K 31/5365*** | (2006.01) |
| ***A61K 31/537*** | (2006.01) |
| ***A61K 31/54*** | (2006.01) |
| ***A61K 31/675*** | (2006.01) |
| ***A61K 45/06*** | (2006.01) |
| ***A61P 31/18*** | (2006.01) |
| ***C07D 471/04*** | (2006.01) |

(52) U.S. Cl.
CPC ........ *A61K 31/519* (2013.01); *A61K 31/4985* (2013.01); *A61K 31/513* (2013.01); *A61K 31/5365* (2013.01); *A61K 31/537* (2013.01); *A61K 31/54* (2013.01); *A61K 31/675* (2013.01); *A61K 45/06* (2013.01); *A61P 31/18* (2018.01); *C07D 471/04* (2013.01)

(58) Field of Classification Search
CPC ...... C07D 471/04; A61K 31/519; A61P 31/18
See application file for complete search history.

(56) References Cited

U.S. PATENT DOCUMENTS

| | | | | |
|---|---|---|---|---|
| 9,050,344 | B2 | 6/2015 | Brizgys et al. | |
| 10,954,252 | B1 * | 3/2021 | Babu .................... | C07D 487/04 |
| 11,541,055 | B2 | 1/2023 | Gillis et al. | |
| 11,919,897 | B2 * | 3/2024 | Iwuagwu ............. | C07D 471/04 |
| 12,129,255 | B2 * | 10/2024 | Gillis ..................... | A61K 45/06 |
| 2003/0069266 | A1 | 4/2003 | Wang et al. | |
| 2005/0256109 | A1 | 11/2005 | Naidu | |
| 2018/0086755 | A1 | 3/2018 | Chin et al. | |
| 2022/0105096 | A1 | 4/2022 | Iwuagwu | |

(Continued)

FOREIGN PATENT DOCUMENTS

| | | |
|---|---|---|
| AU | 2021256166 B2 | 5/2024 |
| CO | 2021004679 A2 | 4/2021 |

(Continued)

OTHER PUBLICATIONS

Patani et al., "Bioisosterism: A Rational Approach in Drug Design", 1996, Chem Rev, 96, pp. 3147-3176 (Year: 1996).*

(Continued)

*Primary Examiner* — Brenda L Coleman
*Assistant Examiner* — Madeline E Braun
(74) *Attorney, Agent, or Firm* — Eric Myers

(57) ABSTRACT

Compounds of Formula I, including pharmaceutically acceptable salts thereof, are set forth:

Formula I

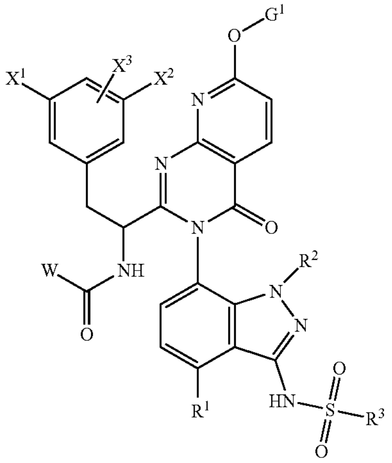

Compositions that contain a compound of Formula I or a pharmaceutically acceptable salt thereof are further set forth. In addition, methods for treating human immunodeficiency virus (HIV) infection with a compound of Formula I or a pharmaceutically acceptable salt thereof are set forth.

32 Claims, No Drawings

(56) References Cited

U.S. PATENT DOCUMENTS

| | | | |
|---|---|---|---|
| 2023/0106880 A1 | 4/2023 | Gillis et al. | |
| 2023/0149408 A1 | 5/2023 | Parcella et al. | |
| 2024/0374598 A1 | 11/2024 | Bowsher et al. | |
| 2025/0019383 A1 | 1/2025 | Gillis et al. | |

FOREIGN PATENT DOCUMENTS

| | | | | |
|---|---|---|---|---|
| EA | 007184 B1 | 8/2006 | | |
| JP | 2004536796 A | 12/2004 | | |
| JP | 2014522852 A | 9/2014 | | |
| JP | 2016504392 A | 2/2016 | | |
| JP | 2017525722 A | 9/2017 | | |
| JP | 2022523726 A | 4/2022 | | |
| JP | 7301000 B2 | 6/2023 | | |
| JP | 7398448 B2 | 12/2023 | | |
| JP | 7628512 B2 | 2/2025 | | |
| MX | 2021016149 A | 5/2022 | | |
| RU | 2325389 C2 | 5/2008 | | |
| UY | 37710 A | 11/2018 | | |
| UY | 38559 A | 7/2020 | | |
| WO | WO-1993003022 A1 | 2/1993 | | |
| WO | WO-2001029037 A2 | 4/2001 | | |
| WO | WO-2004014380 A1 | 2/2004 | | |
| WO | WO-2004052890 A1 | 6/2004 | | |
| WO | WO-2004058756 A1 | 7/2004 | | |
| WO | WO-2007039218 A1 | 4/2007 | | |
| WO | WO-2010000032 A1 | 1/2010 | | |
| WO | WO-2010017355 A2 | 2/2010 | | |
| WO | WO-2011060395 A1 | 5/2011 | | |
| WO | WO-2012065062 A1 | 5/2012 | | |
| WO | WO-2013006738 A1 | 1/2013 | | |
| WO | WO-2014110297 A1 | 7/2014 | | |
| WO | WO-2014120808 A1 | 8/2014 | | |
| WO | WO-2014134566 A2 | 9/2014 | | |
| WO | WO-2016003343 A1 | 1/2016 | | |
| WO | WO-2016033243 A1 | 3/2016 | | |
| WO | WO-2017066227 A1 | 4/2017 | | |
| WO | WO-2018035359 A1 | 2/2018 | | |
| WO | WO 2018/203235 A1 | 11/2018 | | |
| WO | WO 2019/198024 A1 | 10/2019 | | |
| WO | WO-2020018459 A1 | 1/2020 | | |
| WO | WO-2020031112 A1 | 2/2020 | | |
| WO | WO 2020/058844 A1 | 3/2020 | | |
| WO | WO-2020053811 A1 | 3/2020 | | |
| WO | WO-2020068729 A1 | 4/2020 | | |
| WO | WO-2020084492 A1 | 4/2020 | | |
| WO | WO 2020/089778 A1 | 5/2020 | | |
| WO | WO 2020/095176 A1 | 5/2020 | | |
| WO | WO 2020/095177 A1 | 5/2020 | | |
| WO | WO 2020/157692 A1 | 8/2020 | | |
| WO | WO 2020/254985 A1 | 12/2020 | | |
| WO | WO-2021116872 A1 * | 6/2021 | .......... | A61K 31/047 |

OTHER PUBLICATIONS

Mcarthur, et al., *Diseases*, HIV Capsid Inhibitors Beyond PF74, 7(4):1-10 (2019).

Bassetto M., et al., "Polyfluorinated Groups in Medicinal Chemistry," Future Medicinal Chemistry, 2015, vol. 7(4), pp. 527-546.

Bastin R.J., et al., "Salt Selection and Optimisation Procedures for Pharmaceutical New Chemical Entities," Organic Process Research & Development, 2000, vol. 4, pp. 427-435, doi:10.1021/op000018u, XP002228592.

Belikov V.G., "Main stages of the search for medicinal substance," General Pharmaceutical Chemistry, Textbook, Ed, 4th Edition. Moscow: MEDpress—Inform, 2007, 4 Pages, (pp. 27, 23, 29).

Belikov V.G., "Pharmaceutical Chemistry," Textbook, Moscow: "MEDpress-Inform", 2007, pp. 27-29 (6 Pages).

Chou T-C., "Drug Combination Studies and Their Synergy Quantification Using the Chou-Talalay Method," Cancer Research, Jan. 15, 2010, vol. 70, No. 2, pp. 440-446.

Das K., et al., "Roles of conformational and positional adaptability in structure-based design of TMC125-R165335 (etravirine) and related non-nucleoside reverse transcriptase inhibitors that are highly potent and effective against wild-type and drug-resistant HIV-1 variants." J Med Chem. May 6, 2004;47(10):2550-60.

Gavrilov A.S., "Technology of dosage forms as a science," Pharmaceutical Technology, Textbook, Moscow: GEOTAR-Media Publishing Group, 2010, 2 Pages, pp. 20.

Gillis E.P., et al., "Applications of Fluorine in Medicinal Chemistry," Journal of Medicinal Chemistry, 2015, vol. 58, No. 21, pp. 8315-8359, XP093035727.

Glunz P.W., "Recent Encounters with Atropisomerism in Drug Discovery," Bioorganic & Medicinal Chemistry Letters, Elsevier, Amsterdam, NL, 2018, vol. 28, No. 2, pp. 53-60, DOI: 10.1016/j.bmcl.2017.11.050, ISSN: 0960-894X, XP085314564, Received on Oct. 16, 2017, Available Online Dec. 6, 2017.

Gullapall R., et al., "Polyethylene Glycols in Oral and Parenteral Formulations—a Critical Review," International Journal of Pharmaceutics, 2015, vol. 496, pp. 219-239.

Hagmann W. K., "The Many Roles for Fluorine in Medicinal Chemistry," Journal of Medicinal Chemistry, 2008, vol. 51, pp. 4359-4369.

International Preliminary Report on Patentability for International Application No. PCT/IB2019/059450, mailed May 20, 2021, 8 Pages.

International Preliminary Report on Patentability for International Application No. PCT/IB2020/055653, mailed Dec. 30, 2021, 7 Pages.

International Preliminary Report on Patentability for International Application No. PCT/IB2021/051764, mailed Sep. 15, 2022, 11 Pages.

International Preliminary Report on Patentability for International Application No. PCT/IB2021/051765, mailed Sep. 15, 2022, 7 Pages.

International Search Report and Written Opinion for International Application No. PCT/IB2019/059450, mailed Jan. 30, 2020, 9 Pages.

International Search Report and Written Opinion for International Application No. PCT/IB2020/055653, mailed Sep. 10, 2020, 8 Pages.

International Search Report and Written Opinion for International Application No. PCT/IB2021/051764, mailed May 12, 2021, 13 Pages.

International Search Report and Written Opinion for International Application No. PCT/IB2021/051765 mailed Apr. 15, 2021, 8 Pages.

International Search Report and Written Opinion for International Application No. PCT/IB2021/053046, mailed Jul. 1, 2021, 8 Pages.

Kharkevich D.A., "Pharmacology," 10th ed. M .: GEOTAR-Media, 2010, pp. 72-82 (14 Pages).

Kholodov L.E., et al., "Clinical Pharmacokinetics," Medicine, 1985, pp. 83-98, 134-138, 160, 378-380.

Krasnyuk I.I., et al., "Pharmaceutical Technology: Technology of Dosage Forms," A Txtbook for Students of Higher Education Institutions, 2006, 2nd edition, Academy Publishing Center, pp. 6(6 Pages).

Kummerer K., et al., "Pharmaceuticals in the Environment," Department of Environmental Health Sciences, University Medical Center Freiburg, 79106 Freiburg, Germany, Annual Review of Environment and Resources, 2010, vol. 35, pp. 57-75 (22 Pages).

Kummerer K., "Pharmaceuticals in the environment," Annual Review of Environment and Resources, 2010, vol. 35, pp. 57-75, Retrieved from [doi: 10.1146/annurev-environ-052809-161223].

Laplante S.R., et al., "Assessing Atropisomer Axial Chirality in Drug Discovery and Development," Journal of Medicinal Chemistry, 2011, vol. 54, No. 20, pp. 7005-7022.

Laplante S.R., et al., "Revealing Atropisomer Axial Chirality in Drug Discovery," ChemMedChem, 2011, vol. 6, No. 3, pp. 505-513, XP072417599.

Mashkovskiy M.D., Manual for doctors, Medicinal means, 14th edition, vol. 1, Moscow, 2001, pp. 11(4 Pages).

Mashkovsky M.D., et al., "Pharmacology," Textbook, 2010, 10th Edition, pp. 72-82, Drugs, 14th Edition, vol. 1, Moscow, 2001, p. 11, 2 Pages.

(56) References Cited

OTHER PUBLICATIONS

Mironov A.N., "Guideline for Preclinical Studies of Medicinal Products," Part One, Moscow, Griff & K, 2012, pp. 525-548, 944 p.
Purser S., et al., "Fluorine in Medicinal Chemistry," Chemical Society Reviews, 2008, vol. 37(2), pp. 320-330.
Sergeev M., "Short Course in Molecular Pharmacology," A Concise Course in Molecular Biology, 1975, 8 Pages.
Swallow S., "Fluorine in Medicinal Chemistry," Chapter Two, Progress in Medicinal Chemistry, Elsevier, 2015, vol. 54, pp. 65-133, Edited by G. Lawton, D.R. Witty, pp. 97-165 (p. 98-103, 115-120, 124-126, 129-130, 140-141, 157-158), DOI: 10.1016/bs.pmch.2014.11.001, ISBN: 9780444634801.
Tentsova A.I., et al., "Modern Biopharmaceutical Aspects of Excipients," Pharmacy, 2012, vol. 7, pp. 3-4 (4Pages).
Third Party Observation and Written Opinion for Singapore Application No. 11202113548Q, mailed Dec. 19, 2022, 5 Pages.
Third Party Observation for International Application No. PCT/IB2020/055653, dated Oct. 19, 2021, 6 Pages.
Third Party Observation for International Application No. PCT/IB2021/051764, dated Jul. 6, 2022, 08 Pages.
Third Party Observations from Corresponding EP Application No. 21711369.51110, mailed Sep. 16, 2022, 7 Pages.
Tikhonov A.I., "Technology Medicines," A Textbook for Pharmaceutical Higher Education Institutions and Departments, Kh.: NFAU publishers Golden pages, 2002, pp. 45-46(6Pages).
Zhulenko V., et al., "Pharmacology," KolosS, 2008, pp. 34-35.
Zuo X., et al., "Current Insights into Anti-HIV Drug Discovery and Development: a Review of Recent Patent Literature (2014-2017)," Expert Opinion on Therapeutic Patents, 2018, vol. 28(4), pp. 299-316, Retrieved from [DOI: 10.1080/13543776.2018.1438410].
Strickley R G., "Solubilizing Excipients in Oral and Injectable Formulations," Pharmaceutical Research, Springer, New York, US, Feb. 1, 2004, vol. 21, No. 2, pp. 201-230, XP009035738.
Third Party Observation for International Application No. PCT/IB2021/053046, dated Aug. 15, 2022, 13 Pages.
Meanwell N.A., "Fluorine and Fluorinated Motifs in the Design and Application of Bioisosteres for Drug Design," Journal of Medicinal Chemistry, 2018, vol. 61(14), pp. 5822-5880, Retrieved from [ DOI: 10.1021/acs.jmedchem.7b01788].
Beyrer C., et al., "HIV Drug Resistance—An Emerging Threat to Epidemic Control," New England Journal of Medicine, Oct. 26, 2017, vol. 377(17), pp. 1605-1607, XP055649066, Retrieved from [Doi: 10.1056/NEJMp1710608.].
Gupta R.K., et al., "HIV-1 Drug Resistance Before Initiation or Re-initiation of First-line Antiretroviral Therapy in Low-income and Middle-income Countries: a Systematic Review and Meta-regression Analysis," Lancet Infectious Diseases, Mar. 2018, vol. 18(3), pp. 346-355, XP055649070, Retrieved from [Doi: 10.1016/S1473-3099(17)30702-8].
Zazzi M., et al., "The Global Burden of HIV-1 Drug Resistance in the past 20 Years," PeerJ, May 2018, vol. 26(5), pp. 1-16, Retrieved from [Doi: 10.7717/peerj.4848].

* cited by examiner

INHIBITORS OF HUMAN IMMUNODEFICIENCY VIRUS REPLICATION

CROSS REFERENCE TO RELATED APPLICATIONS

This application is a § 371 national phase entry of International Application No. PCT/IB2021/051764, filed 3 Mar. 2021, which claims the benefit of U.S. Provisional Application No. 62/985,937, filed 6 Mar. 2020, and U.S. Provisional Application No. 63/040,051, filed 17 Jun. 2020.

FIELD OF THE INVENTION

The invention relates to compounds, compositions, and methods for the treatment of human immunodeficiency virus (HIV) infection. More particularly, the invention provides novel inhibitors of HIV, pharmaceutical compositions containing such compounds, and methods for using these compounds in the treatment of HIV infection. The invention also relates to methods for making the compounds hereinafter described.

BACKGROUND OF THE INVENTION

Acquired immunodeficiency syndrome (AIDS) is the result of infection by HIV. HIV continues to be a major global public health issue. In 2015, an estimated 36.7 million people were living with HIV (including 1.8 million children)—a global HIV prevalence of 0.8%. The vast majority of this number live in low- and middle-income countries. In the same year, 1.1 million people died of AIDS-related illnesses.

Current therapy for HIV-infected individuals consists of a combination of approved anti-retroviral agents. Close to four dozen drugs are currently approved for HIV infection, either as single agents, fixed dose combinations or single tablet regimens; the latter two containing 2-4 approved agents. These agents belong to a number of different classes, targeting either a viral enzyme or the function of a viral protein during the virus replication cycle. Thus, agents are classified as either nucleotide reverse transcriptase inhibitors (NRTIs), non-nucleotide reverse transcriptase inhibitors (NNRTIs), protease inhibitors (PIs), integrase strand transfer inhibitors (INSTIs), or entry inhibitors (one, maraviroc, targets the host CCR5 protein, while the other, enfuvirtide, is a peptide that targets the gp41 region of the viral gp160 protein). In addition, a pharmacokinetic enhancer (cobicistat or ritonavir) can be used in combinations with antiretroviral agents (ARVs) that require boosting.

Despite the armamentarium of agents and drug combinations, there remains a medical need for new anti-retroviral agents. High viral heterogeneity, drug-associated toxicity, tolerability problems, and poor adherence can all lead to treatment failure and may result in the selection of viruses with mutations that confer resistance to one or more anti-retroviral agents or even multiple drugs from an entire class (Beyrer, C., Pozniak A. HIV drug resistance—an emerging threat to epidemic control. N. Engl. J. Med. 2017, 377, 1605-1607; Gupta, R. K., Gregson J., et al. HIV-1 drug resistance before initiation or re-initiation of first-line anti-retroviral therapy in low-income and middle-income countries: a systematic review and meta-regression analysis. Lancet Infect. Dis. 2017, 18, 346-355; Zazzi, M., Hu, H., Prosperi, M. The global burden of HIV-1 drug resistance in the past 20 years. PeerJ. 2018, DOI 10.7717/peerj.4848). As a result, new drugs are needed that are easier to take, have high genetic barriers to the development of resistance, and have improved safety over current agents. In this panoply of choices, novel mechanisms of action (MOAs) that can be used as part of the preferred antiretroviral therapy (ART) can still have a major role to play since they should be effective against viruses resistant to current agents. The improvements that would make drugs easier to take for long periods of time or even for a lifetime could include all or some of the following: reduced side effects, reduced drug-drug interactions, increased duration between dosing, or alternate routes of administration which match to individual patient preferences. The goals of improved safety would definitely include high therapeutic indices towards any toxicities that would cause discontinuation of dosing, and could also include reduced side-effects or reduced drug-drug interactions. The potential to use fewer overall drugs in a combination regimen would also likely lead to improved compliance and safety. Increased potency against the antiviral target, especially if maintained in the presence of human plasma and serum albumin, would also lead to a reduced dose and could directly and positively affect the duration of dosing and the therapeutic index over side effects and toxicities. To summarize, maximum benefits to HIV infected patients would be achieved if anti-HIV drugs with new mechanisms of action were discovered which also have the other benefits described above which facilitate long term compliance and safety.

Certain potentially therapeutic compounds which appear to act by disrupting the normal functions of the HIV virus capsid have been described in the art. No currently approved drugs act by this mechanism and thus a compound acting through this mechanism would be a useful addition to the options available for the treatment of HIV infection. Compounds which appear to target the HIV capsid have been the subject of recent reviews which describe much of the most important work to date. These reviews include the following: "HIV-1 Capsid Inhibitors as Antiretroviral Agents" Thenin-Houssier, Suzie; Valente, Susana T. Current HIV Research, 2016, 14, 270; "Inhibitors of the HIV-1 capsid, a target of opportunity" Carnes, Stephanie K.; Sheehan, Jonathan H.; Aiken, Christopher, *Current Opinion in HIV& AIDS*2018, 13, 359-365; "HIV Capsid Inhibitors Beyond PF74" McArthur, Carole, Diseases, 2019, 7, 22; and "Insights into HIV-1 capsid inhibitors in preclinical and early clinical development as antiretroviral agents" Cevik, Muge; Orkin, Chloe *Expert Opin Inv. Drugs,* 2019, 28, 1021; Relevant patent applications are: WO2012065062, WO2013006738, WO 2013006792, WO2014110296, WO2014110297, WO2014110298, WO2014134566, WO2015061518, WO2015130964, WO2015130966, WO2016040084, WO2016033243, WO2016172424, WO2016172425, WO2018035359, WO2018203235, WO2019035904, WO2019035973, WO2019161017, WO2019161280 and WO2019198024.

What is now needed in the art are additional compounds which are novel and useful in the treatment of HIV. Additionally, these compounds should provide advantages for pharmaceutical uses, for example, with regard to one or more of their mechanisms of action, binding, inhibition efficacy, target selectivity, solubility, safety profiles, bioavailability and/or reduced frequency of dosing. Also needed are new formulations and methods of treatment which utilize these compounds.

SUMMARY OF THE INVENTION

Briefly, in one aspect, the present invention discloses a compound of Formula I, or a pharmaceutically acceptable salt thereof:

Formula I

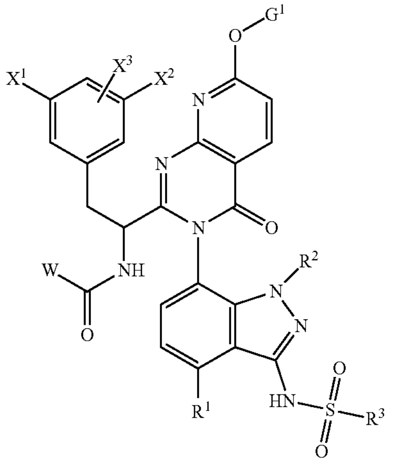

wherein:

$X^1$ and $X^2$ are independently selected from H, F, Cl, or —$CH_3$ and $X^3$ is H, F, Cl, —$CH_3$, —$OCH_3$, —$OCHF_2$, or —$OCF_3$ with the proviso that within the group $X^1$, $X^2$, and $X^3$ the substituent Cl is not used more than twice and the substituent —$CH_3$ is not used more than twice;

$R^1$ is hydrogen, Cl, F, or $CH_3$;

$R^2$ is hydrogen, $C_1$-$C_3$alkyl optionally substituted with 1-3 fluorines, or $C_3$-$C_6$cycloalkyl optionally substituted with 1-2 fluorines;

$R^3$ is $C_1$-$C_3$alkyl or $C_3$-$C_4$cycloalkyl;

$G^1$ is phenyl substituted with 1-5 fluorines, or $G^1$ is $C_1$-$C_3$ alkyl substituted once with either $G^2$, $G^3$, or $G^4$, or $G^1$ is $C_2$-$C_6$ alkyl substituted with 4-9 fluorines, $C_2$-$C_3$alkyl substituted once with $G^5$, $C_4$-$C_8$alkyl substituted once with $G^6$, $C_3$-$C_6$cycloalkyl substituted with 1-4 fluorines, cyclohexene, or cyclopentene;

$G^2$ is 5-6 membered heteroaryl independently substituted one or two times with $C_1$-$C_2$alkyl wherein $C_1$-$C_2$alkyl is optionally substituted with 1-3 fluorines;

$G^3$ is 6-membered heteroaryl excluding 2-pyridine, 2-pyrazine, and 2-pyrimidine;

$G^4$ is $C_3$-$C_6$cycloalkyl substituted with 1-4 fluorines, $C_3$-$C_6$cycloalkyl substituted with $C_1$-$C_2$alkyl optionally substituted with 1-3 fluorines, or $C_3$-$C_6$cycloalkyl substituted with —O—$C_1$-$C_2$alkyl optionally substituted with 1-3 fluorines;

$G^5$ is —O($C_1$-$C_4$alkyl substituted with 1-5 fluorines), —O($C_3$-$C_4$cycloalkyl substituted with 1-4 fluorines), —N(H)($C_1$-$C_2$alkyl substituted with 1-5 fluorines), —N($C_1$-$C_2$alkyl substituted with 1-5 fluorines)($C_1$-$C_3$alkyl optionally substituted with 1-3 fluorines), —N(H)($SO_2$($C_1$-$C_3$alkyl)), or —N($C_1$-$C_3$alkyl)($SO_2$($C_1$-$C_3$alkyl));

$G^6$ is phenyl or —O—$C_1$-$C_2$alkyl optionally substituted with 1-3 fluorines;

W is selected from:

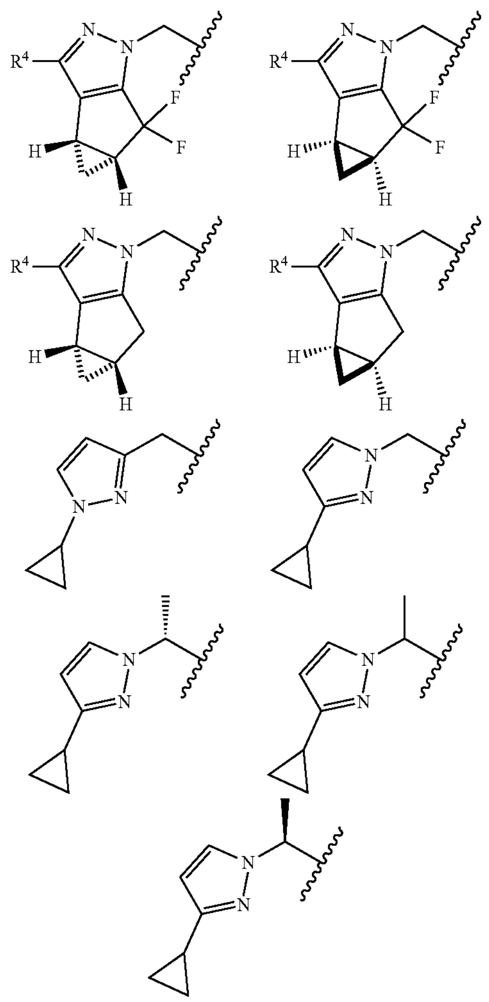

wherein $R^4$ is methyl optionally substituted with 1-3 fluorines or $R^4$ is cyclopropyl.

In another aspect, the present invention discloses a pharmaceutical composition comprising a compound or salt of the invention.

In another aspect, the present invention discloses a method of treating HIV infection in a human comprising administering a compound or salt of the invention.

In another aspect, the present invention discloses a compound or salt of the invention for use in therapy.

In another aspect, the present invention discloses a compound or salt of the invention for use in treating HIV infection in a human.

In another aspect, the present invention discloses the use of a compound or salt of the invention in the manufacture of a medicament for the treatment of HIV infection in a human.

DETAILED DESCRIPTION OF THE INVENTION

In one embodiment, the present invention discloses compounds of Formula I and pharmaceutically acceptable salts thereof wherein W is the following:

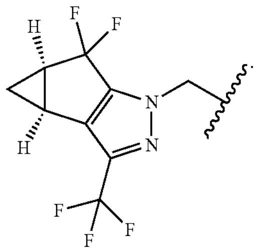 [SMILES: *Cn1nc(C(F)(F)F)c2c1C(F)(F)[C@@H]1C[C@H]21]

In one embodiment, the present invention discloses compounds of Formula I and pharmaceutically acceptable salts thereof wherein W is the following:

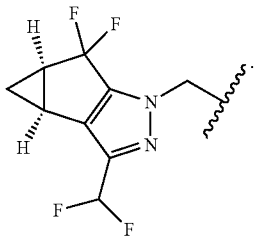 [SMILES: *Cn1nc(C(F)F)c2c1C(F)(F)[C@@H]1C[C@H]21]

In one embodiment, the present invention discloses compounds of Formula I and pharmaceutically acceptable salts thereof wherein W is the following:

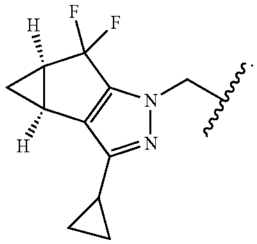 [SMILES: *Cn1nc(C2CC2)c2c1C(F)(F)[C@@H]1C[C@H]21]

In one embodiment, the present invention discloses compounds of Formula I and pharmaceutically acceptable salts thereof wherein W is the following:

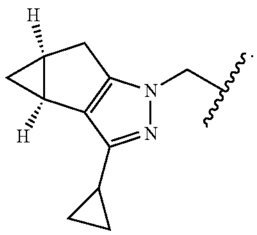 [SMILES: *Cn1nc(C2CC2)c2c1C[C@@H]1C[C@H]21]

In one embodiment, the present invention discloses compounds of Formula I and pharmaceutically acceptable salts thereof wherein W is one of the following:

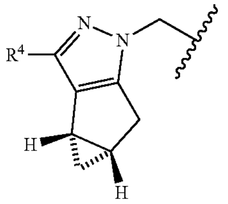

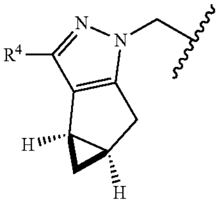

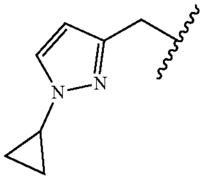

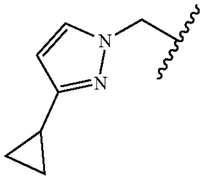

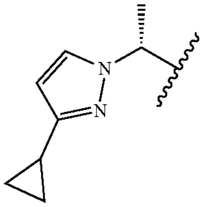

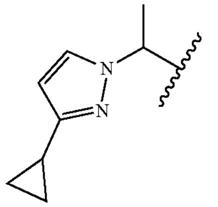

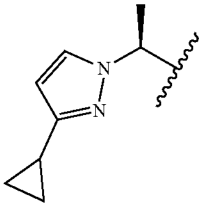

wherein $R^4$ is methyl optionally substituted with 1-3 fluorines or $R^4$ is cyclopropyl.

In one embodiment, the present invention discloses compounds of Formula I and pharmaceutically acceptable salts thereof wherein $R^1$ is Cl; $R^2$ is methyl, 2,2-difluoroethyl, or 2,2,2-trifluoroethyl; and $R^3$ is methyl or cyclopropyl.

In one embodiment, the present invention discloses compounds of Formula I and pharmaceutically acceptable salts thereof wherein $X^3$ is H.

In one embodiment, the present invention discloses compounds of Formula I and pharmaceutically acceptable salts thereof wherein $X^1$ is F and $X^2$ is F.

In one embodiment, the present invention discloses compounds of Formula I and pharmaceutically acceptable salts thereof wherein if $X^3$ is H then at least one of $X^1$ and $X^2$ is other than F.

In one embodiment, the present invention discloses compounds of Formula I and pharmaceutically acceptable salts thereof wherein $G^1$ is $C_1$-$C_3$ alkyl substituted once with a 5-6 membered heteroaryl independently substituted one or two times with $C_1$-$C_2$ alkyl wherein $C_1$-$C_2$ alkyl is optionally substituted with 1-3 fluorines.

In one embodiment, the present invention discloses compounds of Formula I and pharmaceutically acceptable salts thereof wherein $G^1$ is $C_1$-$C_3$ alkyl substituted once with a 6-membered heteroaryl excluding 2-pyridine, 2-pyrazine, and 2-pyrimidine.

In one embodiment, the present invention discloses compounds of Formula I and pharmaceutically acceptable salts thereof wherein $G^1$ is $C_1$-$C_3$ alkyl substituted once with $C_3$-$C_6$ cycloalkyl wherein $C_3$-$C_6$ is substituted with 1-4 fluorines.

In one embodiment, the present invention discloses compounds of Formula I and pharmaceutically acceptable salts thereof wherein $G^1$ is $C_1$-$C_3$ alkyl substituted once with $C_3$-$C_6$ cycloalkyl wherein $C_3$-$C_6$ is substituted with —($C_1$-$C_2$ alkyl optionally substituted with 1-3 fluorines).

In one embodiment, the present invention discloses compounds of Formula I and pharmaceutically acceptable salts thereof wherein $G^1$ is $C_1$-$C_3$ alkyl substituted once with $C_3$-$C_6$ cycloalkyl wherein $C_3$-$C_6$ is substituted with —O($C_1$-$C_2$ alkyl optionally substituted with 1-3 fluorines).

In one embodiment, the present invention discloses compounds of Formula I and pharmaceutically acceptable salts thereof wherein $G^1$ is $C_2$-$C_3$ alkyl substituted once with —O($C_1$-$C_4$ alkyl substituted with 1-5 fluorines).

In one embodiment, the present invention discloses compounds of Formula I and pharmaceutically acceptable salts thereof wherein $G^1$ is $C_2$-$C_6$ alkyl substituted with 4-9 fluorines.

In one embodiment, the present invention discloses compounds of Formula I and pharmaceutically acceptable salts thereof wherein $G^1$ is one of the following:

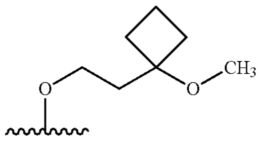
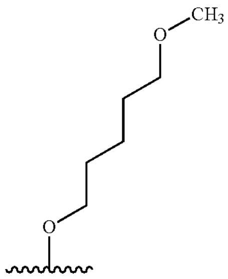
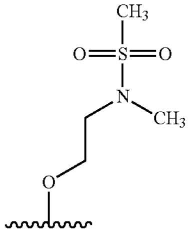
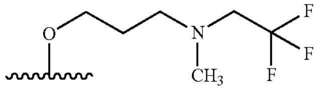
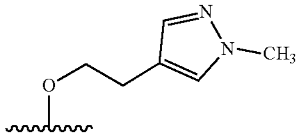
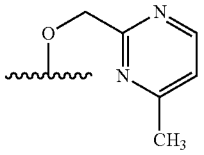
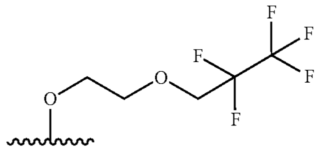
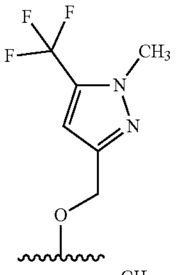
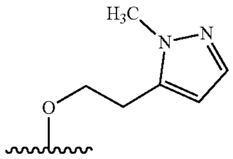
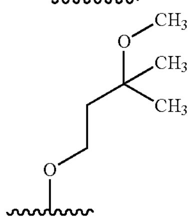

-continued

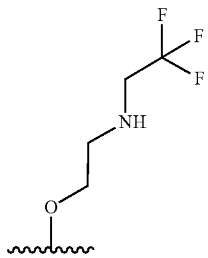
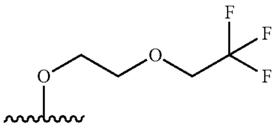
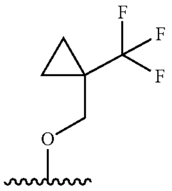
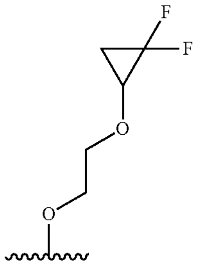
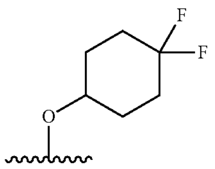
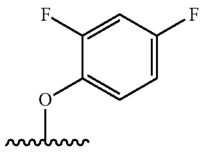
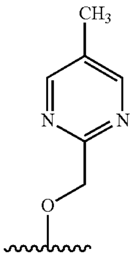
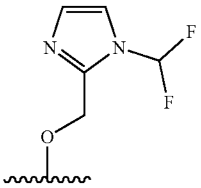
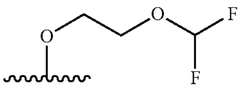
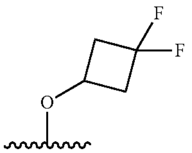
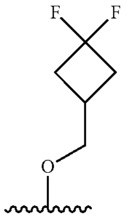
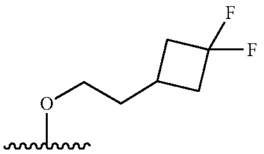
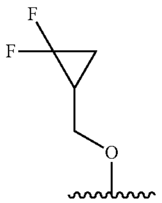
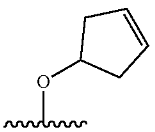
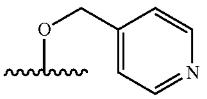

-continued

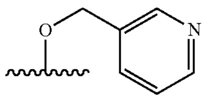

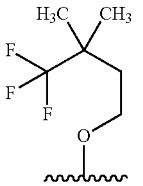

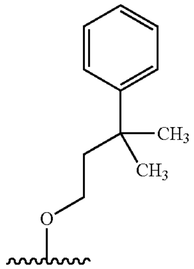

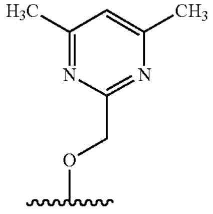

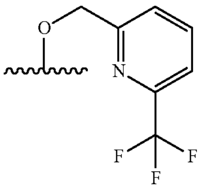

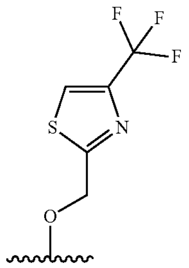

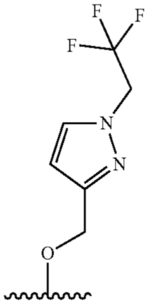

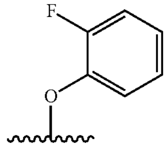

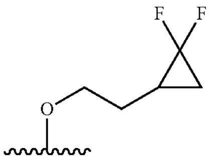

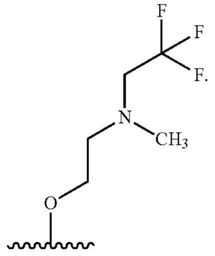

In one embodiment, the present invention discloses compounds of Formula I and pharmaceutically acceptable salts thereof wherein $G^1$ is of the following:

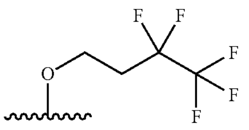

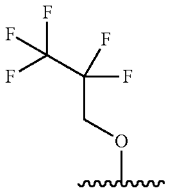

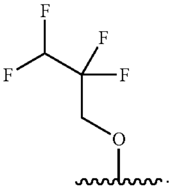

In one embodiment, the present invention discloses compounds of Formula I and pharmaceutically acceptable salts thereof wherein $G^1$ is the following:

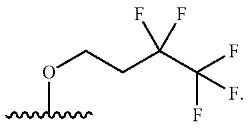 [SMILES: *OCCC(F)(F)C(F)(F)F]

In one embodiment, the present invention discloses compounds of Formula I and pharmaceutically acceptable salts thereof wherein $G^1$ is the following:

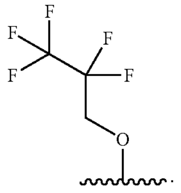

In one embodiment, the present invention discloses compounds of Formula I and pharmaceutically acceptable salts thereof wherein $G^1$ is the following:

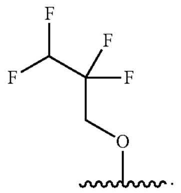

In one embodiment, the present invention discloses compounds of Formula I and pharmaceutically acceptable salts thereof wherein $G^1$ is the following:

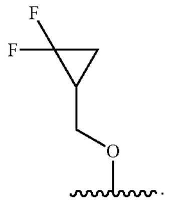 [SMILES: *OCC1CC1(F)F]

In one embodiment, the present invention discloses compounds of Formula I and pharmaceutically acceptable salts thereof wherein $G^1$ is the following:

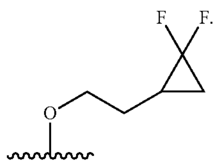 [SMILES: *OCCC1CC1(F)F]

In one embodiment, the present invention discloses compounds of Formula I and pharmaceutically acceptable salts thereof wherein $G^1$ is the following:

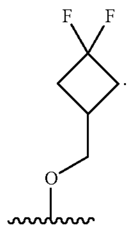 [SMILES: *OCC1CC(F)(F)C1]

In one embodiment, the present invention discloses compounds of Formula I and pharmaceutically acceptable salts thereof wherein $G^1$ is the following:

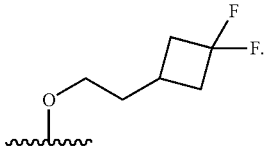 [SMILES: *OCCC1CC(F)(F)C1]

In one embodiment, the present invention discloses compounds of Formula I and pharmaceutically acceptable salts thereof wherein $G^1$ is the following:

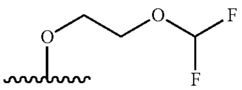 [SMILES: *OCCOC(F)F]

In one embodiment, the present invention discloses compounds of Formula I and pharmaceutically acceptable salts thereof wherein $G^1$ is the following:

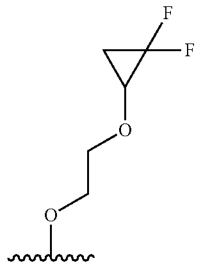 [SMILES: *OCCOC1CC1(F)F]

In one embodiment, the present invention discloses compounds of Formula I and pharmaceutically acceptable salts thereof wherein $G^1$ is the following:

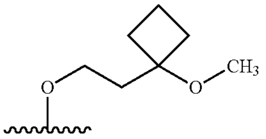 [SMILES: *OCCC1(OC)CCC1]

In one embodiment, the present invention discloses compounds of Formula I and pharmaceutically acceptable salts thereof wherein $G^1$ is the following:

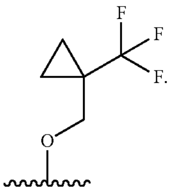 [SMILES: *OCC1(C(F)(F)F)CC1]

In one embodiment, the present invention discloses compounds of Formula I and pharmaceutically acceptable salts thereof wherein $G^1$ is the following:

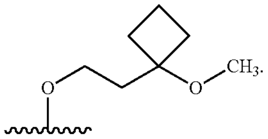 [SMILES: *OCCC1(OC)CCC1]

In one embodiment, the present invention discloses compounds of Formula I and pharmaceutically acceptable salts thereof wherein $G^1$ is the following:

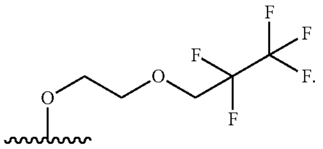 [SMILES: *OCCOCC(F)(F)C(F)(F)F]

In one embodiment, the present invention discloses compounds of Formula I and pharmaceutically acceptable salts thereof wherein $G^1$ is the following:

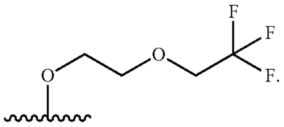 [SMILES: *OCCOCC(F)(F)F]

In one embodiment, the present invention discloses compounds of Formula I and pharmaceutically acceptable salts thereof wherein $G^1$ is the following:

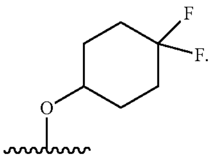 [SMILES: *OC1CCC(F)(F)CC1]

In one embodiment, the present invention discloses compounds of Formula I and pharmaceutically acceptable salts thereof wherein the stereochemistry is as depicted below:

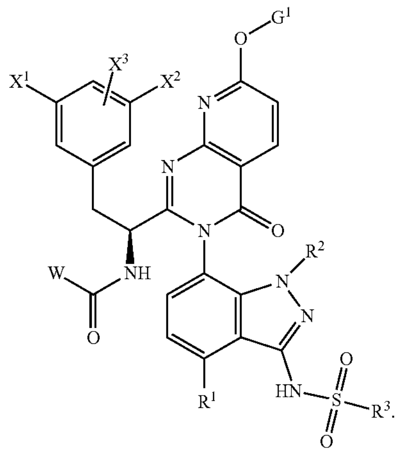

In one embodiment, the present invention discloses compounds of Formula I and pharmaceutically acceptable salts thereof wherein the stereochemistry is as depicted below:

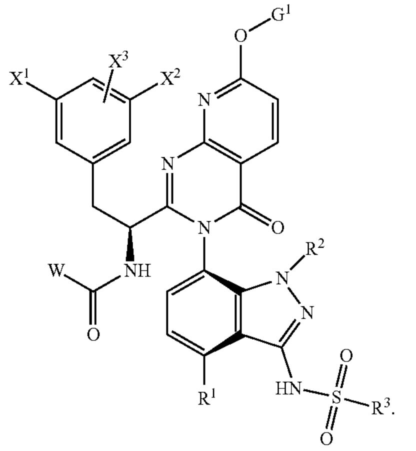

In one embodiment, the present invention discloses a compound which is:

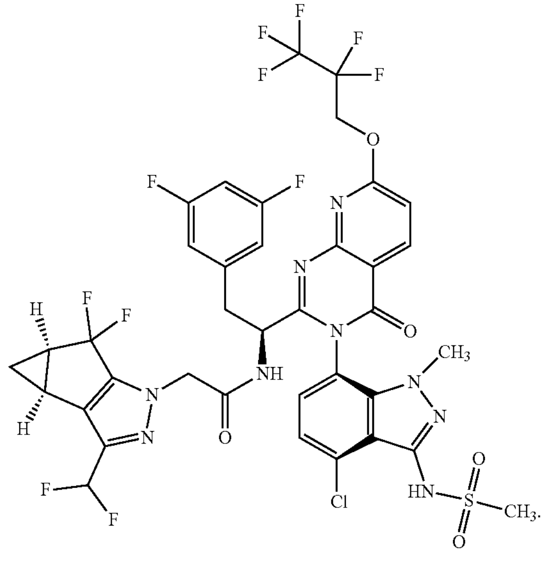

In one embodiment, the present invention discloses a compound which is:

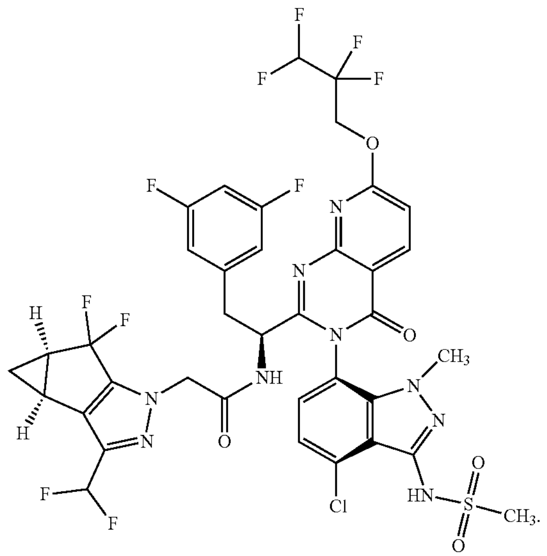

In one embodiment, the present invention discloses a compound which is:

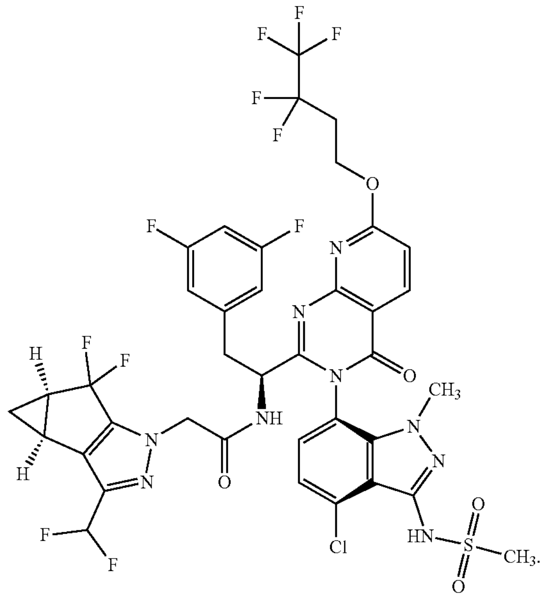

In one embodiment, the present invention discloses a compound which is:

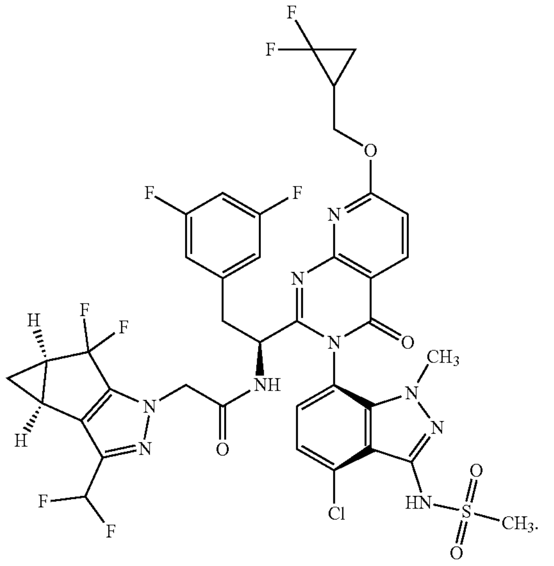

In one embodiment, the present invention discloses a compound which is:

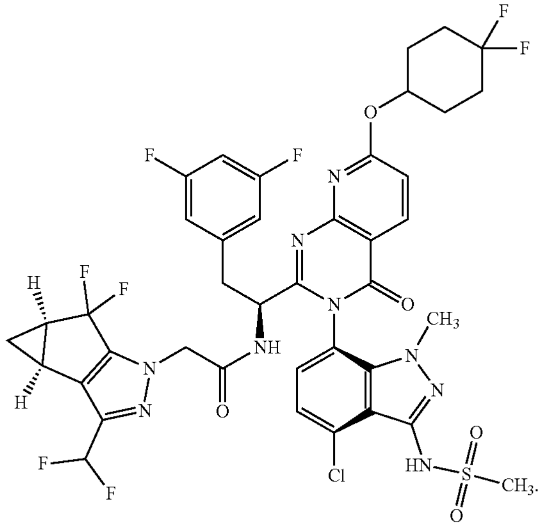

The salts of the invention are pharmaceutically acceptable. Such salts may be acid addition salts or base addition salts. For a review of suitable pharmaceutically acceptable salts see, for example, Berge et al, J. Pharm, Sci., 66, 1-19, 1977.

Representative pharmaceutically acceptable acid addition salts include, but are not limited to, 4-acetamidobenzoate, acetate, adipate, alginate, ascorbate, aspartate, benzenesulfonate (besylate), benzoate, bisulfate, bitartrate, butyrate, calcium edetate, camphorate, camphorsulfonate (camsylate), caprate (decanoate), caproate (hexanoate), caprylate (octanoate), cinnamate, citrate, cyclamate, digluconate, 2,5-dihydroxybenzoate, disuccinate, dodecylsulfate (estolate), edetate (ethylenediaminetetraacetate), estolate (lauryl sulfate), ethane-1,2-disulfonate (edisylate), ethanesulfonate (esylate), formate, fumarate, galactarate (mucate), gentisate (2,5-dihydroxybenzoate), glucoheptonate (gluceptate), gluconate, glucuronate, glutamate, glutarate, glycerophosphorate, glycolate, hexylresorcinate, hippurate, hydrabamine (N,N'-di(dehydroabietyl)-ethylenediamine), hydrobromide, hydrochloride, hydroiodide, hydroxynaphthoate, isobutyrate, lactate, lactobionate, laurate, malate, maleate, malonate, mandelate, methanesulfonate (mesylate), methylsulfate, mucate, naphthalene-1,5-disulfonate (napadisylate), naphthalene-2-sulfonate (napsylate), nicotinate, nitrate, oleate, palmitate, p-aminobenzenesulfonate, p-aminosalicyclate, pamoate (embonate), pantothenate, pectinate, persulfate, phenylacetate, phenylethylbarbiturate, phosphate, polygalacturonate, propionate, p-toluenesulfonate (tosylate), pyroglutamate, pyruvate, salicylate, sebacate, stearate, subacetate, succinate, sulfamate, sulfate, tannate, tartrate, teoclate (8-chlorotheophyllinate), thiocyanate, triethiodide, undecanoate, undecylenate, and valerate.

Representative pharmaceutically acceptable base addition salts include, but are not limited to, aluminium, 2-amino-2-(hydroxymethyl)-1,3-propanediol (TRIS, tromethamine), arginine, benethamine (N-benzylphenethylamine), benzathine (N,N'-dibenzylethylenediamine), bis-(2-hydroxyethyl) amine, bismuth, calcium, chloroprocaine, choline, clemizole (1-p chlorobenzyl-2-pyrrolildine-1'-ylmethylbenzimidazole), cyclohexylamine, dibenzylethylenediamine, diethylamine, diethyltriamine, dimethylamine, dimethylethanolamine, dopamine, ethanolamine, ethylenediamine, L-histidine, iron, isoquinoline, lepidine, lithium, lysine, magnesium, meglumine (V-methylglucamine), piperazine, piperidine, potassium, procaine, quinine, quinoline, sodium, strontium, t-butylamine, and zinc.

In one embodiment, the compositions of this invention further comprise a pharmaceutically acceptable excipient. In the method of this invention, preferred routes of administration are oral and by injection to deliver subcutaneously or intramuscularly. Therefore, preferred pharmaceutical compositions include compositions suitable for oral administration (for example tablets) and compositions suitable for subcutaneous or intramuscular injection.

In another aspect the present invention discloses methods of preventing HIV infection in a human or reducing the risk of infection, comprising administering a compound or salt of this invention. Pre-exposure prophylaxis (or PrEP) is when people at risk for HIV infection take daily medicine to lower their chances of getting HIV infection. PrEP has been shown to be effective in reducing the risk of infection.

The compounds and salts of this invention are believed to have as their biological target the HIV capsid and thus their mechanism of action is to modify in one or more ways the function of the HIV capsid.

The compounds and salts of the present invention may be employed alone or in combination with other therapeutic agents. Combination therapies according to the present invention thus comprise the administration of at least one compound or salt of the invention, and the administration of at least one other agent which may be useful in the treatment of HIV infection. A compound or salt of the present invention, and the other agent may be formulated and administered together in a single pharmaceutical composition or may be formulated and administered separately. When formulated and administered separately, administration may occur simultaneously or sequentially in any order. Suitable other agents include, for example, abacavir, atazanavir, bictegravir, cabotegravir, darunavir, delavirdine, didanosine, dideoxyinosine, dolutegravir, doravirine, efavirenz, elvitegravir, emtricitabine, etavirine, fosamprenavir, fostemsavir, indinavir, slatravir, lamivudine, lopinavir, maraviroc, nelfinavir, nevirapine, raltegravir, rilpiverine, ritonavir, saquinavir, stavudine, tipranavir, tenofovir, tenofovir alafenamide, tenofovir disoproxil fumarate, zalcitabine, zidovudine, GSK4000422, GSK4023991, GSK3640254, GSK3739937, and N6LS. Preferred agents include, for example, dolutegravir, bictegravir, islatravir, lamivudine, fostemsavir, and cabotegravir. Particularly preferred agents include, for example, dolutegravir, bictegravir, lamivudine, fostemsavir, and cabotegravir.

EXAMPLES

Preparation of bicyclo[3.1.0]hexan-3-ol

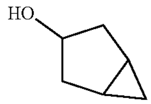

To a stirred solution of cyclopent-3-enol (130 g, 1545 mmol) in DCM (1200 mL) under $N_2$ atmosphere at 0-5° C. was added dropwise a solution of diethyl zinc in hexane (1.0 M, 3091 mL, 3091 mmol) over a period of 3 h. To the solution at 0° C. was added dropwise a solution of diiodomethane (249 mL, 3091 mmol) in DCM (300 mL) over a period of 1 h. The reaction mixture was allowed to warm to 27° C. upon which formation of a white precipitation was observed. The mixture stirred for 16 h. Progress of the reaction was monitored by TLC ($SiO_2$, 20% EtOAc/pet, Rf=0.3, UV-inactive, PMA-active). The reaction mixture was quenched via the careful addition of aq. saturated $NH_4Cl$ solution (1.5 L). The mixture was filtered through pad of Celite. The aqueous layer was extracted with DCM (2×1 L). The combined organic layers were dried over anhydrous $Na_2SO_4$, filtered and then concentrated under reduced pressure to afford crude bicyclo[3.1.0]hexan-3-ol as red liquid, 180 g. $^1H$ NMR (400 MHz, $CDCl_3$) δ=4.41-4.35 (m, 1H), 2.18-2.05 (m, 2H), 1.73 (d, 7=13.9 Hz, 2H), 1.35-1.25 (m, 2H), 1.21-1.14 (m, 1H), 0.57-0.43 (m, 2H). GCMS: m/z=98.1).

Preparation of bicyclo[3.1.0]hexan-3-one

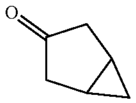

To a stirred solution of bicyclo[3.1.0]hexan-3-ol (210 g, 2054 mmol) in DCM (5000 mL) under $N_2$ atmosphere at 0° C. was added portion-wise Dess-Martin periodinane (954 g, 225 mmol). The mixture was allowed to warm to 27° C. and was then stirred for 16 h. Progress of the reaction was monitored by TLC ($SiO_2$, 20% Acetone/Hex, Rf=0.3, UV in-active, PMA-active). The reaction mixture was filtered through pad of Celite and the filtrate was washed with aq. NaOH (1N, 8×1 L). The combined aqueous phases were extracted with DCM (5×1 L). The combined organic layers were dried over anhydrous $Na_2SO_4$, filtered, and then concentrated under reduced pressure (bath temperature: 20° C.) to afford crude bicyclo[3.1.0]hexan-3-one as brown liquid. The liquid was further purified by downward distillation at 70° C. to afford bicyclo[3.1.0]hexan-3-one as a pale-yellow viscous liquid, 125 g (62%). $^1H$ NMR (400 MHz, $CDCl_3$) δ=2.61-2.54 (m, 2H), 2.17-2.12 (m, 2H), 1.54-1.46 (m, 2H), 0.92-0.86 (m, 1H), −0.01-0.08 (m, 1H); GCMS: M/Z=96.1.

Preparation of 2-(2,2-difluoroacetyl)bicyclo[3.1.0]hexan-3-one

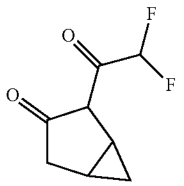 [SMILES: O=C1CC2CC2C1C(=O)C(F)F]

To a stirred solution of bicyclo[3.1.0]hexan-3-one (125 g, 1274 mmol) in THE (1500 mL) under $N_2$ atmosphere at −78° C. was added LDA (2.0 M in THF, 0.701 L, 1402 mmol). The solution was stirred for 1 h at −78° C. To the solution was added slowly over 30 minutes a solution of ethyldifluoroacetate (174 g, 1402 mmol) in THE (300 mL) maintaining a temperature of −78° C. The reaction mixture was allowed to warm to 27° C. and was then stirred for 1 h. Progress of the reaction was monitored by TLC ($SiO_2$, 20% Acetone/Hexane, Rf=0.3, UV-active). The reaction mixture was quenched via the addition of aq. HCl (1N, 2000 mL). The mixture was stirred for 30 min. and then was extracted with EtOAc (3×1000 mL). The combined organic layers were washed with brine (1000 mL), dried over anhydrous $Na_2SO_4$ and filtered. The filtrate was concentrated under reduced pressure to afford 2-(2,2-difluoroacetyl)bicyclo[3.1.0]hexan-3-one as a pale-yellow viscous liquid, 180 g (71%). $^1H$ NMR (400 MHz, $CDCl_3$) δ=6.18 (t, J=54.8 Hz, 1H), 2.70-2.62 (m, 1H), 2.35 (d, J=19.4 Hz, 1H), 2.14 (br s, 1H), 1.26-1.21 (m, 1H), 1.04-1.03 (m, 1H), 0.22-0.21 (m, 1H), LCMS: M/Z=173.17).

Preparation of ethyl 2-(3-(difluoromethyl)-3b,4,4a,5-tetrahydro-1H-cyclopropa[3,4]cyclopenta[1,2-c]pyrazol-1-yl)acetate

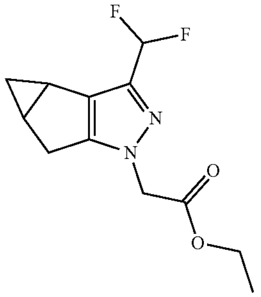 [SMILES: CCOC(=O)Cn1nc(C(F)F)c2c1CC1CC21]

To a stirred solution of 2-(2,2-difluoroacetyl)bicyclo[3.1.0]hexan-3-one (180 g, 910 mmol) in ethanol (2 L) under $N_2$ atmosphere at 27° C. was added ethyl 2-hydrazinylacetate hydrochloride (422 g, 2729 mmol) followed by sulfuric acid (20 mL, 375 mmol). The mixture was stirred for 30 min. and then was heated to 100° C. and stirred for 16 h. Progress of the reaction was monitored by TLC ($SiO_2$, 20% Acetone/Hexane, Rf=0.3, UV-active). The reaction mixture was concentrated under reduced pressure. The residue was dissolved in EtOAc (2000 mL) and was washed with water (2×1 L), brine (1.0 L), dried over anhydrous $Na_2SO_4$, filtered, and then was concentrated under reduced pressure. The resulting residue was subjected to silica gel column chromatography (pet.:acetone 100:0→98:2) to afford ethyl 2-(3-(difluoromethyl)-3b,4,4a,5-tetrahydro-1H-cyclopropa[3,4]cyclopenta[1,2-c]pyrazol-1-yl)acetate as an off-white solid, 110 g (46%). $^1$H NMR (400 MHz, DMSO-$d_6$) δ=6.86 (t, J=54.8 Hz, 1H), 4.93 (s, 2H), 4.14 (q, 3=7.2 Hz, 2H), 2.88-2.79 (m, 1H), 2.76-2.68 (m, 1H), 2.14-2.04 (m, 2H), 1.19 (t, 3=7.2 Hz, 3H), 1.10-1.03 (m, 1H), 0.14 (q, 3=4.3 Hz, 1H).

Preparation of ethyl 2-(3-(difluoromethyl)-5-oxo-3b,4,4a,5-tetrahydro-1H-cyclopropa[3,4]cyclopenta[1,2-c]pyrazol-1-yl)acetate

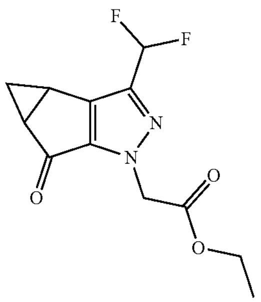 [SMILES: CCOC(=O)Cn1nc(C(F)F)c2c1C(=O)C1CC21]

To a stirred solution of ethyl 2-(3-(difluoromethyl)-3b,4,4a,5-tetrahydro-1H-cyclopropa[3,4]cyclopenta[1,2-c]pyrazol-1-yl)acetate (110 g, 422 mmol) and Celite (395 g) in cyclohexane (3.5 L) at 0° C. was added portion-wise pyridinium dichromate (794 g, 2110 mmol). To the mixture under nitrogen atmosphere was added dropwise tert-butyl hydroperoxide (355 mL, 2130 mmol) over a period of 10 min. The reaction mixture was warmed to 27° C. and was then stirred at that temperature for 48 h. Progress of the reaction was monitored by TLC ($SiO_2$, 30% Acetone/pet, Rf=0.4, UV-active). The reaction mixture was filtered, and the filter cake was extracted with EtOAc (1000 mL). The filtrate was washed with saturated aq. $Na_2S_2O_3$ (2×500 mL); saturated aq. $FeSO_4$ (300 mL); and then brine (500 mL). The organic layer was dried over anhydrous $Na_2SO_4$, filtered and concentrated under reduced pressure to obtain the crude title compound (150 g).

Preparation of ethyl 2-(3-(difluoromethyl)-4,4a-dihydrospiro[cyclopropa[3,4]cyclopenta[1,2-c]pyrazole-5,2'-[1,3]dithiolane]-1(3bH)-yl)acetate

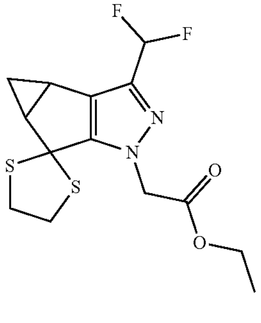 [SMILES: CCOC(=O)Cn1nc(C(F)F)c2c1C1(SCCS1)C1CC21]

To a stirred solution of ethyl 2-(3-(difluoromethyl)-5-oxo-3b,4,4a,5-tetrahydro-1H-cyclopropa[3,4]cyclopenta[1,2-c]pyrazol-1-yl)acetate (75 g, 269 mmol) in DCM (1500 mL) at 27° C. under nitrogen atmosphere was added ethane-1,2-dithiol (43.0 mL, 511 mmol) followed by the addition of boron trifluoride acetic acid (72.6 mL, 511 mmol). The solution was stirred for 16 h. Progress of the reaction was monitored by TLC ($SiO_2$, 20% Acetone/Pet, Rf=0.35, UV-Active). After completion, the reaction mixture was cooled to 0° C. and quenched via the addition of aq. saturated $NaHCO_3$(500 mL). The mixture was extracted with DCM (2×1000 mL). The combined organics were washed with brine (1000 mL), dried over anhydrous $Na_2SO_4$, filtered and concentrated under reduced pressure to obtain a brown liquid. This material was subjected to silica gel column chromatography (Pet.:EtOAc 95:5→90:10) to afford ethyl 2-(3-(difluoromethyl)-4,4a-dihydrospiro[cyclopropa[3,4]cyclopenta[1,2-c]pyrazole-5,2'-[1,3]dithiolane]-1(3bH)-yl)acetate as an off-white solid, 80 g (74%). 1H-NMR (400 MHz, $CDCl_3$) δ=6.61 (t, J=55.2 Hz, 1H), 5.00-4.85 (m, 2H), 4.29-4.19 (m, 2H), 3.55-3.46 (m, 4H), 2.63-2.53 (m, 1H), 2.49-2.38 (m, 1H), 1.30-1.24 (m, 4H), 0.65-0.60 (m, 1H). LCMS M+H=346.9.

Preparation of ethyl 2-(3-(difluoromethyl)-5,5-difluoro-3b,4,4a,5-tetrahydro-1H-cyclopropa[3,4]cyclopenta[1,2-c]pyrazol-1-yl)acetate

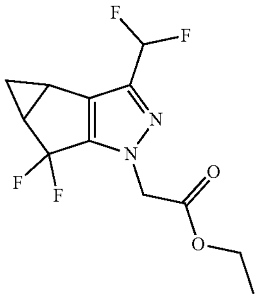 [SMILES: CCOC(=O)Cn1nc(C(F)F)c2c1C(F)(F)C1CC21]

To a stirred solution of 1,3-dibromo-5,5-dimethylimidazolidine-2,4-dione (26.3 g, 92 mmol) in DCM (20 mL) at −70° C. under $N_2$ atmosphere was added HF-pyridine (2.460 g, 24.83 mmol). The solution was for 30 min. To the solution was added a solution of ethyl 2-(3-(difluoromethyl)-4,4a-dihydrospiro[cyclopropa[3,4]cyclopenta[1,2-c]pyrazole-5,2'-1,3]dithiolane]-1(3bH)-yl)acetate (10 g, 25 mmol) in DCM (20 mL). The reaction mixture was allowed to warm to −40° C. and then was stirred at that temperature for 1 h. Progress of the reaction was monitored by TLC ($SiO_2$, 30% EtOAc/Pet, Rf=0.3, UV in-active). The reaction mixture was quenched via the addition of aq. sat. $NaHCO_3$(200 mL). The mixture was warmed to room temperature and was then extracted with EtOAc (2×100 mL). The combined organics were washed with brine (50 mL); dried over anhydrous $Na_2SO_4$; filtered; and were concentrated under reduced pressure to afford a brown solid. This material was subjected to silica gel column chromatography (Pet.:EtOAc 100:0->75-25) to afford ethyl 2-(3-(difluoromethyl)-5,5-difluoro-3b,4,4a,5-tetrahydro-1H-cyclopropa[3,4]cyclopenta[1,2-c]pyrazol-1-yl)acetate as a pale-yellow solid, 8.5 g (91%). $^1$H NMR (400 MHz, $CDCl_3$) δ=6.62 (t, J=55.2 Hz, 1H), 4.82 (s, 2H), 4.30-4.18 (m, 2H), 2.51-2.37 (m, 2H), 1.42-1.35 (m, 1H), 1.31-1.23 (m, 3H), 1.14-1.08 (m, 1H). LCMS M+H=293.07.

Preparation of 2-(3-(difluoromethyl)-5,5-difluoro-3b,4,4a,5-tetrahydro-1H-cyclopropa[3,4]cyclopenta[1,2-c]pyrazol-1-yl)acetic acid

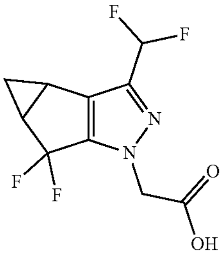 [SMILES: O=C(O)Cn1nc(C(F)F)c2c1C(F)(F)C1CC21]

To a stirred solution of ethyl 2-(3-(difluoromethyl)-5,5-difluoro-3b,4,4a,5-tetrahydro-1H-cyclopropa[3,4]cyclopenta[1,2-c]pyrazol-1-yl)acetate (15 g, 50 mmol) in THE (17 mL) and MeOH (66 mL) at 0° C. under $N_2$ atmosphere was added a solution of LiOH (1.788 g, 74.7 mmol) in water (66 mL). The reaction mixture was allowed to warm to 27° C. and was then stirred for 3 h at that temperature. Progress of the reaction was monitored by TLC ($SiO_2$, 5% MeOH/DCM, Rf=0.2, UV Active). After completion, the reaction mixture was concentrated under reduced pressure; diluted with water (50 mL); and washed with EtOAc (2×250 mL) to remove impurities. The aqueous layer was adjusted to pH 2-3 using aq. HCl (1M), then was extracted with EtOAc (3×1000 mL). The combined organics were dried over anhydrous $Na_2SO_4$; filtered; and concentrated under reduced pressure to afford 2-(3-(difluoromethyl)-5,5-difluoro-3b,4,4a,5-tetrahydro-1H-cyclopropa[3,4]cyclopenta[1,2-c]pyrazol-1-yl)acetic acid as an off white solid, 14 g (98%). LCMS M+H=265.15.

Separation affording 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid and 2-((3bR,4aS)-3-(difluoromethyl)-5,5-difluoro-3b,4,4a,5-tetrahydro-1H-cyclopropa[3,4]cyclopenta[1,2-c]pyrazol-1-yl)acetic acid

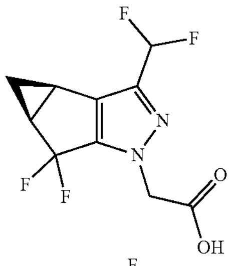

and

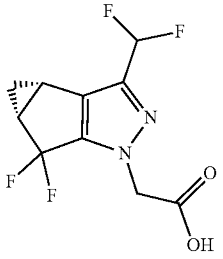

2-(3-(difluoromethyl)-5,5-difluoro-3b,4,4a,5-tetrahydro-1H-cyclopropa[3,4]cyclopenta[1,2-c]pyrazol-1-yl)acetic acid (5.5 g) was dissolved in isopropanol (20 mL). The solution was subjected portion-wise to SFC chiral separation as follows: Instrument=Thar 80; column=Chiralpak IC 30×250 mm, 5 micron; solvent A=super critical $C_{02}$; solvent B=isopropanol with 0.5% isopropylamine (v/v); eluent composition=70% A:30% B; flow-rate=65 g/min; back-pressure=100 bar; temperature=30° C.; injection volume=2.5 mL; detection=220 nm. 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid was collected as peak eluting from 7.5 min. to 14 min; 2-((3bR,4aS)-3-(difluoromethyl)-5,5-difluoro-3b,4,4a,5-tetrahydro-1H-cyclopropa[3,4]cyclopenta[1,2-c]pyrazol-1-yl)acetic acid was collected as a peak eluting from 2.7 min. to 5.8 min. For each enantiomer, the resulting solution was concentrated under reduced pressure and the resulting solids were dissolved in EtOAc, then twice washed with aq. citric acid (1M) followed by water followed by brine. The organic solution was dried over $Na_2SO_4$; filtered; then concentrated in vacuo to afford the separated enantiomer in 80-90% recovery.

Preparation of N-(7-amino-4-chloro-1-methyl-1H-indazol-3-yl)-N-(4-methoxybenzyl)methanesulfonamide

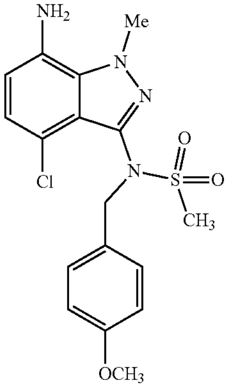 [SMILES: COc1ccc(CN(c2nn(C)c3c(N)ccc(Cl)c23)S(C)(=O)=O)cc1]

Synthesis Scheme:

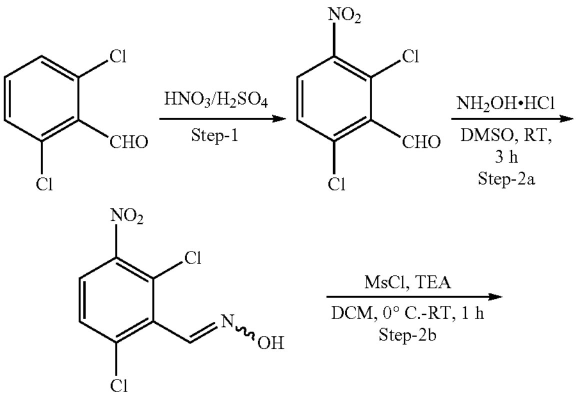

-continued

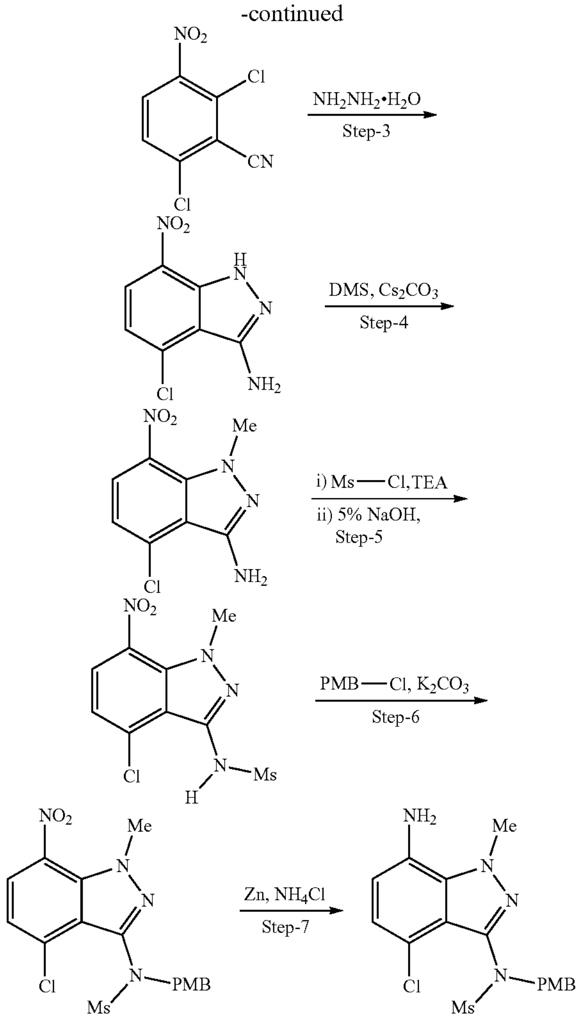

Step 1: Preparation of 2,6-dichloro-3-nitrobenzaldehyde

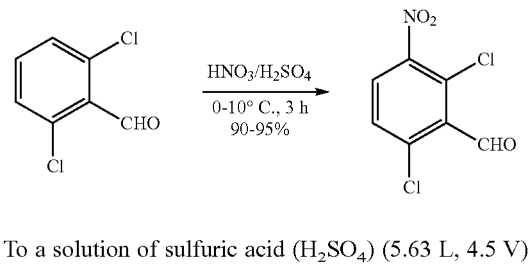

To a solution of sulfuric acid ($H_2SO_4$) (5.63 L, 4.5 V) in a round-bottom flask at 0-5° C. was added 2,6-dichlorobenzaldehyde (1.25 kg, 7.10 mol, 1.0 equiv.) in portions at below 15° C. The reaction mass was stirred at 0-5° C. for 30 min. A solution of freshly prepared nitration mixture [Prepared from Conc. $H_2SO_4$ (0.425 L, 0.34 V) and 70% $HNO_3$ (0.85 kg, 13.49 mol, 1.30 equiv.) at 0° C.] was added to the above reaction mixture at below 10° C. [Note: Reaction is slightly exothermic (3-6° C.); so that addition is preferred at lower temperature]. The reaction mixture was stirred at 5-10° C. for 2-3 h. After completion of the reaction (monitored by TLC), it was quenched with ice cold water (18.75 L, 15 V) at below 25° C. Then the reaction mass was allowed warm to room temperature and stirred for 2 h. The solids were isolated by filtration and then were washed with water (2.5 L, 2.0 V). Bulk residual water was removed from the solids by maintaining vacuum filtration for 60-90 min. The crude wet solid was initially dried under air atmosphere; then in a hot air oven at 50-55° C. for 10-12 h (until moisture content is not more than 5.0%) to get the dried title product, 2,6-dichloro-3-nitrobenzaldehyde (1.44 kg, 92% yield) as a yellow solid. $^1H$ NMR (400 MHz, $CDCl_3$): δ 10.44 (s, 1H), 7.88 (d, J=8.4 Hz, 1H), 7.56 (d, J=8.8 Hz, 1H).

Step 2: Preparation of 2,6-dichloro-3-nitrobenzonitrile

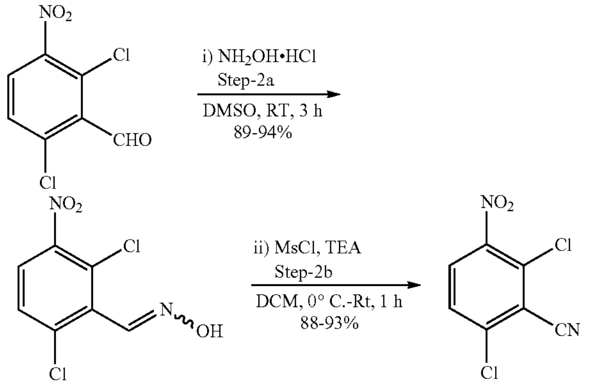

(Step-2a) To a solution of DMSO (5.9 L, 5.0 V)) in a round-bottom flask was added 2,6-dichloro-3-nitrobenzaldehyde (1.17 kg, 5.31 mol, 1.0 equiv.) at room temperature. After being stirred for 30 min at room temperature, hydroxylamine hydrochloride (0.63 kg, 9.04 mol, 1.70 equiv.) was added and the reaction mass was stirred at room temperature for 3 h. After completion of the reaction (monitored by TLC), the reaction mass was quenched by the addition of ice-cold water (18.0 L, 15.0 V) added at a rate sufficient to maintain the temperature below 30° C. (Observation: Solids formed upon water addition). The reaction mass was stirred at room temperature for 60-90 min. The solids were isolated by filtration; washed with water (2.5 L, 2.0 V); followed by washing with a mixture of acetone and hexanes (6.0 L, 1:1 ratio). Bulk residual water was removed from the solids by maintaining vacuum filtration for 60-90 min. The wet solid was initially air dried and then finally dried in a hot air oven at 50-55° C. for 10-12 h (until moisture content was not more than 1.0%) to get the dried target product, 2,6-dichloro-3-nitrobenzaldehyde oxime (1.22 kg, 92% yield) as an off-white solid. The crude product (which contains 10-20% of 2,6-dichloro-3-nitrobenzonitrile) was used directly in the next step without further purification.

(Step-2b) To a stirred solution of the crude oxime (preparation described above, 1.13 kg, 4.80 mol, 1.0 equiv.) in DCM (9.04 L, 8.0 V) at 0-5° C. was added triethylamine ("TEA", 1.02 kg, 10.09 mol, 2.1 equiv.). After being stirred for 5 min, methanesulfonyl chloride (0.60 kg, 5.29 mol, 1.1 equiv.) was added (Observation: An exotherm is noted during the addition) slowly at 15° C. Then the reaction mass was stirred at room temperature for 30-45 min. After completion of the reaction (progress of reaction was monitored by TLC; mobile phase: 20% ethyl acetate in hexanes), the reaction mass was diluted with water (6.78 L, 6.0 V); the organic layer was separated; and the aqueous layer was extracted with DCM (3.4 L, 3.0 V). The combined organic layers were washed with brine (5.65 L, 5.0 V); dried over $Na_2SO_4$; and concentrated under vacuum. The resulting crude solids were triturated with hexanes (4.50 L, 4.0 V) at room temperature. The wet material was dried in a hot air oven at 50-55° C. for 5-6 h to get the dried product, 2,6-dichloro-3-nitrobenzonitrile (0.95 kg, 91% yield) as a yellow solid. $^1H$ NMR (400 MHz, $CDCl_3$): δ 8.07 (d, J=8.8 Hz, 1H), 7.63 (d, J=8.8 Hz, 1H).

Step 3: Preparation of 4-chloro-7-nitro-1H-indazol-3-amine

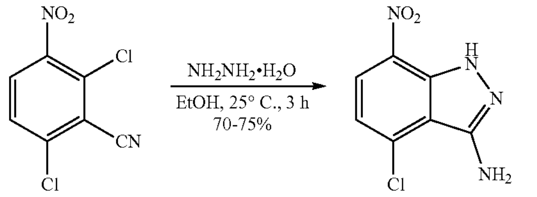

To a stirred solution of 2,6-dichloro-3-nitrobenzonitrile (750.0 g, 3.45 mol, 1.0 equiv.) in ethanol (7.5 L, 10.0 V) at 15-20° C. was slowly added hydrazine hydrate (519.0 g, 10.36 mol, 3.0 equiv.) while maintaining the reaction mass below 25° C. (Observation: Addition is slightly exothermic and solid formation will begin upon addition). The reaction mixture temperature was slowly raised to room temperature and then the mixture was stirred for 3 h (Observation: the quantity of solids will increase during this time). After completion of the reaction (monitored by TLC), the mixture was diluted with water (7.5 L, 10.0 V) and further stirred for 1 h at room temperature. The solids were isolated via filtration and then were washed with water (2.25 L, 3.0 V). The wet solid was washed with a 1:1 ratio mixture of acetone (1.875 L, 2.5 V) and hexanes (1.875 L, 2.5 V). Bulk residual water was removed from the solids by maintaining vacuum filtration for 60-90 min. The wet solid was finally dried in a hot air oven for 7-8 h at 50° C. (until moisture content reaches below 1.5%) to get the dried product, 4-chloro-7-nitro-1H-indazol-3-amine (549.0 g, 75% yield) as a brick red-colored solid. $^1H$ NMR (400 MHz, $CDCl_3$): δ 10.36 (bs, 1H), 8.20 (d, J=8.4 Hz, 1H), 7.07 (d, J=8.40 Hz, 1H), 4.73 (bs, 2H).

Step 4: Preparation of 4-chloro-1-methyl-7-nitro-1H-indazol-3-amine

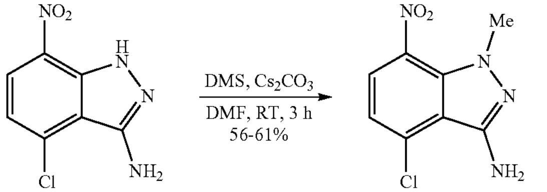

To a stirred solution of 4-chloro-7-nitro-1H-indazol-3-amine (500 g, 0.42 mol, 1.0 equiv.) in DMF (5.0 L, 10.0 V) at 5-10° C. was slowly added cesium carbonate ($Cs_2CO_3$) (1.91 kg, 5.88 mol, 2.5 equiv.) while maintaining the reaction mass below 10° C. After being stirred for 5-10 min, dimethyl sulphate (326.3 g, 2.59 mol, 1.1 equiv.) was added while maintaining the reaction mass below 10° C. (Note: Slow addition is preferred for obtaining more favorable regio-selectivity). Then, the reaction temperature was slowly raised to room temperature and stirring was continued an additional 2 h at the same temperature. After completion of the reaction (monitored by TLC), the reaction mass was quenched by the addition of ice-cold water (15.0 L, 30.0 V) and the resulting mixture was then stirred for 6-8 h at room temperature. The solids were isolated via filtration and were then washed with water (1.5 L, 3.0 V). The wet solid was washed with IPA (1.5 L, 3.0 V) followed by hexanes (1.0 L, 2.0 V). Bulk residual water was removed from the solids by maintaining vacuum filtration for 60-90 min. The wet solid was dried in a hot air oven for 7-8 h at 50° C. (until moisture content is below 1.0%). The isolated material, 4-chloro-1-methyl-7-nitro-1H-indazol-3-amine (319.0 g, 60% yield), was used in the next step without further purification. $^1H$ NMR (400 MHz, $CDCl_3$): δ 7.97 (d, J=8.32 Hz, 1H), 6.97 (d, J=8.24 Hz, 1H), 4.63 (bs, 2H), 3.96 (s, 3H).

Step 5: Preparation of V-(4-chloro-1-methyl-7-nitro-1H-indazol-3-yl)methanesulfonamide

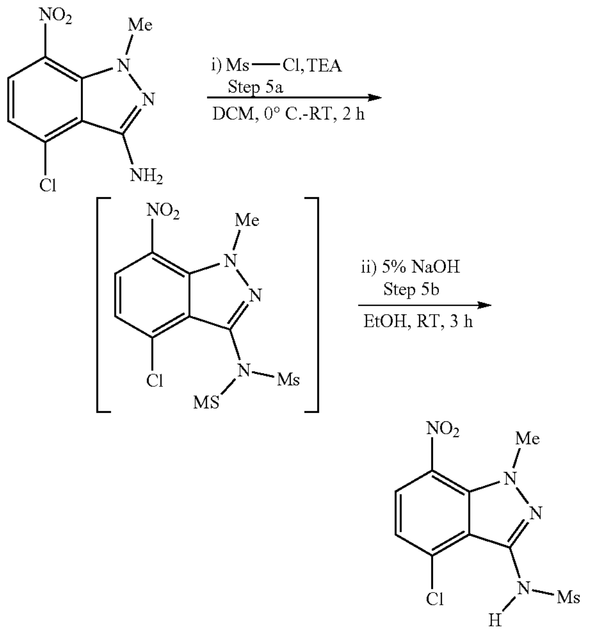

(Step 5a) To a solution of 4-chloro-1-methyl-7-nitro-1H-indazol-3-amine (625.0 g, 2.76 mol, 1.0 equiv.) in DCM (6.25 L, 10.0 V) at 0-5° C. was added triethylamine (TEA) (837.0 g, 8.27 mol, 3.0 equiv.); followed by the addition of 4-dimethylaminopyridine (DMAP) (20.60 g, 0.165 mol, 0.06 equiv.). The reaction mass was stirred for 5-10 min., then methanesulfonyl chloride (MsCl) (790.0 g, 6.89 mol, 2.5 equiv.) added slowly while maintaining the reaction mass below 10° C. The reaction mixture was allowed to warm to room temperature and was then stirred for 1.5-2.0 h. After completion of the reaction (monitored by TLC), the mixture was diluted with water (6.25 L, 10.0 V) and then stirred at room temperature for 15 min. The organic layer was separated, and the aqueous layer was extracted with DCM (6.25 L, 10.0 V). The combined organic layers were washed with brine (1.25 L, 2.0 V), dried over $Na_2SO_4$ and concentrated to get the crude solids. The solids were triturated with hexanes (1.25 L, 2.0 V) at room temperature to obtain the intermediate, N-(4-chloro-1-methyl-7-nitro-1H-indazol-3-yl)-N-(methylsulfonyl)methanesulfonamide, which was used directly in the next step. (ii) To a stirred solution of N-(4-chloro-1-methyl-7-nitro-1H-indazol-3-yl)-N-(methylsulfonyl)methanesulfonamide (prepared above) in ethanol (10.5 L, 20.0 V) at room temperature was added slowly an aq. 5% NaOH solution (4.38 L, 7.0 V) [Note: Slow addition is preferred via dropping funnel]. The reaction mass was stirred at the same temperature for 3 h. After completion of the reaction (monitored by TLC) [Sample preparation for TLC analysis: ~1.0 ml of sample acidified with aq. 2.0 N HCl to reach the pH: 2-3, extract it with ethyl acetate and analyze the organic layer by TLC], the reaction mass was cooled to 0-5° C. and the pH was adjusted to 2-3 by the addition of aq. 2.0 N HCl (3.13 L, 5.0 V) while maintain the reaction temperature below 10° C. [Note: Precipitation occurred upon addition of HCl and increased with stirring]. The reaction mixture was warmed to room temperature and then stirred for 1.5-2.0 h. Solids obtained were isolated via filtration and were then washed with water (1.25 L, 2.0 V); followed by washing with hexanes (1.25 L, 2.0 V). Bulk residual water was removed from the solids by maintaining vacuum filtration for 60-90 min. The wet material was dried in a hot air oven at 50° C. for 6-7 h (Until the moisture content is below 1.0%) to get the dried product, V-(4-chloro-1-methyl-7-nitro-1H-indazol-3-yl)methanesulfonamide (640.0 g, 76%) as a yellow solid. $^1$H NMR (400 MHz, $CDCl_3$): δ 8.05 (d, 7=8.32 Hz, 1H), 7.32 (bs, 1H), 7.17 (d, J=8.28 Hz, 1H), 4.15 (s, 3H), 3.45 (s, 3H).

Step 6: Preparation of N-(4-chloro-1-methyl-7-nitro-1H-indazol-3-yl)-N-(4-methoxybenzyl)methanesulfonamide

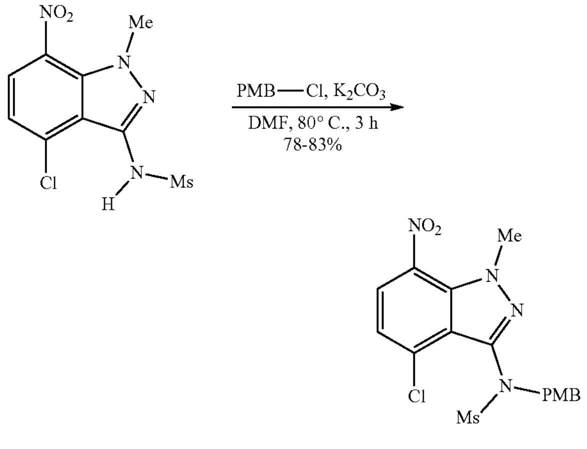

To a mixture of/V(4-chloro-1-methyl-7-nitro-1H-indazol-3-yl)methanesulfonamide (635.0 g, 2.08 mol, 1.0 equiv.) and 1-(chloromethyl)-4-methoxybenzene (359.0 g, 2.30 mol, 1.1 equiv.) in DMF (6.35 L, 10.0 V) at room temperature was added potassium carbonate (374.7 g, 2.70 mol, 1.3 equiv.). The reaction mixture was heated to 80-90° C. and maintained at that temperature for 3 h. After completion of the reaction (monitored by TLC), the mixture was poured into ice cold water (19.05 L, 30.0 V) [Note: Slow quenching with vigorous stirring is preferred to avoid clumping as the product precipitates]. The resulting solids were isolated via filtration and washed with water (1.90 L, 3.0 V); then the solids were washed with hexanes (1.27 L, 2.0 V). Bulk residual water was removed from the solids by maintaining vacuum filtration for 60-90 min. The isolated solid was dissolved in Ethyl acetate (12.7 L, 20.0 V) and charcoal was added (63.5 g). The mixture was heated to 60-70° C. and then stirred for 30-45 min. at that temperature. The mixture was filtered while still hot (40-50° C.) through a pad of Celite and the Celite pad was then extracted with ethyl acetate (3.17 L, 5.0 V). The combined filtrates were concentrated to dryness under reduced pressure at below 50° C. Ethyl acetate (0.635 L, 1.0 V) was added to the solids at room temperature. The resultant solid suspension was stirred for 30 min. The solids were isolated via filtration and then were washed with hexanes (1.27 L, 2.0 V). Residual water was removed from the solids by maintaining vacuum filtration for 45-60 min. to afford the product N-(4-chloro-1-methyl-7-nitro-1H-indazol-3-yl)-V(4-methoxybenzyl) methane sulfonamide (705.0 g, 80% yield) as a yellow solid. $^1$H NMR (400 MHz, $CDCl_3$): δ 7.99 (d, J=8.24 Hz, 1H), 7.27 (d, J=8.68 Hz, 2H), 7.19 (d, J=8.24 Hz, 1H), 6.80 (d, J=8.44 Hz, 2H), 4.95-4.76 (m, 2H), 4.17 (s, 3H), 3.76 (s, 3H), 3.01 (s, 3H).

Step 7: Preparation of N-(7-Amino-4-chloro-1-methyl-1H-indazol-3-yl)-N-(4-methoxybenzyl)methanesulfonamide

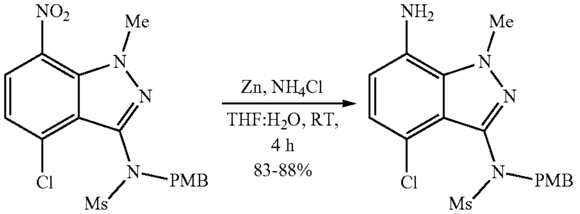

To a stirred suspension of zinc powder (540.0 g, 8.23 mol, 10.0 equiv.) in a mixture of THE (3.50 L, 10.0 V) and water (7.0 L, 20.0 V) at room temperature was added ammonium chloride ($NH_4Cl$) (449.0 g, 8.23 mol, 10.0 equiv.). To the mixture was added N-(4-chloro-1-methyl-7-nitro-1H-indazol-3-yl)-A(4-methoxybenzyl)methanesulfonamide (350 g, 0.823 mol, 1.0 equiv.) in THE (7.0 L, 20.0 V). The reaction mixture was stirred at room temperature for 3-4 h. After completion of the reaction (monitored by in-process TLC/HPLC), the mixture was diluted with ethyl acetate (3.5 L, 10.0 V) and water (1.12 L, 2.5 V). The mixture was stirred for 15 min. The reaction mass was filtered through a pad of Celite bed washing with ethyl acetate (1.75 L, 5.0 V). The bi-phasic filtrate was collected, and the phases were separated. The aqueous layer was extracted with ethyl acetate (3.50 L, 10.0 V). The combined organic layers were washed with brine (3.50 L, 10 V), dried over $Na_2SO_4$, and then concentrated in vacuo to afford a crude solid. To the crude product was added MTBE (3.25 L, 10 V) and the suspension was stirred for 30 min at room temperature. The solids were isolated by filtration. Bulk residual water was removed from the solids by maintaining vacuum filtration for 30-45 min. The wet product was dried in a hot air oven (50° C.) for 2 h to afford the title product, N-(7-amino-4-chloro-1-methyl-1H-indazol-3-yl)-N-(4-methoxybenzyl)methanesulfonamide (276.0 g, 85% yield) as off-white solid. $^1$H NMR (400

MHz, $CDCl_3$): δ7.29-7.26 (m, 2H), 6.86-6.79 (m, 2H), 6.42 (d, 7=7.80 Hz, 1H), 4.99-4.70 (m, 2H), 4.25 (s, 3H), 3.77 (s, 5H), 2.98 (s, 3H).

Preparation of benzyl 2,6-difluoronicotinate

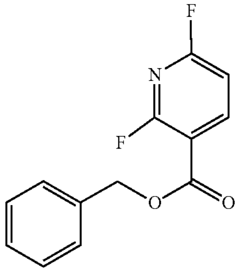 [SMILES: O=C(OCc1ccccc1)c1ccc(F)nc1F]

A mixture of 2,6-difluoronicotinic acid (10.4 g, 65.4 mmol), $K_2CO_3$ (13.55 g, 98 mmol) and benzyl bromide (10.11 mL, 85 mmol) in N,N-Dimethylformamide (200 mL) was stirred at rt for 18 h. The reaction mixture was poured into water, extracted with ethyl acetate, washed with water, washed with brine, dried over $Na_2SO_4$, filtered, and concentrated. The oily residue was purified on silica gel (2×120 g RediSep Gold columns in series) eluting with 0-20% ethyl acetate in hexanes over 10 CV, then eluting with 20% ethyl acetate in hexanes for 10 CV.

Fractions containing the desired product were pooled and then concentrated in vacuo to afford benzyl 2,6-difluoronicotinate (13.83 g, 55.5 mmol, 85% yield) as a yellow oil. $^1H$ NMR (500 MHz, CHLOROFORM-d) δ ppm 8.49-8.56 (m, 1H) 7.34-7.47 (m, 5H) 6.89-6.93 (m, 1H) 5.39-5.40 (m, 2H).

Preparation of benzyl 2-amino-6-fluoronicotinate

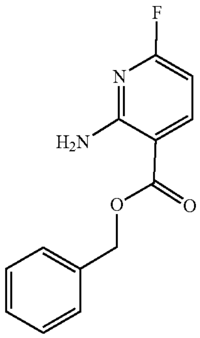 [SMILES: Nc1nc(F)ccc1C(=O)OCc1ccccc1]

A mixture of benzyl 2,6-difluoronicotinate (13.82 g, 55.5 mmol) and 30% aqueous ammonia (36.4 ml, 555 mmol) in N,N-Dimethylformamide (139 ml) was stirred at room temperature for 18 h upon which the clear solution became cloudy. The reaction mixture was poured into water, extracted with ethyl acetate, dried over $Na_2SO_4$, filtered, and concentrated under reduced pressure. The residue was purified on silica gel (2×120 g RediSep Gold columns in series) eluting with 0-20% acetone in hexanes over 15 CV, then eluting with at 20% acetone in hexanes for 10 CV. Two regioisomers are separated by this technique. The desired isomer (major component, first peak to elute) was collected and then concentrated under reduced pressure to afford benzyl 2-amino-6-fluoronicotinate (3.58 g, 14.54 mmol, 26.2% yield) as a white solid. $^1H$ NMR (500 MHz, CHLOROFORM-d) δ ppm 8.21-8.31 (m, 1H) 7.31-7.44 (m, 5H) 6.12-6.24 (m, 1H) 5.26-5.36 (m, 2H). LC/MS: m/z=246.95 [M+1]+.

Preparation of methyl 2-amino-6-fluoronicotinate

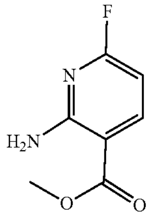

To a solution of 2-amino-6-fluoronicotinic acid (2 g, 12.81 mmol) in N,N-Dimethylformamide (25.6 ml) were added $K_2CO_3$ (2.30 g, 16.65 mmol) and methyl iodide (1.041 mL, 16.65 mmol). The reaction mixture was stirred at rt for 18 h, then quenched by the addition of water. The resulting suspension was filtered and the isolated solids were maintained under active vacuum filtration until residual solvent was removed to afford methyl 2-amino-6-fluoronicotinate (2 g, 11.75 mmol, 92% yield) as a yellow solid. $^1H$ NMR (500 MHz, CHLOROFORM-d) δ ppm 8.21 (t, J=8.20 Hz, 1H) 6.20 (dd, J=8.49, 2.53 Hz, 1H) 3.88 (s, 3H). LC/MS: m/z=170.95 [M+1]+.

Preparation of benzyl 2-amino-6-(2,2,3,3,3-pentafluoropropoxy)nicotinate

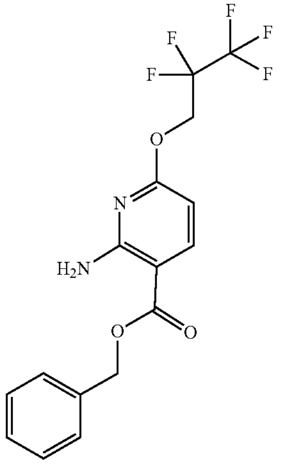 [SMILES: Nc1nc(OCC(F)(F)C(F)(F)F)ccc1C(=O)OCc1ccccc1]

To a solution of 2,2,3,3,3-pentafluoropropan-1-ol (0.731 g, 4.87 mmol) in N,N-Dimethylformamide (12.50 mL) under an atmosphere of nitrogen and cooled in a 0° C. ice bath was added NaH (60% wt. in oil, 0.244 g, 6.09 mmol). The mixture was stirred for 25 min. To the mixture was added a solution of benzyl 2-amino-6-fluoronicotinate (1 g, 4.06 mmol) in N,N-dimethylformamide (1.5 mL). The mixture was stirred for 1 h and then quenched by the addition of with water. The mixture was warmed to room temperature and then extracted with ethyl acetate, dried over $Na_2SO_4$, and filtered. The filtrate was concentrated under reduced pressure to afford benzyl 2-amino-6-(2,2,3,3,3-pentafluoropropoxy)nicotinate (1.82 g) as a yellow oil which was used directly in the next step. $^1H$ NMR (500 MHz, CHLORO- FORM-d) δ ppm 8.07-8.15 (m, 1H) 7.32-7.47 (m, 5H) 6.13 (d, 3-8.64 Hz, 1H) 5.30 (s, 2H) 4.71-4.84 (m, 2H). LC/MS: m/z=377.95 [M+1]+.

Preparation of 2-amino-6-(2,2,3,3,3-pentafluoropropoxy)nicotinic acid

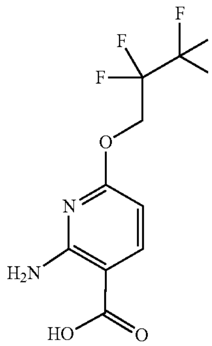

A mixture of benzyl 2-amino-6-(2,2,3,3,3-pentafluoropropoxy)nicotinate (1.52 g, 4.04 mmol) and palladium on carbon (0.430 g, 0.404 mmol) in methanol (81 mL) was stirred under an atmosphere of hydrogen (atmospheric pressure) at ambient temperature for 18 hours. The mixture was filtered through a pad of Celite and the filtrate was concentrated under reduced pressure. The residue was triturated with hexanes and the solids were collected by filtration to afford 2-amino-6-(2,2,3,3,3-pentafluoropropoxy)nicotinic acid (0.93 g, 3.25 mmol, 80% yield) as an off-white solid. $^1$H NMR (500 MHz, DMSO-$d_6$) δ ppm 12.45-12.75 (m, 1H) 8.01 (d, J=8.35 Hz, 1H) 7.16-7.66 (m, 2H) 6.11 (d, J=8.35 Hz, 1H) 5.08 (td, J=14.01, 0.89 Hz, 2H). LC/MS: m/z=287.95 [M+1]+.

Preparation of tert-butyl (S)-(1-(3-(4-chloro-1-methyl-3-(N-(methylsulfonyl)acetamido)-1H-indazol-7-yl)-4-oxo-7-(2,2,3,3,3-pentafluoropropoxy)-3,4-dihydropyrido[2,3-d]pyrimidin-2-yl)-2-(3,5-difluorophenyl)ethyl)carbamate

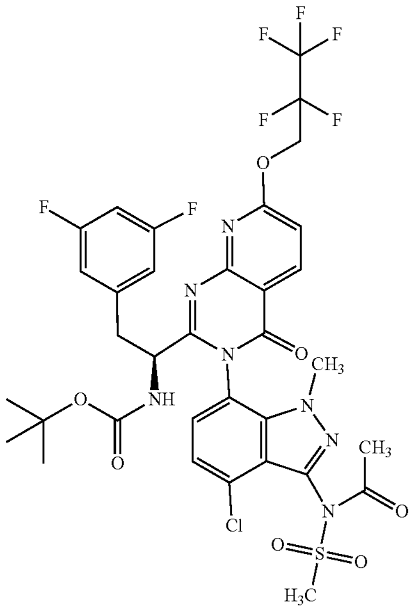 [SMILES: CC(=O)N(c1nn(C)c2c(-n3c([C@H](Cc4cc(F)cc(F)c4)NC(=O)OC(C)(C)C)nc4nc(OCC(F)(F)C(F)(F)F)ccc4c3=O)ccc(Cl)c12)S(C)(=O)=O]

To a suspension of (S)-2-((tert-butoxycarbonyl)amino)-3-(3,5-difluorophenyl)propanoic acid (1.046 g, 3.47 mmol) and 2-amino-6-(2,2,3,3,3-pentafluoropropoxy)nicotinic acid (0.994 g, 3.47 mmol) in acetonitrile (19.02 ml) (yellow solution) at −25° C. was added pyridine (2.043 mL, 25.3 mmol) followed by 2,4,6-tripropyl-1,3,5,2,4,6-trioxatriphosphinane 2,4,6-trioxide ("T3P", 50% wt. in EtOAc, 4.70 mL, 15.78 mmol). The reaction mixture (became a clear solution after T3P addition) was stirred at −25° C. to 12° C. over 5 h. To the mixture was added N-(7-amino-4-chloro-1-methyl-1H-indazol-3-yl)-N-(methylsulfonyl)acetamide (1 g, 3.16 mmol).

The mixture was then stirred for 18 h while warming to rt. The reaction mixture was diluted with ethyl acetate and then washed successively with 1N NaOH, water, 0.5 M citric acid, and water. The organic phase was dried over $Na_2SO_4$ and then concentrated under reduced pressure. The residue was subjected to silica gel chromatography (120 g RediSep Gold column) eluting with 0-60% ethyl acetate in hexanes over 12 CV, then eluting with 60% ethyl acetate in hexanes for 5 CV. Fractions containing the desired fractions were pooled and then concentrated under reduced pressure to afford tert-butyl (S)-(1-(3-(4-chloro-1-methyl-3-(N-(methylsulfonyl)acetamido)-1H-indazol-7-yl)-4-oxo-7-(2,2,3,3,3-pentafluoropropoxy)-3,4-dihydropyrido[2,3-d]pyrimidin-2-yl)-2-(3,5-difluorophenyl)ethyl)carbamate (1.2 g, 1.411 mmol, 45% yield) as a yellow solid, a mixture of diastereomers (atropisomers). LC/MS: m/z=849.95 [M+1]+.

Preparation of (S)—N-((6P)-7-((3P)-2-(1-amino-2-(3,5-difluorophenyl)ethyl)-4-oxo-7-(2,2,3,3,3-pentafluoropropoxy)pyrido[2,3-d]pyrimidin-3(4H)-yl)-4-chloro-1-methyl-1H-indazol-3-yl)-N-(methylsulfonyl)acetamide

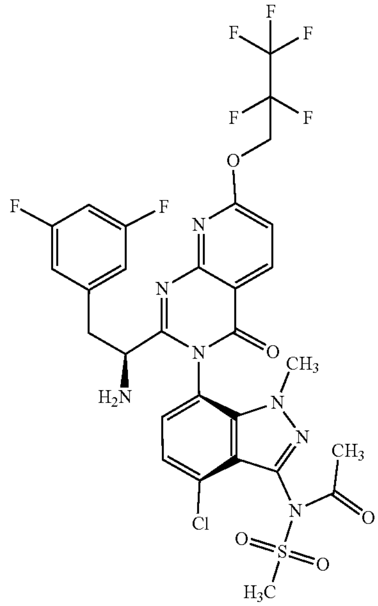

To a solution of tert-butyl (1-(3-(4-chloro-1-methyl-3-(N-(methylsulfonyl)acetamido)-1H-indazol-7-yl)-4-oxo-7-(2,2,3,3,3-pentafluoropropoxy)-3,4-dihydropyrido[2,3-d]pyrimidin-2-yl)-2-(3,5-difluorophenyl)ethyl)carbamate (0.35 g, 0.416 mmol) in dichloromethane (2 mL) was added TFA (0.64 mL, 8.33 mmol). The mixture was stirred at rt for 3 h.

The pale-yellow solution was concentrated under reduced pressure and the resulting residue was dissolved in ethyl acetate. The solution was washed three times with 1 N NaOH (100 mL); dried over $Na_2SO_4$; and then concentrated under reduced pressure to afford an oily residue. The residue was subjected to silica gel chromatography (80 g RediSep Gold column) eluting with 35-100% Solvent A in hexanes over 4 CV, and then eluting with 100% Solvent A over 9 CV; Solvent A=ethyl acetate:hexanes:MeOH (9:9:2). This purification separated the two diastereomers (atropisomers). Fractions corresponding to the first diastereomer to elute (desired) were pooled and concentrated under reduced pressure to afford N-((6P)-7-((3P)-2-(1-amino-2-(3,5-difluorophenyl)ethyl)-4-oxo-7-(2,2,3,3,3-pentafluoropropoxy) pyrido[2,3-d]pyrimidin-3(4H)-yl)-4-chloro-1-methyl-1H-indazol-3-yl)-N-(methylsulfonyl)acetamide (0.1 g, 0.133 mmol, 32.0% yield). LC/MS: m/z=750.1 [M+1]+.

Preparation of 2-amino-6-(2,2,3,3-tetrafluoropropoxy)nicotinic acid

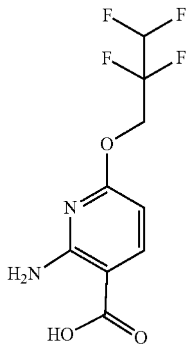 [SMILES: Nc1nc(OCC(F)(F)C(F)F)ccc1C(=O)O]

To a solution of 2-amino-6-fluoronicotinic acid (0.50 g, 3.22 mmol) and 2,2,3,3-tetrafluoropropan-1-ol (1.27 g, 9.65 mmol) in N-Methyl-2-pyrrolidone (NMP) (32.2 mL) was added portion-wise potassium tert-butoxide (1.80 g, 16.08 mmol). The reaction mixture was stirred at rt for 18 h. The reaction was quenched by the addition of aq. 0.5 M citric acid. The mixture was extracted with ethyl acetate, dried over $Na_2SO_4$ and concentrated. The resulting residue was subjected to silica gel chromatography (80 g RediSep Gold column) eluting with 10-80% ethyl acetate in hexanes over 8 CV, then eluting with 80% ethyl acetate in hexanes for 4CV. Fractions containing the desired product were pooled and then concentrated under reduced pressure to afford 2-amino-6-(2,2,3,3-tetrafluoropropoxy)nicotinic acid (0.32 g, 1.193 mmol, 37.1% yield) as a yellow solid. $^1H$ NMR (500 MHz, CHLOROFORM-d) δ ppm 8.12 (d, J=8.64 Hz, 1H) 6.16 (d, J=8.35 Hz, 1H) 5.86-6.10 (m, 1H) 4.70 (tt, J=12.67, 1.49 Hz, 2H). LC/MS: m/z=268.85 [M+1]+.

Preparation of tert-butyl (S)-(1-(3-(4-chloro-1-methyl-3-(N-(methylsulfonyl)acetamido)-1H-indazol-7-yl)-4-oxo-7-(2,2,3,3-tetrafluoropropoxy)-3,4-dihydropyrido[2,3-d]pyrimidin-2-yl)-2-(3,5-difluorophenyl)ethyl)carbamate

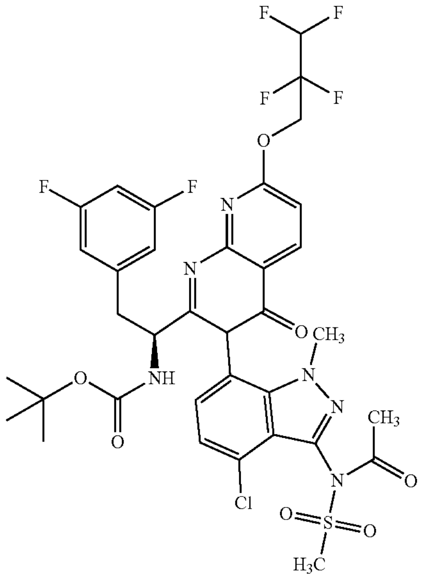 [SMILES: CC(=O)N(c1nn(C)c2c(C3C(=O)c4ccc(OCC(F)(F)C(F)F)nc4N=C3[C@H](Cc3cc(F)cc(F)c3)NC(=O)OC(C)(C)C)ccc(Cl)c12)S(C)(=O)=O]

To a suspension of (S)-2-((tert-butoxycarbonyl)amino)-3-(3,5-difluorophenyl)propanoic acid (0.743 g, 2.466 mmol) and 2-amino-6-(2,2,3,3-tetrafluoropropoxy)nicotinic acid (0.661 g, 2.466 mmol) in acetonitrile (13.50 mL) (yellow solution) at −25° C. was added pyridine (1.450 ml, 17.93 mmol) followed by 2,4,6-tripropyl-1,3,5,2,4,6-trioxatriphosphinane 2,4,6-trioxide ("T3P", 50% wt. in EtOAc, 6.67 ml, 11.21 mmol). The reaction mixture (became a clear solution after T3P addition) was stirred at −25° C. to 12° C. over 5 h. To the mixture was added N-(7-amino-4-chloro-1-methyl-1H-indazol-3-yl)-N-(methylsulfonyl)acetamide (0.71 g, 2.241 mmol). The mixture was stirred for 18 h while warming to rt. The reaction mixture was diluted with ethyl acetate and then successively washed with 1N NaOH, water, 0.5 M citric acid and water. The organic phase was dried over $Na_2SO_4$ and then concentrated under reduced pressure. The residue was subjected to silica gel chromatography (120 g RediSep Gold column) eluting with 0-60% ethyl acetate in hexanes over 15 CV, then eluting with 60% EtOAc in hexanes for 5 CV. Fractions containing the desired product were pooled and then concentrated under reduced pressure to afford tert-butyl (S)-(1-(3-(4-chloro-1-methyl-3-(N-(methylsulfonyl)acetamido)-1H-indazol-7-yl)-4-oxo-7-(2,2,3,3-tetrafluoropropoxy)-3,4-dihydropyrido[2,3-d]pyrimidin-2-yl)-2-(3,5-difluorophenyl)ethyl)carbamate (0.35 g, 0.421 mmol, 19%) as a yellow solid, a mixture of diastereomers (atropisomers). LC/MS: m/z=831.95 [M+1]+.

Preparation of (S)-N-((6P)-7-((3P)-2-(1-amino-2-(3,5-difluorophenyl)ethyl)-4-oxo-7-(2,2,3,3-tetrafluoropropoxy)pyrido[2,3-d]pyrimidin-3(4H)-yl)-4-chloro-1-methyl-1H-indazol-3-yl)-N-(methylsulfonyl)acetamide

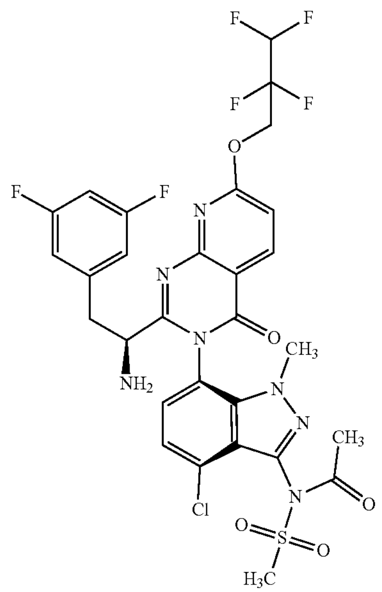

To a solution of tert-butyl (1-(3-(4-chloro-1-methyl-3-(N-(methylsulfonyl)acetamido)-1H-indazol-7-yl)-4-oxo-7-(2,2,3,3-tetrafluoropropoxy)-3,4-dihydropyrido[2,3-d]pyrimidin-2-yl)-2-(3,5-difluorophenyl)ethyl)carbamate (0.48 g, 0.577 mmol) in dichloromethane (2 mL) was added TFA (0.889 mL, 11.54 mmol). The mixture was stirred at rt for 3 h. The resulting pale-yellow solution was concentrated under reduced pressure and the resulting residue was dissolved in EtOAc, washed three times with 1 N NaOH, dried over $Na_2SO_4$ and filtered. The filtrate was concentrated under reduced pressure to afford an oily residue. The residue was subjected to silica gel chromatography (40 g RediSep Gold column) eluting with a gradient of 20-90% Solvent A in hexanes over 5 CV, then eluting with 90% Solvent A in hexanes over 9 CV; Solvent A=ethyl acetate:hexanes:MeOH (9:9:2). Two diastereomers (atropisomers) are separated by this chromatography. Fractions corresponding to the first-eluting diastereomer were pooled and then concentrated in vacuo to afford N-((6P)-7-((3P)-2-(1-amino-2-(3,5-difluorophenyl)ethyl)-4-oxo-7-(2,2,3,3-tetrafluoropropoxy)pyrido[2,3-d]pyrimidin-3(4H)-yl)-4-chloro-1-methyl-1H-indazol-3-yl)-N-(methylsulfonyl)acetamide (0.186 g, 0.254 mmol, 44.0% yield). LC/MS: m/z=731.95 [M+1]+.

Preparation of 2-amino-6-(2,4-difluorophenoxy)nicotinic acid

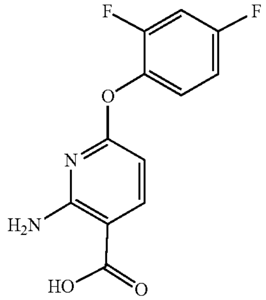 [SMILES: Nc1nc(Oc2ccc(F)cc2F)ccc1C(=O)O]

To a solution of 2,4-difluorophenol (0.765 g, 5.88 mmol) and methyl 2-amino-6-fluoronicotinate (0.5 g, 2.94 mmol) in DMF (15 mL) at rt was added $K_2CO_3$ (1.02 g, 7.35 mmol). The mixture was heated at 80° C. for 18 h. The mixture was cooled to rt and then was quenched by the addition of water. The resulting suspension was filtered and the isolated solids were maintained under active vacuum filtration until the residual solvent was removed to afford methyl 2-amino-6-(2,4-difluorophenoxy)nicotinate as a beige solid. $^1H$ NMR (500 MHz, CHLOROFORM-d) δ ppm 8.12 (d, J=8.64 Hz, 1H) 7.16 (d, J=5.36 Hz, 1H) 6.83-6.96 (m, 2H) 6.22 (d, J=8.64 Hz, 1H) 3.85 (s, 3H). The solids were dissolved in a mixture of Methanol (14.7 mL) and Water (7.35 m). To the solution was added and NaOH (1.2 g, 29.4 mmol) and the mixture was then stirred at rt for 18 h. The reaction mixture was concentrated under reduced pressure to remove methanol. The residual aqueous solution was made acidic (pH<7) by the addition of aq. 0.5 M citric acid. The resulting suspension was filtered, and the isolated solids were maintained under active vacuum filtration until residual solvent was removed. The solids were further dried in the vacuum oven at 50° C. for 18 h to afford 2-amino-6-(2,4-difluorophenoxy)nicotinic acid (0.747 g, 2.81 mmol, 95% yield) as an off-white solid. $^1H$ NMR (500 MHz, DMSO-$d_6$) δ ppm 12.52-12.84 (m, 1H) 8.08 (d, J=8.34 Hz, 1H) 7.39-7.50 (m, 2H) 7.12-7.17 (m, 1H) 6.24 (d, J=8.64 Hz, 1H). LC/MS: m/z=264.95 [M+1]+.

Preparation of tert-butyl (S)-(1-(3-(4-chloro-1-methyl-3-(N-(methylsulfonyl)acetamido)-1H-indazol-7-yl)-7-(2,4-difluorophenoxy)-4-oxo-3,4-dihydropyrido[2,3-d]pyrimidin-2-yl)-2-(3,5-difluorophenyl)ethyl)carbamate

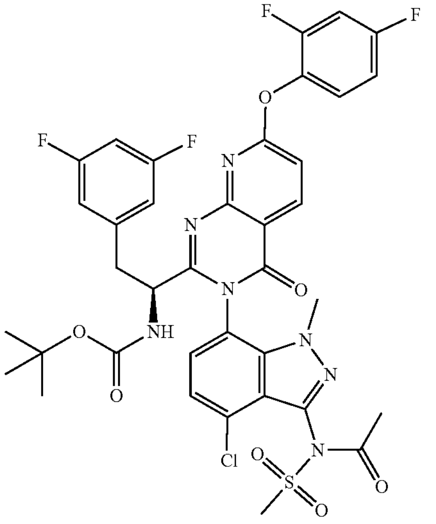 [SMILES: CC(=O)N(c1nn(C)c2c(-n3c([C@H](Cc4cc(F)cc(F)c4)NC(=O)OC(C)(C)C)nc4nc(Oc5ccc(F)cc5F)ccc4c3=O)ccc(Cl)c12)S(C)(=O)=O]

To a suspension of (S)-2-((tert-butoxycarbonyl)amino)-3-(3,5-difluorophenyl)propanoic acid (0.931 g, 3.09 mmol) and 2-amino-6-(2-fluorophenoxy)nicotinic acid (0.697 g, 2.81 mmol) in acetonitrile (16.93 mL) (yellow solution) at −25° C. was added pyridine (1.82 mL, 22.48 mmol) followed by 2,4,6-tripropyl-1,3,5,2,4,6-trioxatriphosphinane 2,4,6-trioxide ("T3P", 50% wt. in EtOAc, 8.4 mL, 14.05 mmol). The reaction mixture (became a clear solution after T3P addition) was stirred as it warmed from −25° C. to 12° C. over 3 h. To the mixture was added N-(7-amino-4-chloro-1-methyl-1H-indazol-3-yl)-N-(methylsulfonyl)acetamide (0.89 g, 2.81 mmol) and the mixture was then stirred for 18 h while warming to rt. The reaction mixture was diluted with ethyl acetate and the resulting mixture was successively washed with 1N NaOH, water, 0.5 M citric acid, and water. The organic phase was dried over $Na_2SO_4$, filtered, and concentrated under reduced pressure. The residue was purified by silica gel chromatography (120 g RediSep Gold column) eluting with 5-80% ethyl acetate in hexanes over 12 CV, then eluting with 80% ethyl acetate in hexanes for 5 CV. The desired fractions were pooled and then concentrated under reduced pressure to afford tert-butyl (1-(3-(4-chloro-1-methyl-3-(N-(methylsulfonyl)acetamido)-1H-indazol-7-yl)-7-(2,4-difluorophenoxy)-4-oxo-3,4-dihydropyrido[2,3-d]pyrimidin-2-yl)-2-(3,5-difluorophenyl)ethyl)carbamate (0.76 g, 0.915 mmol, 32.6% yield) as a yellow solid, a mixture of diastereomers (atropisomers). LC/MS: m/z=830.1 [M+1]+.

Preparation of (S)-N-(7-(2-(1-amino-2-(3,5-difluorophenyl)ethyl)-7-(2,4-difluorophenoxy)-4-oxopyrido[2,3-d]pyrimidin-3(4H)-yl)-4-chloro-1-methyl-1H-indazol-3-yl)-N-(methylsulfonyl)acetamide

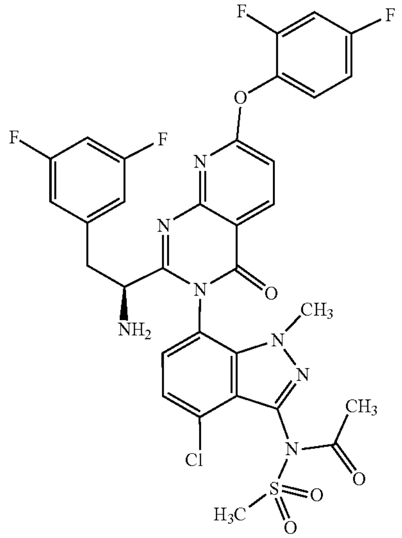 [SMILES: CC(=O)N(c1nn(C)c2c(-n3c([C@@H](N)Cc4cc(F)cc(F)c4)nc4nc(Oc5ccc(F)cc5F)ccc4c3=O)ccc(Cl)c12)S(C)(=O)=O]

To a solution of tert-butyl (S)-(1-(3-(4-chloro-1-methyl-3-(N-(methylsulfonyl)acetamido)-1H-indazol-7-yl)-7-(2,4-difluorophenoxy)-4-oxo-3,4-dihydropyrido[2,3-d]pyrimidin-2-yl)-2-(3,5-difluorophenyl)ethyl)carbamate (0.76 g, 0.915 mmol) in dichloromethane (3.0 mL) was added TFA (1.4 mL, 18.31 mmol). The mixture was stirred at rt for 3 h. The resulting pale-yellow solution was concentrated under reduced pressure and the resulting residue was dissolved in ethyl acetate. The solution was washed three times with 1 N NaOH, dried over $Na_2SO_4$, filtered, and then concentrated under reduced pressure to afford (S)-N-(7-(2-(1-amino-2-(3,5-difluorophenyl)ethyl)-7-(2,4-difluorophenoxy)-4-oxopyrido[2,3-d]pyrimidin-3(4H)-yl)-4-chloro-1-methyl-1H-indazol-3-yl)-N-(methylsulfonyl)acetamide (0.58 g, 0.794 mmol, 87% yield) as an off-white solid. The product, a mixture of atropisomers, was used in the next step without additional purification. LC/MS: m/z=729.95 [M+1]+.

Preparation of 2-amino-6-(2-fluorophenoxy)nicotinic acid

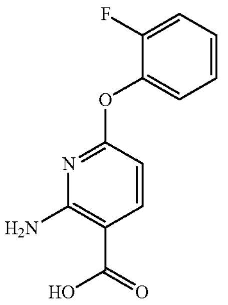 [SMILES: Nc1nc(Oc2ccccc2F)ccc1C(=O)O]

To a solution of 2-fluorophenol (0.659 g, 5.88 mmol) and methyl 2-amino-6-fluoronicotinate (0.5 g, 2.94 mmol) in DMF (15 mL) at rt was added $K_2CO_3$ (1.015 g, 7.35 mmol). The mixture was heated at 80° C. for 4 h then cooled to rt and quenched by the addition of water. The resulting suspension was filtered and the isolated solids were maintained under active vacuum until residue solvent was removed to afford methyl 2-amino-6-(2-fluorophenoxy)nicotinate as a beige solid. The solid was dissolved in Methanol (14.69 ml)/Water (7.35 ml). To the solution was added NaOH (1.2 g, 29.4 mmol) and the mixture was then stirred at rt for 18 h. The mixture was concentrated to remove methanol. The resulting aqueous solution was made acidic (pH<7) by the addition of aq. 0.5 M citric acid. The resulting suspension was filtered, and the isolated solids were maintained under active vacuum filtration until residual solvent was removed. The solids were then dried in a vacuum oven at 50° C. for 18 h to afford 2-amino-6-(2-fluorophenoxy)nicotinic acid (0.694 g, 2.80 mmol, 95% yield) as an off-white solid. $^1$H NMR (500 MHz, DMSO-$d_6$) δ ppm 12.31-13.07 (m, 1H) 8.09 (d, J=8.34 Hz, 1H) 7.24-7.44 (m, 5H) 6.23 (d, J=8.35 Hz, 1H). LC/MS: m/z=248.95 [M+1]+.

Preparation of tert-butyl (S)-(1-(3-(4-chloro-1-methyl-3-(N-(methylsulfonyl)acetamido)-1H-indazol-7-yl)-7-(2-fluorophenoxy)-4-oxo-3,4-dihydropyrido[2,3-d]pyrimidin-2-yl)-2-(3,5-difluorophenyl)ethyl)carbamate

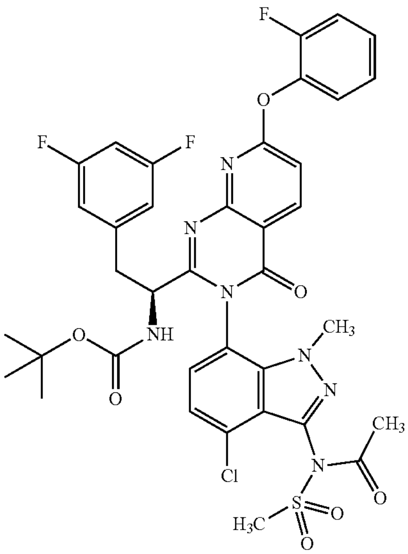 [SMILES: CC(=O)N(c1nn(C)c2c(-n3c([C@H](Cc4cc(F)cc(F)c4)NC(=O)OC(C)(C)C)nc4nc(Oc5ccccc5F)ccc4c3=O)ccc(Cl)c12)S(C)(=O)=O]

To a suspension of (S)-2-((tert-butoxycarbonyl)amino)-3-(3,5-difluorophenyl)propanoic acid (0.931 g, 3.09 mmol) and 2-amino-6-(2,4-difluorophenoxy)nicotinic acid (0.748 g, 2.81 mmol) in acetonitrile (16.93 ml) (yellow solution) at −25° C. was added pyridine (1.82 mL, 22.48 mmol) followed by 2,4,6-tripropyl-1,3,5,2,4,6-trioxatriphosphinane 2,4,6-trioxide ("T3P", 50% wt. in EtOAc, 8.36 mL, 14.05 mmol). The reaction mixture (became a clear solution after T3P addition) was stirred as the temperature rose from −25° C. to 12° C. over 3 h. To the mixture was added N-(7-amino-4-chloro-1-methyl-1H-indazol-3-yl)-N-(methylsulfonyl)acetamide (0.89 g, 2.81 mmol) and the mixture was then stirred for 18 h while warming to rt. The reaction mixture was diluted with ethyl acetate, then washed successively with aq. 1N NaOH, water, aq. 0.5 M citric acid, and water. The organic layer was dried over $Na_2SO_4$, filtered, and then concentrated under reduced pressure. The residue was purified by silica gel chromatography (120 g RediSep Gold column) eluting with 5-80% EtOAc in hexanes over 12 CV, then eluting with 80% EtOAc in hexanes for 5 CV. The desired fractions were pooled and concentrated under reduced pressure to afford tert-butyl (1-(3-(4-chloro-1-methyl-3-(N-(methylsulfonyl)acetamido)-1H-indazol-7-yl)-7-(2-fluorophenoxy)-4-oxo-3,4-dihydropyrido[2,3-d]pyrimidin-2-yl)-2-(3,5-difluorophenyl)ethyl)carbamate (0.645 g, 0.794 mmol, 28.3% yield) as a yellow solid. LC/MS: m/z=811.1 [M]+.

(S)-N-(7-(2-(1-amino-2-(3,5-difluorophenyl)ethyl)-7-(2-fluorophenoxy)-4-oxopyrido[2,3-d]pyrimidin-3(4H)-yl)-4-chloro-1-methyl-1H-indazol-3-yl)-N-(methylsulfonyl)acetamide

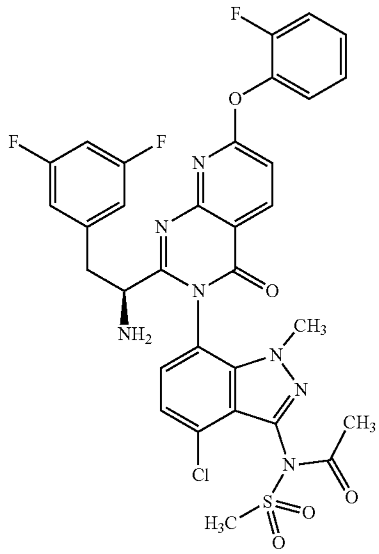 [SMILES: CC(=O)N(c1nn(C)c2c(-n3c([C@@H](N)Cc4cc(F)cc(F)c4)nc4nc(Oc5ccccc5F)ccc4c3=O)ccc(Cl)c12)S(C)(=O)=O]

To a solution of tert-butyl (S)-(1-(3-(4-chloro-1-methyl-3-(N-(methylsulfonyl)acetamido)-1H-indazol-7-yl)-7-(2-fluorophenoxy)-4-oxo-3,4-dihydropyrido[2,3-d]pyrimidin-2-yl)-2-(3,5-difluorophenyl)ethyl)carbamate (0.64 g, 0.788 mmol) in dichloromethane (2.6 mL) was added TFA (1.2 mL, 15.76 mmol). The mixture was stirred at rt for 3 h. The resulting pale-yellow solution was concentrated under reduced pressure and the residue was then dissolved in EtOAc. The solution was washed three times with 1 N NaOH, then was dried over $Na_2SO_4$, filtered, and concentrated under reduced pressure to afford an oily residue. The residue was subjected to silica gel chromatography (40 g RediSep Gold column) by eluting with a gradient of 10-80% Solvent A in hexanes over 7 CV, then eluting with 80% Solvent A in hexanes over 11 CV; Solvent A=of a 9:9:2 of ethyl acetate:hexanes:MeOH. All fractions containing the desired product mass were pooled and then concentrated under reduced pressure to afford (S)-N-(7-(2-(1-amino-2-(3,5-difluorophenyl)ethyl)-7-(2-fluorophenoxy)-4-oxopyrido[2,3-d]pyrimidin-3(4H)-yl)-4-chloro-1-methyl-1H-indazol-3-yl)-N-(methylsulfonyl)acetamide (0.45 g, 0.632 mmol, 80% yield). The product is a mixture of diastereomers (atropisomers) which was used without further purification in the next step. LC/MS: m/z=711.1 [M]+.

Preparation of 2-amino-6-(benzyloxy)nicotinic acid

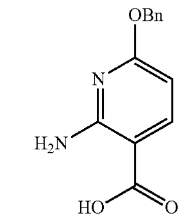 [SMILES: Nc1nc(OCc2ccccc2)ccc1C(=O)O]

A solution of 2-amino-6-chloronicotinic acid (5 g, 29 mmol) and potassium tert-butoxide (9.75 g, 87 mmol) in benzyl alcohol (97 mL) was heated to 120° C. for 3 h. After cooling to ambient temperature, the very dark reaction mixture was added to water and washed with ether (×3). The aqueous layer was then acidified with 0.5 M citric acid. The tan precipitate filtered to provide the product (4.4 g, 62%) which was used in the next reaction without further purification. $^{1}H$ NMR (500 MHz, DMSO-$d_6$) δ 12.40 (br s, 1H), 7.94 (d, J=8.55 Hz, 1H), 7.06-7.52 (m, 5H), 6.04 (d, J=8.24 Hz, 1H), 5.33 (s, 2H). LC/MS: m/z=245.15 [M+1]+.

Preparation of N-[(6P)-7-{2-[(1S)-1-amino-2-(3,5-difluorophenyl)ethyl]-7-hydroxy-4-oxo-3H,4H-pyrido[2,3-d]pyrimidin-3-yl}-4-chloro-1-methyl-1H-indazol-3-yl]-N-[(4-methoxyphenyl)methyl]methanesulfonamide Scheme

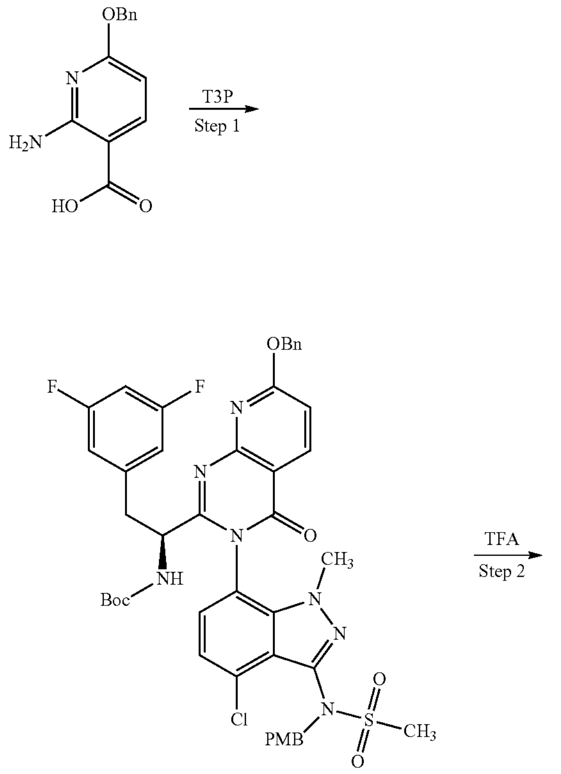

-continued

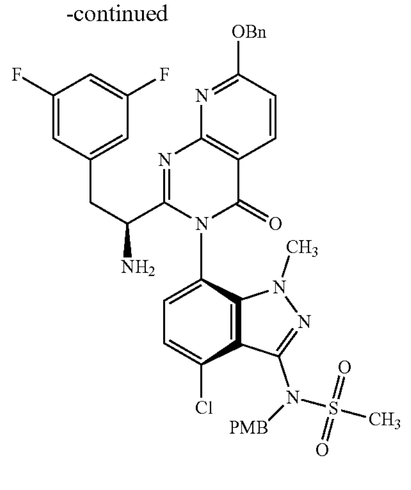

Step 1:

To a suspension of (S)-2-((tert-butoxycarbonyl)amino)-3-(3,5-difluorophenyl)propanoic acid (5.49 g, 18.23 mmol) and 2-amino-6-(benzyloxy)nicotinic acid (4.45 g, 18.23 mmol) in acetonitrile (92 mL) (yellow solution) at −25° C. was added pyridine (9.83 mL, 122 mmol) followed by 2,4,6-tripropyl-1,3,5,2,4,6-trioxatriphosphinane 2,4,6-trioxide ("T3P", 45.2 ml, 76 mmol). The reaction mixture (became a clear solution after $T_3P$ addition) was stirred at −25° C. to 10° C. over 4.5 h, then N-(7-amino-4-chloro-1-methyl-1H-indazol-3-yl)-N-(4-methoxybenzyl)methanesulfonamide (6 g, 15.19 mmol) was added and the mixture was stirred for 18 h while warming to rt. The reaction mixture was diluted with ethyl acetate, washed with 1N NaOH, then water, then 0.5 M citric acid, then water, then dried over $Na_2SO_4$ and concentrated in vacuo. The resulting residue was purified on silica (330 g RediSep Gold column) using 0-60% ethyl acetate in hexanes over 15 CV, then holding at 60% EtOAc for 10 CV. The desired fractions were pooled and concentrated to afford a pale yellow solid (8.1 g, 9.14 mmol, 60.1% yield), a mixture of tert-butyl N-[(1S)-1-[(3P,3P)-7-(benzyloxy)-3-(4-chloro-3-{N-[(4-methoxyphenyl)methyl]methanesulfonamido}-1-methyl-1H-indazol-7-yl)-4-oxo-3H,4H-pyrido[2,3-d]pyrimidin-2-yl]-2-(3,5-difluorophenyl)ethyl]carbamate (major) and tert-butyl N-[(1S)-1-[(3M,3M)-7-(benzyloxy)-3-(4-chloro-3-{N-[(4-methoxyphenyl)methyl]methanesulfonamido}-1-methyl-1H-indazol-7-yl)-4-oxo-3H,4H-pyrido[2,3-d]pyrimidin-2-yl]-2-(3,5-difluorophenyl)ethyl]carbamate (minor). LC/MS: m/z=886.25 [M+1]+.

Step 2:

TFA (21.1 mL, 274 mmol) was added to a solution of tert-butyl (S)-(1-(7-(benzyloxy)-3-(4-chloro-3-(N-(4-methoxybenzyl)methylsulfonamido)-1-methyl-1H-indazol-7-yl)-4-oxo-3,4-dihydropyrido[2,3-d]pyrimidin-2-yl)-2-(3,5-difluorophenyl)ethyl)carbamate (Product from Step 1, 8.1 g, 9.14 mmol) in dichloromethane (45.7 mL). The mixture was stirred at rt for 2 h. The resultant pale-yellow solution was concentrated. The residue was taken up in ethyl acetate, then washed three times with 1 N NaOH, then dried over $Na_2SO_4$ and then concentrated in vacuo to afford an oily residue. The residue was purified on silica gel (330 g RediSep Gold column) by a gradient method of Solvent A:Solvent B 65:35→0:100 (2 CV), then 0:100 (9 CV); Solvent A=hexanes; Solvent B=9:9:2 hexanes:ethyl acetate:MeOH. The first eluting isomer (major) was collected and concentrated in vacuo to afford N-[(6P)-7-{2-[(1S)-1-amino-2-(3,5-difluorophenyl)ethyl]-7-hydroxy-4-oxo-3H, 4H-pyrido[2,3-d]pyrimidin-3-yl}-4-chloro-1-methyl-1H-indazol-3-yl]-N-[(4-methoxyphenyl)methyl] methanesulfonamide (4.1 g, 5.89 mmol, 64.5% yield). $^1H$ NMR (500 MHz, DMSO-$d_6$) δ 7.86-7.98 (m, 1H) 7.15-7.37 (m, 4H) 6.97-7.06 (m, 1H) 6.70-6.89 (m, 4H) 6.40-6.48 (m, 1H) 4.70-4.88 (m, 2H) 3.41-3.81 (m, 7H) 3.20-3.28 (m, 1H) 3.08-3.12 (m, 3H) 2.71-2.79 (m, 1H) 1.69-2.00 (m, 2H). LC/MS: m/z=696.20 [M+1]+.

Preparation of N-((S)-1-((3P)-3-(4-chloro-3-(N-(4-methoxybenzyl)methylsulfonamido)-1-methyl-1H-indazol-7-yl)-7-hydroxy-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

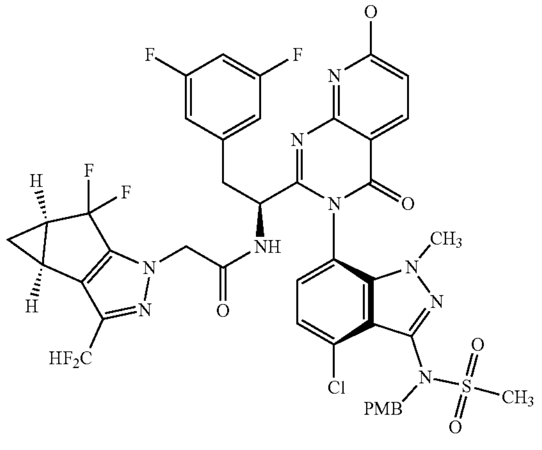

To a stirred solution of N-[(6P)-7-{2-[(1S)-1-amino-2-(3,5-difluorophenyl)ethyl]-7-hydroxy-4-oxo-3H,4H-pyrido[2,3-d]pyrimidin-3-yl}-4-chloro-1-methyl-1H-indazol-3-yl]-N-[(4-methoxyphenyl)methyl]methanesulfonamide (0.926 g, 1.330 mmol) in DMF (13 ml) was added 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (0.351 g, 1.330 mmol), 2-(3H-[1,2,3]triazolo[4,5-b]pyridin-3-yl)-1,1,3,3-tetramethylisouronium hexafluorophosphate (V) ("HATU", 0.531 g, 1.397 mmol), and DIPEA (0.581 ml, 3.33 mmol). The reaction mixture was stirred for 2 h after which the reaction mixture was diluted with water and extracted with ethyl acetate. The combined EtOAc extractions were washed with brine, dried over $Na_2SO_4$, and concentrated in vacuo. The crude product was purified via silica gel flash chromatography using 10-100% ethyl acetate in hexanes to provide N-((S)-1-((3P)-3-(4-chloro-3-(N-(4-methoxybenzyl)methylsulfonamido)-1-methyl-1H-indazol-7-yl)-7-hydroxy-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (1.1 g, 88%) as an off-white foamy solid. LC/MS: m/z=942.25 $[M+1]^+$.

N-(7-amino-4-chloro-1-methyl-1H-indazol-3-yl)-N-(methylsulfonyl)acetamide was prepared according to the scheme below:

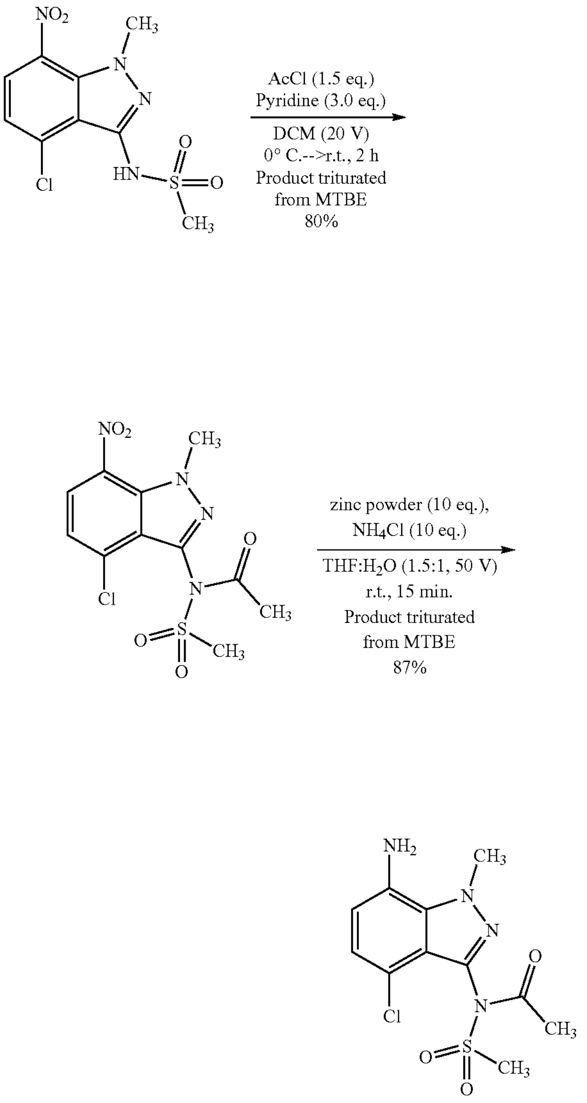

N-((S)-1-((3P)-3-(4-chloro-1-methyl-3-(N-(methylsulfonyl)acetamido)-1H-indazol-7-yl)-7-hydroxy-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide was prepared following the procedure used to prepare N-((S)-1-((3P)-3-(4-chloro-3-(N-(4-methoxybenzyl)methylsulfonamido)-1-methyl-1H-indazol-7-yl)-7-hydroxy-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide but substituting N-(7-amino-4-chloro-1-methyl-1H-indazol-3-yl)-N-(methylsulfonyl)acetamide for N-(7-amino-4-chloro-1-methyl-1H-indazol-3-yl)-N-(4-methoxybenzyl) methanesulfonamide.

Preparation of methyl 2-amino-6-(2,2,3,3,4,4,4-heptafluorobutoxy)nicotinate

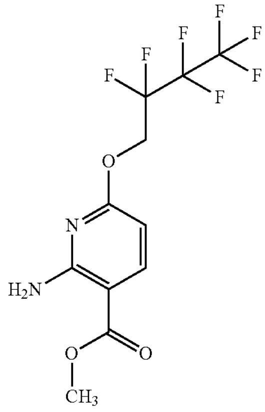 [SMILES: COC(=O)c1ccc(OCC(F)(F)C(F)(F)C(F)(F)F)nc1N]

To a cooled (ice/water bath) solution of 2,2,3,3,4,4,4-heptafluorobutan-1-ol (3.82 g, 19.10 mmol) in N,N-Dimethylformamide (38.2 mL) was added NaH (60% dispersion in oil, 1.222 g, 30.6 mmol). The mixture was stirred under an atmosphere of nitrogen for 25 min. To the mixture was added a solution of methyl 2-amino-6-fluoronicotinate (1.3 g, 7.64 mmol) in N,N-dimethylformamide (10 mL). The reaction mixture was allowed to warm to r.t. with stirring for 18 h. The reaction mixture was then quenched by the addition of water. The mixture was extracted with ethyl acetate and the organic solution was washed with water and then brine. The organic solution was dried over $Na_2SO_4$, filtered, and concentrated under reduced pressure. The resulting residue was subjected to silica gel chromatography (120 g RediSep Gold column) eluting with 0-30% ethyl acetate in hexanes over 15 CV. Fractions containing the desired product were pooled and then concentrated under reduced pressure to afford methyl 2-amino-6-(2,2,3,3,4,4,4-heptafluorobutoxy)nicotinate (0.845 g, 2.413 mmol, 31.6% yield) as a yellow oil. $^1$H NMR (500 MHz, CHLOROFORM-d) δ ppm 8.06 (d, J=8.64 Hz, 1H) 6.15 (d, J=8.35 Hz, 1H) 4.72-4.98 (m, 2H) 3.75-3.95 (m, 3H). LC/MS: m/z=350.85 [M+1]+.

Preparation of 2-Amino-6-(2,2,3,3,4,4,4-heptafluorobutoxy)nicotinic acid

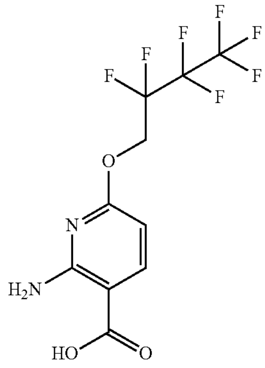 [SMILES: Nc1nc(OCC(F)(F)C(F)(F)C(F)(F)F)ccc1C(=O)O]

To a solution of methyl 2-amino-6-(2,2,3,3,4,4,4-heptafluorobutoxy)nicotinate (0.845 g, 2.413 mmol) in methanol (10 mL) at rt was added and aqueous solution of NaOH (10 N, 3.62 mL, 36.2 mmol) upon which an exotherm was noted. The cloudy reaction mixture was allowed to cool to rt with stirring overnight. The mixture was concentrated under reduced pressure. The resulting residue was dissolved in water, washed with ether, and then adjusted to pH<7 by the addition of aq. 0.5 M citric acid. The solids were collected by filtration and then maintained under active vacuum filtration until residual solvent was removed. The solids were then dried in a vacuum oven at 45° C. for 18 h to afford 2-amino-6-(2,2,3,3,4,4,4-heptafluorobutoxy)nicotinic acid (0.777 g, 2.311 mmol, 96% yield) as a light yellow solid. 1H NMR (500 MHz, DMSO-$d_6$) δ ppm 12.15-13.24 (m, 1H) 8.02 (d, J=8.34 Hz, 1H) 7.02-7.73 (m, 2H) 6.11 (d, J=8.64 Hz, 1H) 5.11 (t, J=14.31 Hz, 2H). LC/MS: m/z=336.9 [M+1]+.

Preparation of tert-butyl (S)-(1-(3-(4-chloro-1-methyl-3-(N-(methylsulfonyl)acetamido)-1H-indazol-7-yl)-7-(2,2,3,3,4,4,4-heptafluorobutoxy)-4-oxo-3,4-dihydropyrido[2,3-d]pyrimidin-2-yl)-2-(3,5-difluorophenyl)ethyl)carbamate

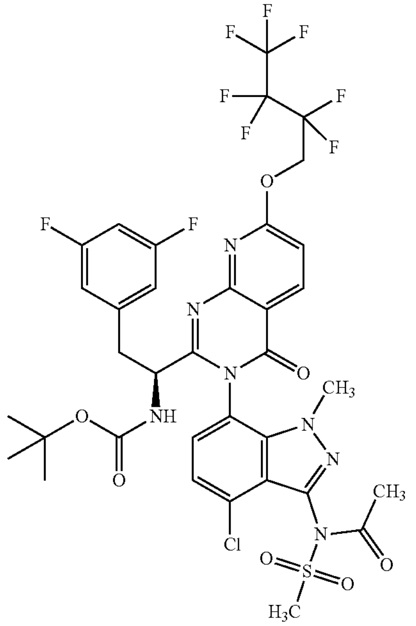 [SMILES: CC(=O)N(c1nn(C)c2c(-n3c([C@H](Cc4cc(F)cc(F)c4)NC(=O)OC(C)(C)C)nc4nc(OCC(F)(F)C(F)(F)C(F)(F)F)ccc4c3=O)ccc(Cl)c12)S(C)(=O)=O]

To a suspension of (S)-2-((tert-butoxycarbonyl)amino)-3-(3,5-difluorophenyl)propanoic acid (0.691 g, 2.292 mmol) and 2-amino-6-(2,2,3,3,4,4,4-heptafluorobutoxy)nicotinic acid (0.770 g, 2.292 mmol) in acetonitrile (12.55 mL) (yellow solution) at −25° C. was added pyridine (1.348 ml, 16.67 mmol) followed by 2,4,6-tripropyl-1,3,5,2,4,6-trioxatriphosphinane 2,4,6-trioxide ("T3P", 50% wt. solution in EtOAc, 3.10 mL, 10.42 mmol). The reaction mixture (became a clear solution after T3P addition) warmed from −25° C. to 12° C. with stirring over 5 h. To the mixture was added N-(7-amino-4-chloro-1-methyl-1H-indazol-3-yl)-N-(methylsulfonyl)acetamide (0.66 g, 2.084 mmol). The mixture was allowed to warm to rt with stirring for 18 h. The reaction mixture was diluted with water, then the pH was adjusted to pH 10 by the addition of aq. 1 N NaOH. The mixture was extracted with ethyl acetate and the organic layer was successively washed with water, 0.5N citric acid, and water. The organic solution was dried over $Na_2SO_4$ and then was concentrated under reduced pressure. The residue was subjected to silica gel chromatography (220 g RediSep Gold column) eluting with 0-60% ethyl acetate in hexanes over 15 CV, then eluting with 60% ethyl acetate in hexanes for 5 CV. Fractions containing the desired product were pooled and then concentrated under reduced pressure to afford tert-butyl (S)-(1-(3-(4-chloro-1-methyl-3-(N-(methylsulfonyl)acetamido)-1H-indazol-7-yl)-7-(2,2,3,3,4,4,4-heptafluorobutoxy)-4-oxo-3,4-dihydropyrido[2,3-d]pyrimidin-2-yl)-2-(3,5-difluorophenyl)ethyl)carbamate (0.44 g, 0.489 mmol, 23.46% yield) as a light pink solid. LC/MS: m/z=899.95 [M+1]+.

Preparation of (S)-N-(7-(2-(1-amino-2-(3,5-difluorophenyl)ethyl)-7-(2,2,3,3,4,4,4-heptafluorobutoxy)-4-oxopyrido[2,3-d]pyrimidin-3(4H)-yl)-4-chloro-1-methyl-1H-indazol-3-yl)-N-(methylsulfonyl) acetamide

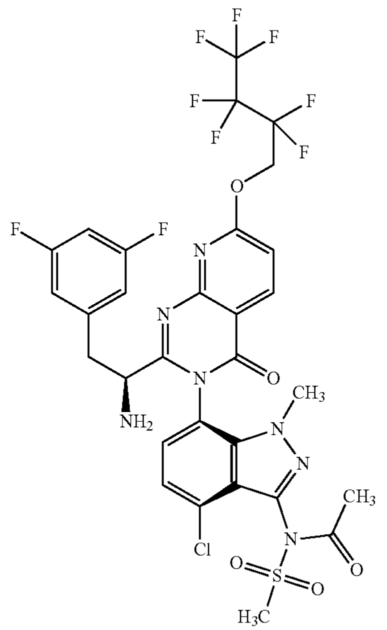

To a solution of tert-butyl (S)-(1-(3-(4-chloro-1-methyl-3-(N-(methylsulfonyl)acetamido)-1H-indazol-7-yl)-7-(2,2,3,3,4,4,4-heptafluorobutoxy)-4-oxo-3,4-dihydropyrido[2,3-d]pyrimidin-2-yl)-2-(3,5-difluorophenyl)ethyl)carbamate (0.44 g, 0.489 mmol) in dichloromethane (4.89 mL) was added TFA (0.753 mL, 9.78 mmol). The mixture was stirred at rt for 3 h. The reaction mixture was concentrated under reduced pressure and the residue was dissolved in EtOAc. The solution was washed with 1 N NaOH, dried over $Na_2SO_4$ and then concentrated under reduced pressure to afford a yellow solid. This material was subjected to silica gel chromatography (80 g RediSep Gold column) eluting with a gradient of 30-100% Solvent A in hexanes over 3 CV, then eluting with 100% Solvent A for 9 CV; Solvent A=ethyl acetate:hexanes:MeOH (9:9:2). Fractions containing the desired product were pooled and then concentrated under reduced pressure to afford (S)-N-(7-(2-(1-amino-2-(3,5-difluorophenyl)ethyl)-7-(2,2,3,3,4,4,4-heptafluorobutoxy)-4-oxopyrido[2,3-d]pyrimidin-3(4H)-yl)-4-chloro-1-methyl-1H-indazol-3-yl)-N-(methylsulfonyl)acetamide (0.244 g, 0.305 mmol, 62.4% yield). LC/MS: m/z=799.95 [M+1]+. The product, a mixture of diastereomers (atropisomers), was used in the next step without additional purification.

Preparation of methyl 2-amino-6-((2,2,3,3,4,4,5,5,5-nonafluoropentyl)oxy)nicotinate

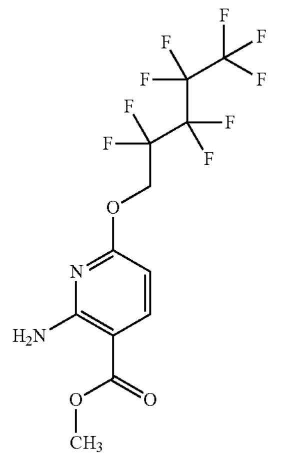 [SMILES: COC(=O)c1ccc(OCC(F)(F)C(F)(F)C(F)(F)C(F)(F)F)nc1N]

To an ice-cold solution of 2,2,3,3,4,4,5,5,5-nonafluoropentan-1-ol (1.940 g, 7.76 mmol) in N,N-Dimethylformamide (70.5 mL) was added NaH (60% dispersion in oil, 0.564 g, 14.11 mmol). The mixture was stirred under an atmosphere of nitrogen for 25 min. To the mixture was added a solution of methyl 2-amino-6-fluoronicotinate (1.2 g, 7.05 mmol) in N,N-dimethylformamide (10 mL). The reaction mixture was stirred for 3 h and then quenched by the addition of water. The mixture was warmed to room temperature and then extracted with ethyl acetate. The organic solution was wash with water and then brine, dried over $Na_2SO_4$ and then concentrated under reduced pressure. The resulting residue was subjected to silica gel chromatography (120 g RediSep Gold column) eluting with 0-30% ethyl acetate in hexanes over 15 CV. Fractions containing the pure desired product were pooled and then concentrated under reduced pressure to afford methyl 2-amino-6-((2,2,3,3,4,4,5,5,5-nonafluoropentyl)oxy)nicotinate (1.35 g, 3.37 mmol, 47.8% yield) as a yellow oil. 1H NMR (500 MHz, CHLOROFORM-d) δ ppm 8.06 (d, J=8.34 Hz, 1H) 6.15 (d, J=8.35 Hz, 1H) 4.75-4.95 (m, 2H) 3.78-3.91 (m, 3H). LC/MS: m/z=400.95 [M+1]+.

Preparation of 2-Amino-6-((2,2,3,3,4,4,5,5,5-nonafluoropentyl)oxy)nicotinic acid

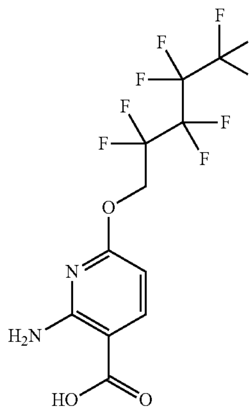

To a solution of methyl 2-amino-6-((2,2,3,3,4,4,5,5,5-nonafluoropentyl)oxy)nicotinate (1.35 g, 3.37 mmol) in methanol (11.24 mL)/water (5.62 mL) at RT was added sodium hydroxide (1.349 g, 33.7 mmol) upon which an exotherm was noted. The cloudy reaction mixture was allowed to cool to RT with stirring overnight. The mixture was concentrated under reduced pressure and the resulting residue was dissolved in water. The pH was adjusted to pH<7 by the addition of aq. 0.5 M citric acid. The resulting solids were collected by filtration and then maintained under active vacuum filtration until residual solvent was removed (18 h) to afford 2-amino-6-((2,2,3,3,4,4,5,5,5-nonafluoropentyl)oxy)nicotinic acid (1.13 g, 2.93 mmol, 87% yield) as a pale yellow solid. 1H NMR (500 MHz, DMSO-$d_6$) δ ppm 11.82-13.26 (m, 1H) 8.02 (d, J=8.34 Hz, 1H) 7.17-7.68 (m, 2H) 6.11 (d, J=8.34 Hz, 1H) 5.13 (t, J=14.45 Hz, 2H). LC/MS: m/z=386.95 [M+1]+.

Preparation of tert-Butyl (S)-(1-(3-(4-chloro-1-methyl-3-(N-(methylsulfonyl)acetamido)-1H-indazol-7-yl)-7-((2,2,3,3,4,4,5,5,5-nonafluoropentyl)oxy)-4-oxo-3,4-dihydropyrido[2,3-d]pyrimidin-2-yl)-2-(3,5-difluorophenyl)ethyl)carbamate

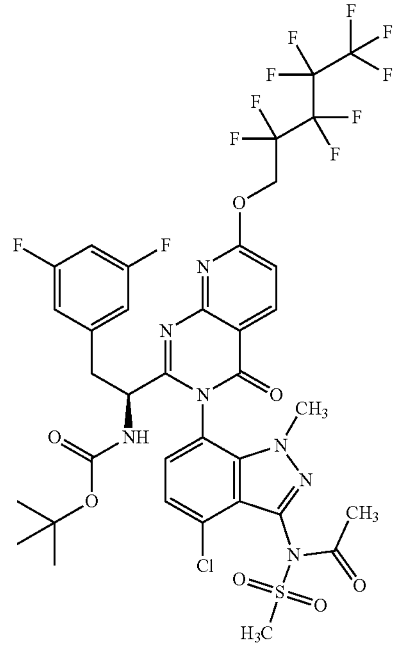 [SMILES: CC(=O)N(c1nn(C)c2c(-n3c([C@H](Cc4cc(F)cc(F)c4)NC(=O)OC(C)(C)C)nc4nc(OCC(F)(F)C(F)(F)C(F)(F)C(F)(F)F)ccc4c3=O)ccc(Cl)c12)S(C)(=O)=O]

To a suspension of (S)-2-((tert-butoxycarbonyl)amino)-3-(3,5-difluorophenyl)propanoic acid (0.502 g, 1.667 mmol) and 2-amino-6-((2,2,3,3,4,4,5,5,5-nonafluoropentyl)oxy)nicotinic acid (0.644 g, 1.667 mmol) in acetonitrile (9.13 mL) (yellow solution) at −25° C. was added pyridine (0.981 mL, 12.12 mmol) followed by 2,4,6-tripropyl-1,3,5,2,4,6-trioxatriphosphinane 2,4,6-trioxide ("$T_3P$", 50% wt. in EtOAc, 4.69 mL, 7.58 mmol). The reaction mixture (became a clear solution after T3P addition) warmed from −25° C. to 12° C. with stirring over 5 h. To the mixture was added N-(7-amino-4-chloro-1-methyl-1H-indazol-3-yl)-N-(methylsulfonyl)acetamide (0.48 g, 1.515 mmol). The mixture was allowed to warm to RT with stirring for 18 h. The reaction mixture was diluted with water and the pH was then adjusted to pH 10 by the addition of aq. 1N NaOH. The mixture was extracted with ethyl acetate and the organic solution was successively washed with water, 0.5 N citric acid, and water. The organic solution was dried over $Na_2SO_4$ and then concentrated under reduced pressure. The resulting residue was subjected to silica gel chromatography (120 g RediSep Gold column) eluting with 0-65% ethyl acetate in hexanes over 15 CV. Fractions containing the pure desired product were pooled and then concentrated under reduced pressure to afford tert-butyl (S)-(1-(3-(4-chloro-1-methyl-3-(N-(methylsulfonyl)acetamido)-1H-indazol-7-yl)-7-((2,2,3,3,4,4,5,5,5-nonafluoropentyl)oxy)-4-oxo-3,4-dihydropyrido[2,3-d]pyrimidin-2-yl)-2-(3,5-difluorophenyl)ethyl) carbamate (0.14 g, 0.147 mmol, 9.72% yield) as a yellow solid. LC/MS: m/z=949.95 [M+1]+.

Preparation of (S)-N-(7-(2-(1-amino-2-(3,5-difluorophenyl)ethyl)-7-((2,2,3,3,4,4,5,5,5-nonafluoropentyl)oxy)-4-oxopyrido[2,3-d]pyrimidin-3(4H)-yl)-4-chloro-1-methyl-1H-indazol-3-yl)-N-(methylsulfonyl)acetamide

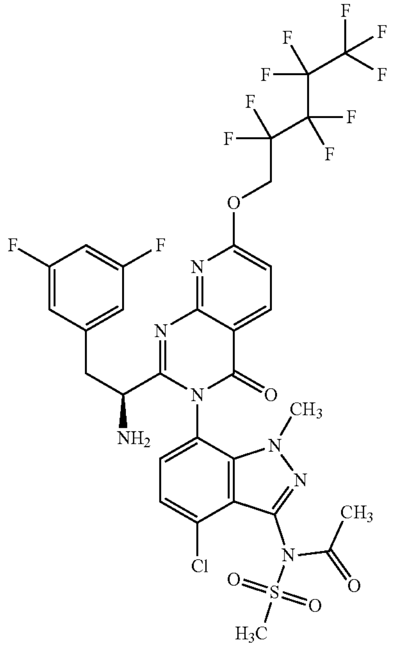 [SMILES: CC(=O)N(c1nn(C)c2c(-n3c([C@@H](N)Cc4cc(F)cc(F)c4)nc4nc(OCC(F)(F)C(F)(F)C(F)(F)C(F)(F)F)ccc4c3=O)ccc(Cl)c12)S(C)(=O)=O]

To a solution of tert-butyl (S)-(1-(3-(4-chloro-1-methyl-3-(N-(methylsulfonyl)acetamido)-1H-indazol-7-yl)-7-((2,2,3,3,4,4,5,5,5-nonafluoropentyl)oxy)-4-oxo-3,4-dihydro-pyrido[2,3-d]pyrimidin-2-yl)-2-(3,5-difluorophenyl)ethyl) carbamate (0.14 g, 0.147 mmol) in dichloromethane (1 mL) was added trifluoroacetic acid (0.5 mL). The solution was stirred at RT for 2.5 h. The reaction mixture was concentrated under reduced pressure and the resulting residue was dissolved in EtOAc. The solution was washed with aq. 1 N NaOH, dried over $Na_2SO_4$ and concentrated to afford (S)-N-(7-(2-(1-amino-2-(3,5-difluorophenyl)ethyl)-7-((2,2,3,3,4,4,5,5,5-nonafluoropentyl)oxy)-4-oxopyrido[2,3-d]pyrimidin-3(4H)-yl)-4-chloro-1-methyl-1H-indazol-3-yl)-N-(methylsulfonyl)acetamide (0.133 g, 0.156 mmol, quantitative yield) as a yellow solid. The material, a mixture of diastereomers (atropisomers) was used in the next step without additional purification.

Preparation of 2-((3bS,4aR)-3-cyclopropyl-5,5-difluoro-3b,4,4a,5-tetrahydro-1H-cyclopropa[3,4]cyclopenta[1,2-c]pyrazol-1-yl)acetic acid and 2-((3bR,4aS)-3-cyclopropyl-5,5-difluoro-3b,4,4a,5-tetrahydro-1H-cyclopropa[3,4]cyclopenta[1,2-c]pyrazol-1-yl)acetic acid

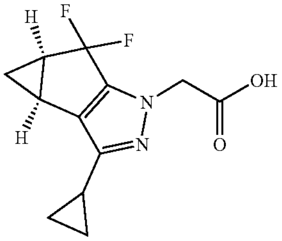

and

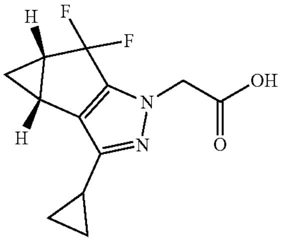

The title compounds were prepared following the route and procedures used to prepare 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid and 2-((3bR,4aS)-3-(difluoromethyl)-5,5-difluoro-3b,4,4a,5-tetrahydro-1H-cyclopropa[3,4]cyclopenta[1,2-c]pyrazol-1-yl)acetic acid but substituting cyclopropanecarbonyl chloride for ethyldifluoroacetate. The route is depicted in the scheme below.

Synthesis Scheme

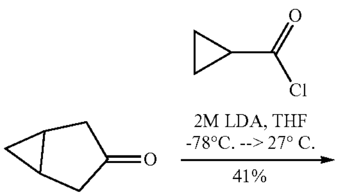

-continued

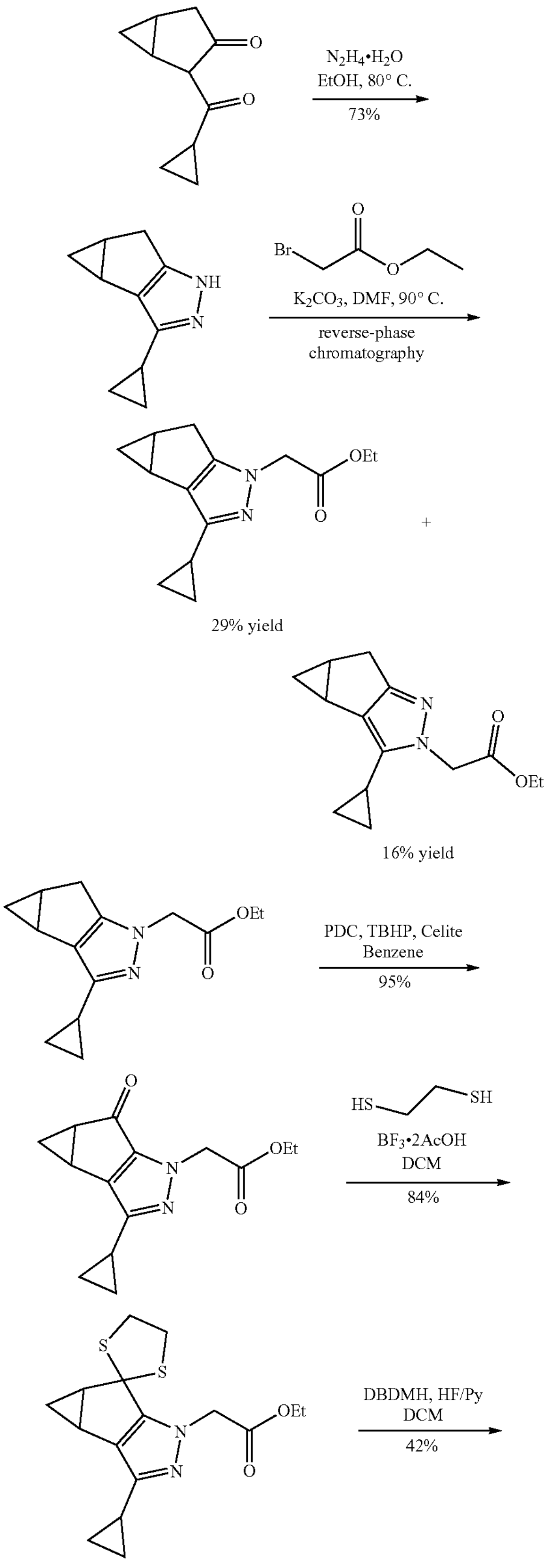

-continued

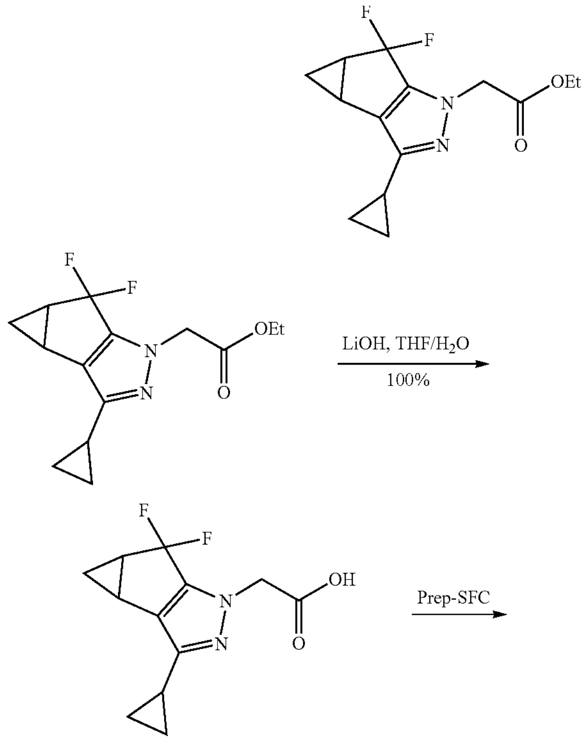

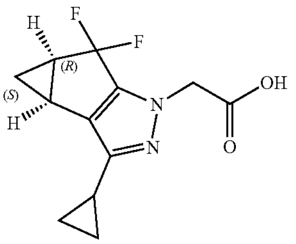

+

33% yield
2-((3bS,4aR)-3-cyclopropyl-5,5-difluoro-3b,4,4a,5-tetrahydro-1H-cyclopropa[3,4]cyclopenta[1,2-c]pyrazol-1-yl)acetic acid

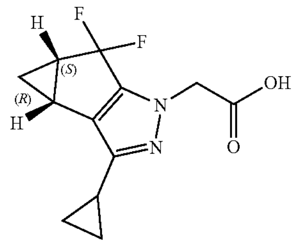

33% yield
2-((3bR,4aS)-3-cyclopropyl-5,5-difluoro-3b,4,4a,5-tetrahydro-1H-cyclopropa[3,4]cyclopenta[1,2-c]pyrazol-1-yl)acetic acid Preparation of 2-((3bS,4aS)-3-cyclopropyl-3b,4,4a,5-tetrahydro-1H-cyclopropa[3,4]cyclopenta[1,2-c]pyrazol-1-yl)acetic acid and 2-((3bR,4aR)-3-cyclopropyl-3b,4,4a,5-tetrahydro-1H-cyclopropa[3,4]cyclopenta[1,2-c]pyrazol-1-yl)acetic acid

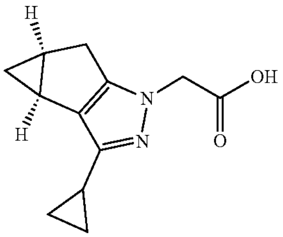

and

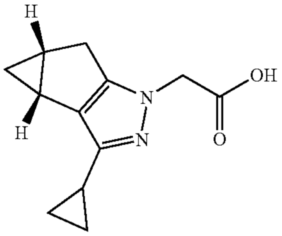

The title compounds were prepared according to the scheme below.

Synthesis Scheme

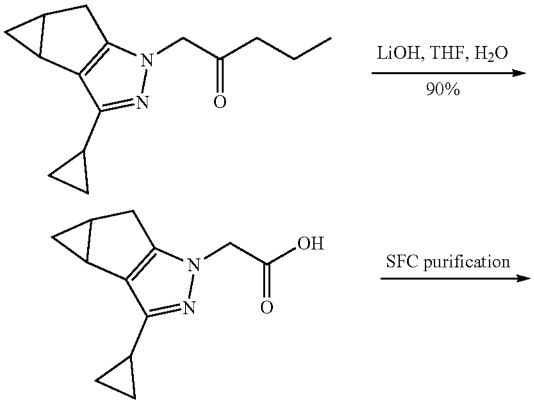

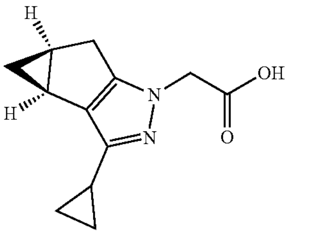

+

21% yield
2-((3bS,4aS)-3-cyclopropyl-3b,4,4a,5-tetrahydro-1H-cyclopropa[3,4]cyclopenta[1,2-c]pyrazol-1-yl)acetic acid -continued

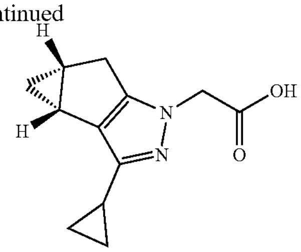

33% yield
2-((3bR,4aS)-3-cyclopropyl-3b,4,4a,5-tetrahydro-1H-cyclopropa[3,4]cyclopenta[1,2-c]pyrazol-1-yl)acetic acid General Synthesis Methods:

General Procedure A:

To a mixture of N-((S)-1-((3P)-3-(4-chloro-1-methyl-3-(N-(methylsulfonyl)acetamido)-1H-indazol-7-yl)-7-hydroxy-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (0.05 g, 0.058 mmol), the indicated alcohol (3 equiv.) and triphenylphosphine (3.2 equiv.) in THE (1 mL) was added dropwise a solution of diisopropyl (E)-diazene-1,2-dicarboxylate (3 equiv.) in THE (0.1 mL). The reaction mixture was stirred for 18 h at rt. To the solution was added ammonia in methanol (2M, 1 mL). The mixture was concentrated under reduced pressure. The resulting residue was dissolved in DMF (2 mL), filtered, and the filtrate was subjected to HPLC purification to afford the indicated product.

General Procedure B:

To a mixture of N-((S)-1-((3P)-3-(4-chloro-3-(N-(4-methoxybenzyl)methylsulfonamido)-1-methyl-1H-indazol-7-yl)-7-hydroxy-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (0.032-0.035 mmol, 1 equiv.), the indicated alcohol (3 equiv.) and triphenylphosphine (3.2 equiv.) in THE (0.8 mL) was added dropwise a solution of diisopropyl (E)-diazene-1,2-dicarboxylate (3 equiv.) in THE (0.2 mL). The reaction mixture was stirred for 18 h at rt and then the reaction mixture was concentrated in vacuo. The residue was taken up in DCM (0.5 ml):TFA (0.25 mL) and to the solution was added triflic acid (3 equiv.). The resulting purple solution was stirred for 1 h; concentrated in vacuo; taken up in ethyl acetate (1.5 mL); and washed with sat. aq. $NaHCO_3$(1 mL). The organic layer was isolated and concentrated. The residue was dissolved in DMF; filtered; and then subjected to HPLC purification to afford the indicated product.

HPLC Purification:

HPLC purification was performed using one of the conditions indicated below, optionally followed by a second HPLC purification using a different condition indicated below. Based on analytical HPLC data obtained on the crude reaction mixture, the purification condition was optimized for each target compound by modifying the initial Solvent A:Solvent B ratio, the gradient time, the final Solvent A:Solvent B ratio, and the hold time at the final Solvent A:Solvent B concentration.

HPLC Condition A: Column: Zorbax Eclipse Plus C18, 21.2×100 mm, 5 μm particles; Solvent A=0.1% Formic Acid in 100% Water. Solvent B=Acetonitrile. Flow Rate=40 mL/min. Wavelength=215 and 254 nm. ESI+Range: 150 to 1500 Dalton.

HPLC Condition B: Column: Sunfire prep C18 OBD, 30×100 mm, 5 μm particles; Solvent A:water:MeCN 95:5 w/0.1% TFA, Solvent B: MeCN:water 95:5 w/0.1% TFA. Flow Rate=42 mL/min. Wavelength=220 and 254 nm.

HPLC Condition C: Column: Waters Xterra C18, 19×100 mm, 10 μm particles; Solvent A=0.1% $NH_{40}H$ in 100% Water. Solvent B=Acetonitrile. Flow Rate=40 mL/min. Wavelength=215 and 254 nm. ESI+Range: 150 to 1500 Dalton.

General LMCS Analysis Methods:

LCMS Method A:

Column: Acquity CSH C18, 2.1×30 mm, 1.7 μm particles; Solvent A=0.1% Formic acid in 100% Water. Solvent B=0.1% Formic Acid in 100% Acetonitrile. Flow Rate=0.8 mL/min. Start % B=5. Final % B=95. Gradient Time=1.7 min, then a 0.2 min hold at 95% B. Wavelength=215 and 254 nm. ESI+Range: 150 to 1500 Dalton. System: Agilent 1290 Infinity II LCMS Method B:

Column: Acquity BEH C18, 2.1×30 mm, 1.7 μm particles; Solvent A=0.1% Formic acid in 100% Water. Solvent B=0.1% Formic Acid in 100% Acetonitrile. Flow Rate=0.8 mL/min. Start % B=5. Final % B=95. Gradient Time=1.7 min, then a 0.2 min hold at 95% B. Wavelength=215 and 254 nm.

LCMS Method C:

Column: Zorbax Eclipse Plus C18, 2.1×50 mm, 1.7 μm particles; Solvent A=0.1% Formic acid in 100% Water. Solvent B=0.1% Formic Acid in 100% Acetonitrile. Flow Rate=1 mL/min. Start % B=5. Final % B=95. Gradient Time=2.1 min, then a 0.3 min hold at 95% B. Wavelength=215 and 254 nm. ESI+Range: 150 to 1500 Dalton.

Preparation of Example 1: N-((S)-1-((3P)-3-(4-chloro-1-methyl-3-(methylsulfonamido)-1H-indazol-7-yl)-7-(cyclopent-3-en-1-yloxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

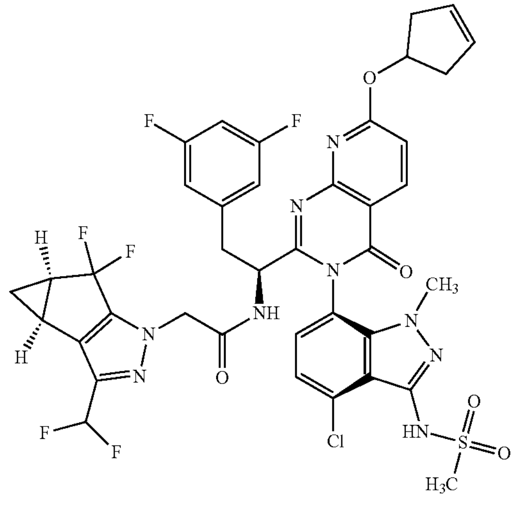

The title compound was prepared according to General Procedure A using cyclopent-3-en-1-ol as the coupling partner. The experiment afforded the title compound, N-((S)-1-((3P)-3-(4-chloro-1-methyl-3-(methylsulfonamido)-1H-indazol-7-yl)-7-(cyclopent-3-en-1-yloxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS A: retention time=1.49 min.; observed ion=888.1 (M+H). 1H NMR (500 MHz, METHANOL-d4) δ ppm 8.43-8.52 (m, 1H) 7.27-7.34 (m, 1H) 7.17-7.25 (m, 1H) 6.97-7.04 (m, 1H) 6.54-6.84 (m, 4H) 5.89-5.96 (m, 1H) 5.80-5.87 (m, 2H) 4.88-4.89 (m, 1H) 4.50-4.65 (m, 2H) 3.59-3.64 (m, 3H) 3.43-3.51 (m, 1H) 3.23-3.26 (m, 3H) 3.09-3.17 (m, 1H) 2.93-3.02 (m, 2H) 2.57-2.66 (m, 2H) 2.40-2.48 (m, 2H) 1.34-1.40 (m, 1H) 0.98-1.04 (m, 1H)

Preparation of Example 2: N-((S)-1-((3P,3P)-3-(4-chloro-1-methyl-3-(methylsulfonamido)-1H-indazol-7-yl)-4-oxo-7-(pyridin-4-ylmethoxy)-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

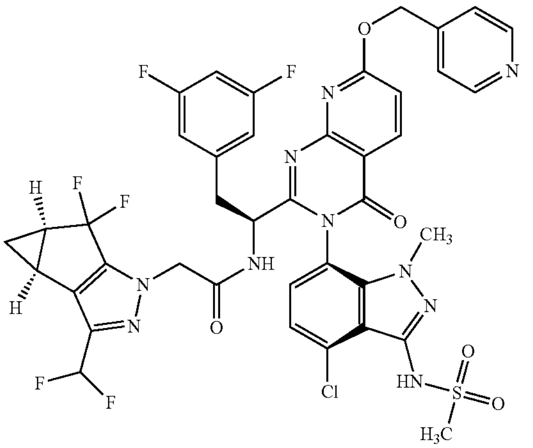

The title compound was prepared according to General Procedure A using pyridin-4-ylmethanol as the coupling partner. The experiment afforded the title compound, N-((S)-1-((3P,3P)-3-(4-chloro-1-methyl-3-(methylsulfonamido)-1H-indazol-7-yl)-4-oxo-7-(pyridin-4-ylmethoxy)-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS A: retention time=1.1 min.; observed ion=913.3 (M+H). 1H NMR (500 MHz, METHANOL-d4) δ ppm 8.51-8.65 (m, 3H) 7.53-7.62 (m, 2H) 7.18-7.33 (m, 3H) 6.54-6.86 (m, 4H) 5.70-5.82 (m, 2H) 4.84-4.87 (m, 1H) 4.45-4.61 (m, 2H) 3.60-3.64 (m, 3H) 3.44-3.48 (m, 1H) 3.23-3.27 (m, 3H) 3.07-3.14 (m, 1H) 2.40-2.47 (m, 2H) 1.34-1.40 (m, 1H) 0.97-1.03 (m, 1H)

Preparation of Example 3: N-((S)-1-((3P)-3-(4-chloro-1-methyl-3-(methylsulfonamido)-1H-indazol-7-yl)-7-((1-(2,2-difluoroethyl)-1H-pyrazol-3-yl)methoxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

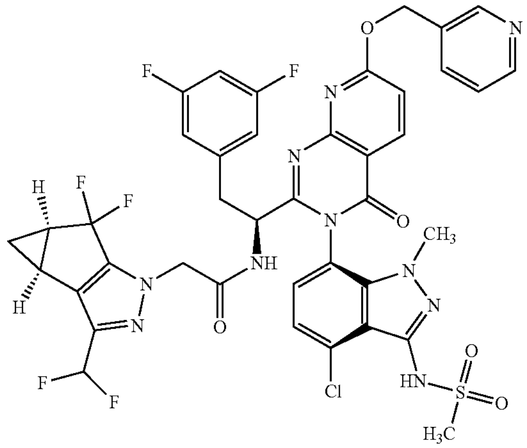

The title compound was prepared according to General Procedure A using pyridin-3-ylmethanol as the coupling partner. The experiment afforded the title compound, N-((S)-1-((3P)-3-(4-chloro-1-methyl-3-(methylsulfonamido)-1H-indazol-7-yl)-7-((1-(2,2-difluoroethyl)-1H-pyrazol-3-yl)methoxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS A: retention time=1.18 min.; observed ion=913.3 (M+H).

Preparation of Example 4: N-((S)-1-((3P)-3-(4-chloro-1-methyl-3-(methylsulfonamido)-1H-indazol-7-yl)-4-oxo-7-(4,4,4-trifluoro-3,3-dimethylbutoxy)-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

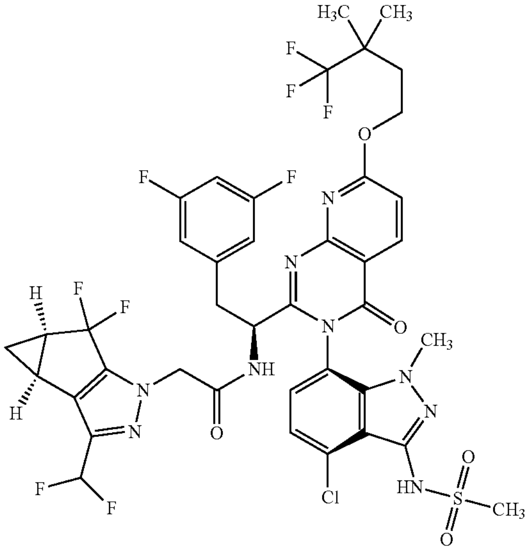

The title compound was prepared according to General Procedure B using 4,4,4-trifluoro-3,3-dimethylbutan-1-ol as the coupling partner. The experiment afforded the title compound, N-((S)-1-((3P)-3-(4-chloro-1-methyl-3-(methylsulfonamido)-1H-indazol-7-yl)-4-oxo-7-(4,4,4-trifluoro-3,3-dimethylbutoxy)-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS B: retention time=1.55 min.; observed ion=960.4 (M+H). 1H NMR (500 MHz, METHANOL-d4) δ ppm 8.46-8.52 (m, 1H) 7.26-7.34 (m, 1H) 7.17-7.25 (m, 1H) 7.04-7.09 (m, 1H) 6.55-6.85 (m, 4H) 4.84-4.86 (m, 1H) 4.68-4.76 (m, 2H) 4.51-4.64 (m, 2H) 3.58-3.63 (m, 3H) 3.45-3.50 (m, 1H) 3.21-3.26 (m, 3H) 3.08-3.17 (m, 1H) 2.39-2.50 (m, 2H) 2.11-2.19 (m, 2H) 1.35-1.43 (m, 1H) 1.30-1.32 (m, 6H) 0.99-1.04 (m, 1H)

Preparation of Example 5: N-((S)-1-((3P)-3-(4-chloro-1-methyl-3-(methylsulfonamido)-1H-indazol-7-yl)-7-(3-methyl-3-phenylbutoxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

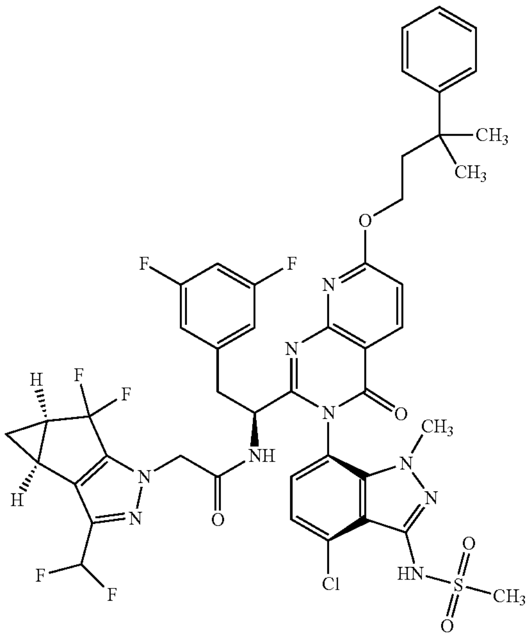

The title compound was prepared according to General Procedure B using 3-methyl-3-phenylbutan-1-ol as the coupling partner. The experiment afforded the title compound, N-((S)-1-((3P)-3-(4-chloro-1-methyl-3-(methylsulfonamido)-1H-indazol-7-yl)-7-(3-methyl-3-phenylbutoxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS B: retention time=1.66 min.; observed ion=968.2 (M+H). 1H NMR (500 MHz, METHANOL-d4) δ ppm 8.39-8.44 (m, 1H) 7.45-7.51 (m, 2H) 7.32-7.39 (m, 2H) 7.26-7.30 (m, 1H) 7.14-7.23 (m, 2H) 6.88-6.93 (m, 1H) 6.53-6.82 (m, 4H) 4.80-4.84 (m, 1H) 4.51-4.63 (m, 2H) 4.33-4.39 (m, 2H) 3.56-3.61 (m, 3H) 3.41-3.46 (m, 1H) 3.21-3.23 (m, 3H) 3.04-3.14 (m, 1H) 2.38-2.47 (m, 2H) 2.28-2.35 (m, 2H) 1.46-1.51 (m, 6H) 1.36-1.40 (m, 1H) 0.98-1.04 (m, 1H)

Preparation of Example 6: N-((S)-1-((3P,3P)-3-(4-chloro-1-methyl-3-(methylsulfonamido)-1H-indazol-7-yl)-7-((4,6-dimethylpyrimidin-2-yl)methoxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

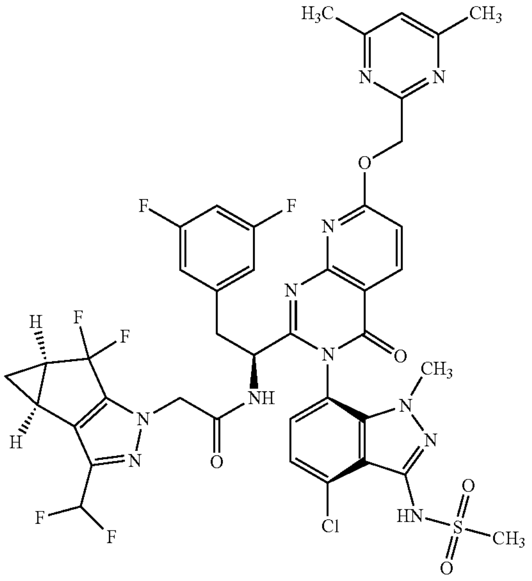

The title compound was prepared according to General Procedure B using (4,6-dimethylpyrimidin-2-yl)methanol as the coupling partner. The experiment afforded the title compound, N-((S)-1-((3P,3P)-3-(4-chloro-1-methyl-3-(methylsulfonamido)-1H-indazol-7-yl)-7-((4,6-dimethylpyrimidin-2-yl)methoxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS B: retention time=1.32 min.; observed ion=942.2 (M+H). 1H NMR (500 MHz, METHANOL-d4) δ ppm 8.50-8.59 (m, 1H) 7.29-7.33 (m, 1H) 7.19-7.26 (m, 2H) 6.51-6.82 (m, 4H) 5.69-5.77 (m, 2H) 4.82-4.86 (m, 2H) 4.49-4.61 (m, 2H) 3.57-3.64 (m, 3H) 3.39-3.46 (m, 1H) 3.21-3.25 (m, 3H) 3.02-3.13 (m, 1H) 2.33-2.54 (m, 8H) 1.34-1.41 (m, 1H) 0.97-1.04 (m, 1H)

Preparation of Example 7: N-((S)-1-((3P,3P)-3-(4-chloro-1-methyl-3-(methylsulfonamido)-1H-indazol-7-yl)-7-((4-methylpyrimidin-2-yl)methoxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

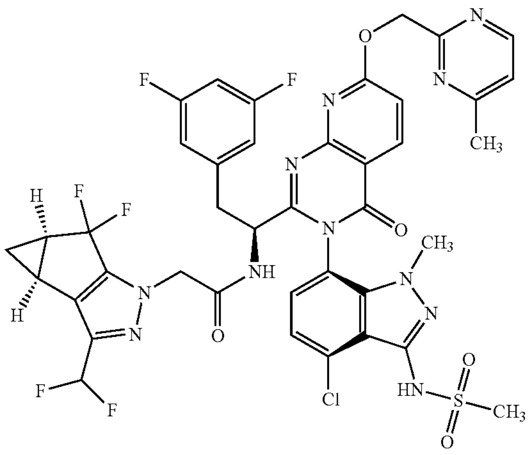

The title compound was prepared according to General Procedure B using (4-methylpyrimidin-2-yl)methanol as the coupling partner. The experiment afforded the title compound, N-((S)-1-((3P,3P)-3-(4-chloro-1-methyl-3-(methylsulfonamido)-1H-indazol-7-yl)-7-((4-methylpyrimidin-2-yl)methoxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS B: retention time=1.26 min.; observed ion=928.3 (M+H). 1H NMR (500 MHz, METHANOL-d4) δ ppm 8.48-8.71 (m, 2H) 7.05-7.38 (m, 4H) 6.47-6.85 (m, 4H) 5.71-5.84 (m, 2H) 4.79-4.81 (m, 1H) 4.57-4.63 (m, 3H) 4.50-4.56 (m, 2H) 3.38-3.46 (m, 1H) 3.21-3.25 (m, 3H) 3.02-3.11 (m, 1H) 2.55-2.60 (m, 3H) 2.39-2.47 (m, 2H) 1.33-1.41 (m, 1H) 0.97-1.03 (m, 1H)

Preparation of Example 8: N-((S)-1-((3P,3P)-3-(4-chloro-1-methyl-3-(methylsulfonamido)-1H-indazol-7-yl)-7-((5-methylpyrimidin-2-yl)methoxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

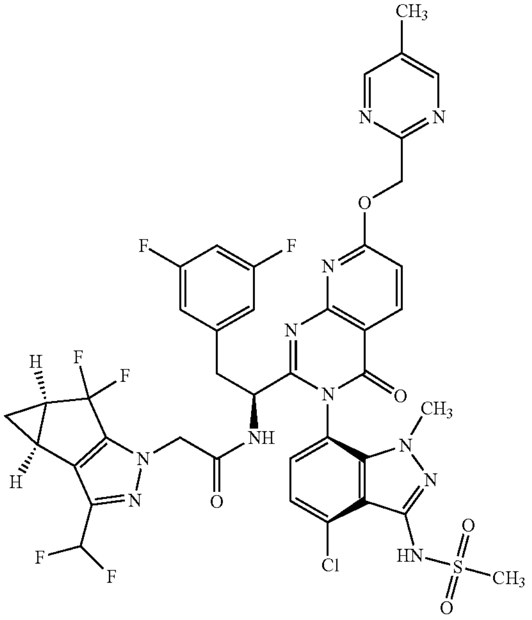

The title compound was prepared according to General Procedure B using (5-methylpyrimidin-2-yl)methanol as the coupling partner. The experiment afforded the title compound, N-((S)-1-((3P,3P)-3-(4-chloro-1-methyl-3-(methylsulfonamido)-1H-indazol-7-yl)-7-((5-methylpyrimidin-2-yl)methoxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS B: retention time=1.31 min.; observed ion=928.2 (M+H). 1H NMR (500 MHz, METHANOL-d4) δ ppm 8.63-8.72 (m, 2H) 8.53-8.57 (m, 1H) 7.13-7.31 (m, 3H) 6.56-6.81 (m, 4H) 5.74-5.85 (m, 2H) 4.82-4.86 (m, 1H) 4.48-4.62 (m, 2H) 3.54-3.61 (m, 3H) 3.39-3.44 (m, 1H) 3.21-3.23 (m, 3H) 3.02-3.09 (m, 1H) 2.40-2.47 (m, 2H) 2.37-2.39 (m, 3H) 1.34-1.40 (m, 1H) 0.98-1.03 (m, 1H)

Preparation of Example 9: N-((S)-1-((3P)-3-(4-chloro-1-methyl-3-(methylsulfonamido)-1H-indazol-7-yl)-7-(2-(methyl(2,2,2-trifluoroethyl)amino)ethoxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

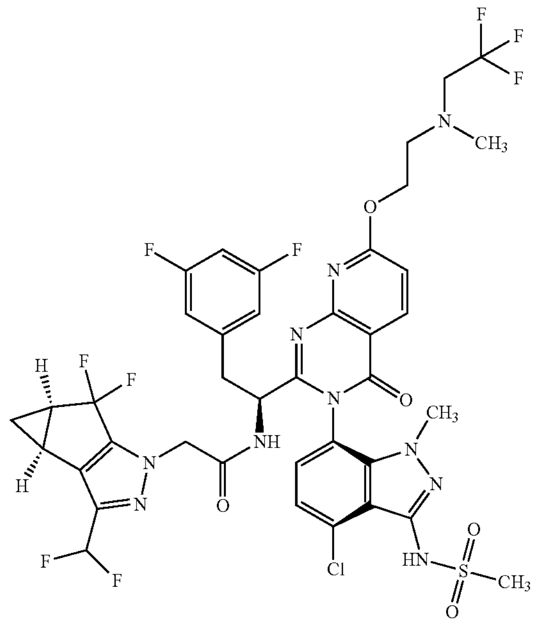

The title compound was prepared according to General Procedure A using 2-(methyl(2,2,2-trifluoroethyl)amino)ethanol as the coupling partner. The experiment afforded the title compound, N-((S)-1-((3P)-3-(4-chloro-1-methyl-3-(methylsulfonamido)-1H-indazol-7-yl)-7-(2-(methyl(2,2,2-trifluoroethyl)amino)ethoxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS A: retention time=1.46 min.; observed ion=961.2 (M+H). 1H NMR (500 MHz, METHANOL-d4) δ ppm 8.75-8.81 (m, 1H) 8.51-8.60 (m, 2H) 8.03-8.11 (m, 1H) 7.49-7.57 (m, 1H) 7.12-7.34 (m, 3H) 6.56-6.84 (m, 4H) 5.69-5.77 (m, 2H) 4.50-4.62 (m, 2H) 3.60-3.63 (m, 3H) 3.47-3.51 (m, 1H) 3.23-3.25 (m, 3H) 3.10-3.16 (m, 1H) 2.40-2.48 (m, 2H) 1.34-1.40 (m, 1H) 0.99-1.04 (m, 1H)

Preparation of Example 10: N-((S)-1-((3P)-3-(4-chloro-1-methyl-3-(methylsulfonamido)-1H-indazol-7-yl)-7-(2-(N-methylmethylsulfonamido)ethoxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

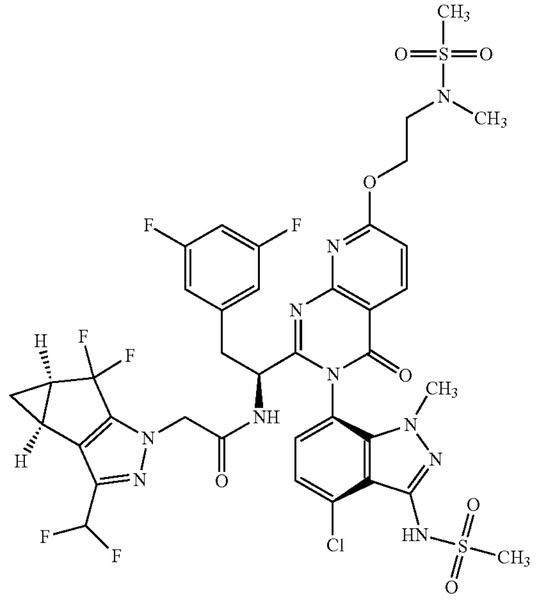

The title compound was prepared according to General Procedure B using N-(2-hydroxyethyl)-N-methylmethanesulfonamide as the coupling partner. The experiment afforded the title compound, N-((S)-1-((3P)-3-(4-chloro-1-methyl-3-(methylsulfonamido)-1H-indazol-7-yl)-7-(2-(N-methylmethylsulfonamido)ethoxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS B: retention time=1.29 min.; observed ion=957.2 (M+H). 1H NMR (500 MHz, METHANOL-d4) δ ppm 8.47-8.55 (m, 1H) 7.29-7.36 (m, 1H) 7.19-7.26 (m, 1H) 7.09-7.14 (m, 1H) 6.54-6.86 (m, 4H) 4.85-4.86 (m, 1H) 4.74-4.79 (m, 2H) 4.51-4.61 (m, 2H) 3.68-3.74 (m, 2H) 3.58-3.65 (m, 3H) 3.45-3.50 (m, 1H) 3.25-3.26 (m, 3H) 3.09-3.16 (m, 1H) 3.03-3.06 (m, 3H) 2.93-2.96 (m, 3H) 2.40-2.48 (m, 2H) 1.36-1.41 (m, 1H) 0.99-1.05 (m, 1H)

Preparation of Example 11: N-((S)-1-((3P)-3-(4-chloro-1-methyl-3-(methylsulfonamido)-1H-indazol-7-yl)-7-(3-(methyl(2,2,2-trifluoroethyl)amino)propoxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

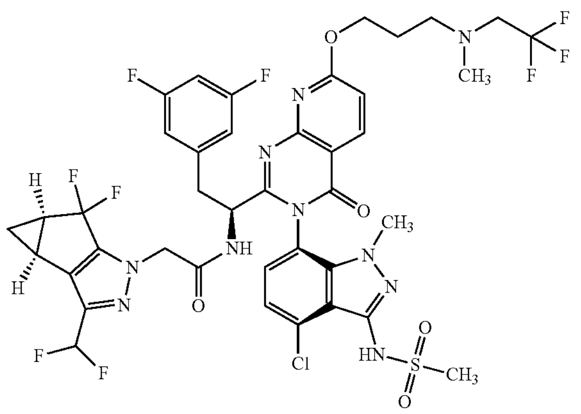

The title compound was prepared according to General Procedure A using 3-(methyl(2,2,2trifluoroethyl)amino)propan-1-ol as the coupling partner. The experiment afforded the title compound, N-((S)-1-((3P)-3-(4-chloro-1-methyl-3-(methylsulfonamido)-1H-indazol-7-yl)-7-(3-(methyl(2,2,2-trifluoroethyl)amino)propoxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS A: retention time=1.47 min.; observed ion=975.4 (M+H). 1H NMR (500 MHz, METHANOL-d4) δ ppm 8.43-8.53 (m, 1H) 7.02-7.35 (m, 3H) 6.52-6.84 (m, 4H) 4.84 (br d, J=8.64 Hz, 1H) 4.50-4.67 (m, 4H) 3.57-3.65 (m, 3H) 3.44-3.51 (m, 1H) 3.22-3.27 (m, 3H) 3.08-3.19 (m, 3H) 2.78-2.85 (m, 2H) 2.49-2.51 (m, 3H) 2.40-2.47 (m, 2H) 2.04-2.11 (m, 2H) 1.35-1.40 (m, 1H) 0.99-1.04 (m, 1H)

Preparation of Example 12: N-((S)-1-((3P,3P)-3-(4-chloro-1-methyl-3-(methylsulfonamido)-1H-indazol-7-yl)-7-(2-(1-methyl-1H-pyrazol-4-yl)ethoxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

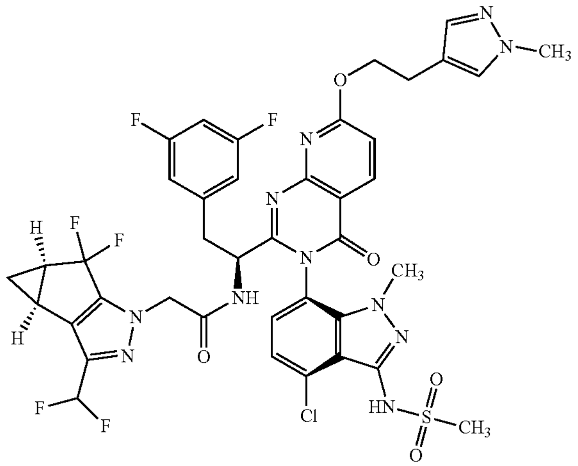

The title compound was prepared according to General Procedure A using 2-(1-methyl-1H-pyrazol-4-yl)ethan-1-ol as the coupling partner. The experiment afforded the title compound, N-((S)-1-((3P,3P)-3-(4-chloro-1-methyl-3-(methylsulfonamido)-1H-indazol-7-yl)-7-(2-(1-methyl-1H-pyrazol-4-yl)ethoxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS A: retention time=1.39 min.; observed ion=930.2 (M+H). 1H NMR (500 MHz, METHANOL-d4) δ ppm 8.46-8.53 (m, 1H) 7.54-7.61 (m, 1H) 7.43-7.48 (m, 1H) 7.27-7.34 (m, 1H) 7.19-7.26 (m, 1H) 7.04-7.12 (m, 1H) 6.55-6.83 (m, 4H) 4.83-4.86 (m, 1H) 4.49-4.75 (m, 4H) 3.86-3.91 (m, 3H) 3.59-3.64 (m, 3H) 3.43-3.50 (m, 1H) 3.22-3.27 (m, 3H) 3.05-3.19 (m, 3H) 2.38-2.46 (m, 2H) 1.34-1.40 (m, 1H) 0.98-1.04 (m, 1H)

Preparation of Example 13: N-((S)-1-((3P)-3-(4-chloro-1-methyl-3-(methylsulfonamido)-1H-indazol-7-yl)-7-((1-methyl-5-(trifluoromethyl)-1H-pyrazol-3-yl)methoxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

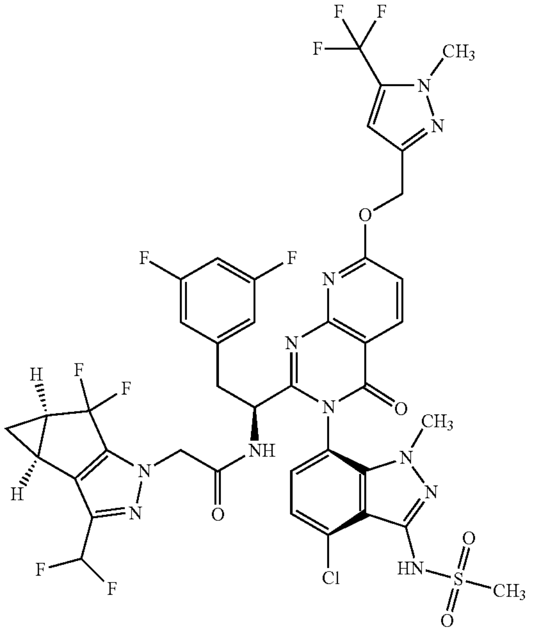

The title compound was prepared according to General Procedure A using (1-methyl-5-(trifluoromethyl)-1H-pyrazol-3-yl)methanol as the coupling partner. The experiment afforded the title compound, N-((S)-1-((3P)-3-(4-chloro-1-methyl-3-(methylsulfonamido)-1H-indazol-7-yl)-7-((1-methyl-5-(trifluoromethyl)-1H-pyrazol-3-yl)methoxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS A: retention time=1.41 min.; observed ion=984.2 (M+H). 1H NMR (500 MHz, METHANOL-d4) δ ppm 8.45-8.61 (m, 1H) 6.52-7.39 (m, 8H) 5.54-5.67 (m, 2H) 4.48-4.62 (m, 2H) 3.98-4.08 (m, 3H) 3.59-3.65 (m, 3H) 3.45-3.51 (m, 1H) 3.23-3.26 (m, 3H) 3.09-3.17 (m, 1H) 2.39-2.47 (m, 2H) 1.34-1.40 (m, 1H) 0.99-1.04 (m, 1H)

Preparation of Example 14: N-((R)-1-((3P,3P)-3-(4-chloro-1-methyl-3-(methylsulfonamido)-1H-indazol-7-yl)-7-(2-(1-methyl-1H-pyrazol-5-yl)ethoxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

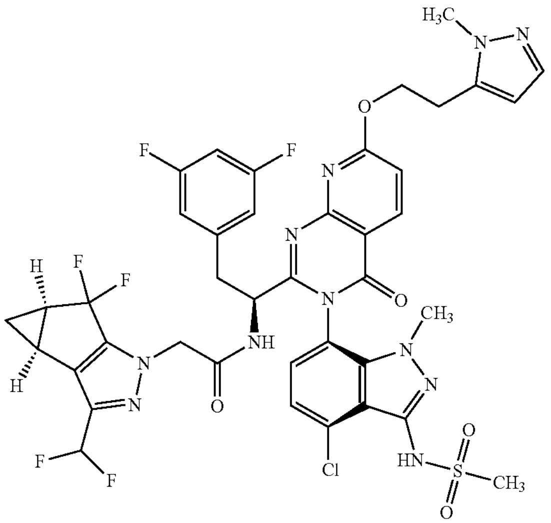

The title compound was prepared according to General Procedure B using 2-(1-methyl-1H-pyrazol-5-yl)ethan-1-ol as the coupling partner. The experiment afforded the title compound, N-((R)-1-((3P,3P)-3-(4-chloro-1-methyl-3-(methylsulfonamido)-1H-indazol-7-yl)-7-(2-(1-methyl-1H-pyrazol-5-yl)ethoxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS C: retention time=1.59 min.; observed ion=930.4 (M+H). 1H NMR (500 MHz, METHANOL-d4) δ ppm 8.47-8.53 (m, 1H) 7.38-7.42 (m, 1H) 7.28-7.33 (m, 1H) 7.18-7.23 (m, 1H) 7.04-7.10 (m, 1H) 6.55-6.84 (m, 4H) 6.23-6.26 (m, 1H) 4.82-4.87 (m, 3H) 4.50-4.63 (m, 2H) 3.93-3.97 (m, 3H) 3.60-3.64 (m, 3H) 3.44-3.51 (m, 1H) 3.23-3.26 (m, 3H) 3.09-3.17 (m, 1H) 2.38-2.48 (m, 2H) 1.33-1.40 (m, 1H) 1.24-1.32 (m, 2H) 0.98-1.03 (m, 1H)

Preparation of Example 15: N-((S)-1-((3P)-3-(4-chloro-1-methyl-3-(methylsulfonamido)-1H-indazol-7-yl)-7-(3-methoxy-3-methylbutoxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl) acetamide

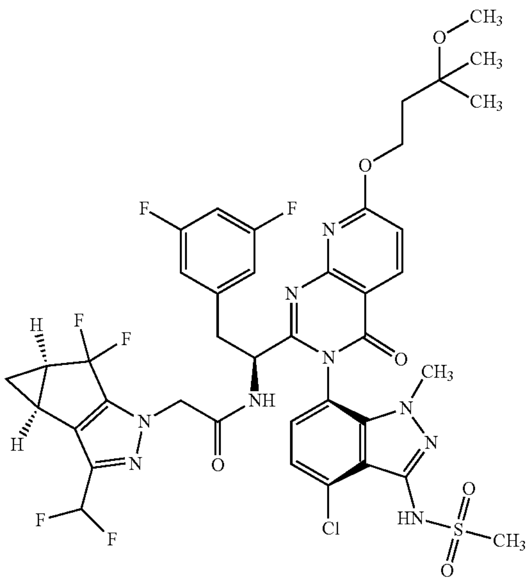

The title compound was prepared according to General Procedure A using 3-methoxy-3-methylbutan-1-ol as the coupling partner. The experiment afforded the title compound, N-((S)-1-((3P)-3-(4-chloro-1-methyl-3-(methylsulfonamido)-1H-indazol-7-yl)-7-(3-methoxy-3-methylbutoxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS B: retention time=1.5 min.; observed ion=922.2 (M+H). 1H NMR (500 MHz, METHANOL-d4) δ ppm 8.42-8.49 (m, 1H) 7.26-7.31 (m, 1H) 7.15-7.21 (m, 1H) 6.99-7.06 (m, 1H) 6.54-6.81 (m, 4H) 4.49-4.68 (m, 4H) 3.55-3.63 (m, 3H) 3.41-3.47 (m, 1H) 3.27-3.28 (m, 3H) 3.26-3.27 (m, 2H) 3.22-3.23 (m, 3H) 3.07-3.13 (m, 1H) 2.38-2.45 (m, 2H) 2.08-2.13 (m, 2H) 1.32-1.38 (m, 1H) 1.28-1.31 (m, 6H) 0.97-1.02 (m, 1H)

Preparation of Example 16: N-((S)-1-((3P,3P)-3-(4-chloro-1-methyl-3-(methylsulfonamido)-1H-indazol-7-yl)-7-(2-(1-methoxycyclobutyl)ethoxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl) acetamide

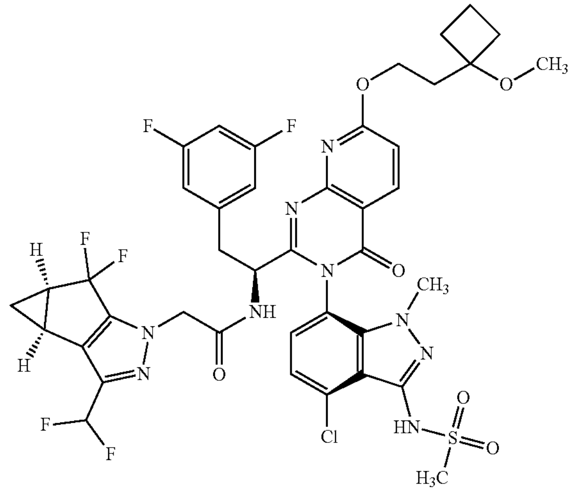

The title compound was prepared according to General Procedure A using 2-(1-methoxycyclobutyl)ethan-1-ol as the coupling partner. The experiment afforded the title compound, N-((S)-1-((3P,3P)-3-(4-chloro-1-methyl-3-(methylsulfonamido)-1H-indazol-7-yl)-7-(2-(1-methoxycyclobutyl)ethoxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS A: retention time=1.52 min.; observed ion=934.2 (M+H). 1H NMR (500 MHz, METHANOL-d4) δ ppm 8.42-8.52 (m, 1H) 7.28-7.33 (m, 1H) 7.17-7.23 (m, 1H) 7.02-7.08 (m, 1H) 6.55-6.83 (m, 4H) 4.85 (s, 1H) 4.52-4.70 (m, 4H) 3.60-3.64 (m, 3H) 3.44-3.50 (m, 1H) 3.27-3.28 (m, 3H) 3.23-3.25 (m, 3H) 3.09-3.15 (m, 1H) 2.40-2.47 (m, 2H) 2.29-2.35 (m, 2H) 2.19-2.27 (m, 2H) 2.03-2.13 (m, 2H) 1.68-1.88 (m, 2H) 1.33-1.41 (m, 1H) 0.98-1.04 (m, 1H)

Preparation of Example 17: N-((S)-1-((3P)-3-(4-chloro-1-methyl-3-(methylsulfonamido)-1H-indazol-7-yl)-7-((5-methoxypentyl)oxy)-4-oxo-3,4-dihydro-pyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

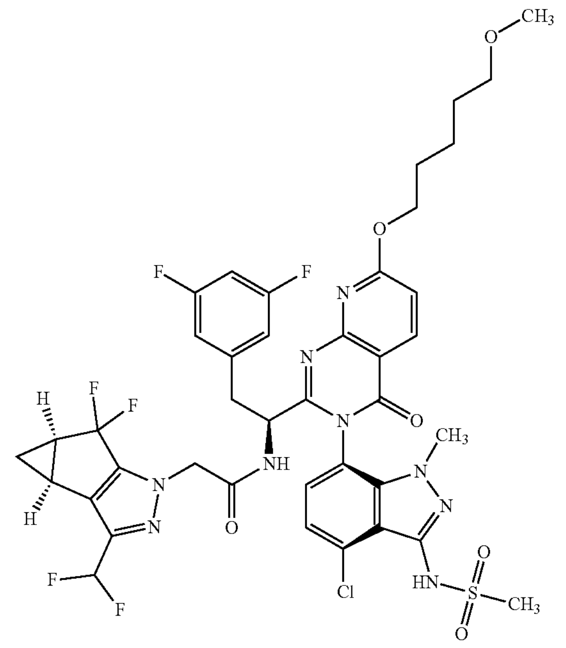

The title compound was prepared according to General Procedure A using 5-methoxypentan-1-ol as the coupling partner. The experiment afforded the title compound, N-((S)-1-((3P)-3-(4-chloro-1-methyl-3-(methylsulfonamido)-1H-indazol-7-yl)-7-((5-methoxypentyl)oxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS A: retention time=1.47 min.; observed ion=922.4 (M+H). 1H NMR (500 MHz, METHANOL-d4) δ ppm 8.44-8.53 (m, 1H) 7.30-7.35 (m, 1H) 7.18-7.25 (m, 1H) 7.02-7.09 (m, 1H) 6.56-6.83 (m, 4H) 4.83-4.85 (m, 1H) 4.52-4.65 (m, 4H) 3.61-3.63 (m, 3H) 3.45-3.50 (m, 3H) 3.36-3.37 (m, 3H) 3.24-3.26 (m, 3H) 3.10-3.16 (m, 1H) 2.40-2.47 (m, 2H) 1.90-1.97 (m, 2H) 1.67-1.74 (m, 2H) 1.58-1.64 (m, 2H) 1.34-1.40 (m, 1H) 0.99-1.04 (m, 1H)

Preparation of Example 18: N-(1-((3P,3P)-3-(4-chloro-1-methyl-3-(methylsulfonamido)-1H-indazol-7-yl)-4-oxo-7-(2,2,3,3,3-pentafluoropropoxy)-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

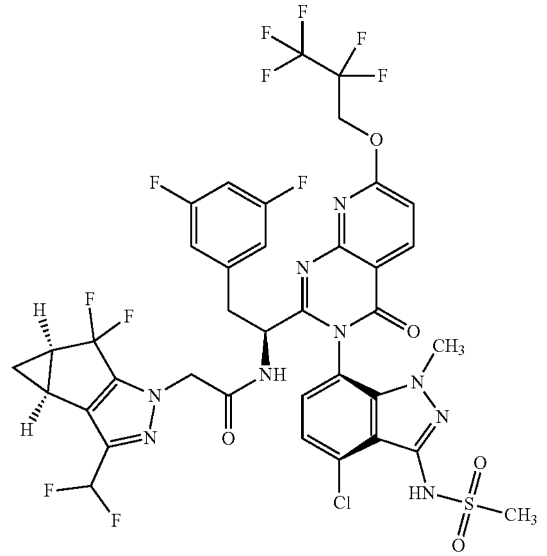

To a stirred solution of (S)-N-((6P)-7-((3P)-2-(1-amino-2-(3,5-difluorophenyl)ethyl)-4-oxo-7-(2,2,3,3,3-pentafluoropropoxy)pyrido[2,3-d]pyrimidin-3(4H)-yl)-4-chloro-1-methyl-1H-indazol-3-yl)-N-(methylsulfonyl)acetamide (0.05 g, 0.067 mmol) in Tetrahydrofuran (THF) (0.8 mL)/N,N-Dimethylformamide (DMF) (0.2 mL) were added 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (0.018 g, 0.067 mmol), 2-(3H-[1,2,3]triazolo[4,5-b]pyridin-3-yl)-1,1,3,3-tetramethylisouronium hexafluorophosphate(V) (0.030 g, 0.080 mmol) and DIPEA (0.017 mL, 0.100 mmol). The reaction mixture was stirred at rt for 3 h. The mixture was concentrated under reduced pressure and the residue was dissolved in DMF (2 mL); filtered; and the filtrate was subjected to HPLC purification to afford the title compound, N-(1-((3P,3P)-3-(4-chloro-1-methyl-3-(methylsulfonamido)-1H-indazol-7-yl)-4-oxo-7-(2,2,3,3,3-pentafluoropropoxy)-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS A: retention time=1.54 min.; observed ion=954.4 (M+H). 1H NMR (500 MHz, METHANOL-d4) δ ppm 8.58 (d, J=8.64 Hz, 1H) 7.29-7.31 (m, 1H) 7.23 (d, J=7.75 Hz, 1H) 7.18 (d, J=8.64 Hz, 1H) 6.52-6.84 (m, 4H) 5.24 (t, J=13.56 Hz, 2H) 4.54 (d, J=8.64 Hz, 2H) 3.60 (s, 3H) 3.45 (dd, J=14.31, 4.77 Hz, 1H) 3.23 (s, 3H) 3.11 (dd, J=14.16, 9.69 Hz, 1H) 2.38-2.44 (m, 2H) 1.32-1.38 (m, 1H) 0.96-1.01 (m, 1H)

Preparation of Example 19: N-((S)-1-((3P)-3-(4-chloro-1-methyl-3-(methylsulfonamido)-1H-indazol-7-yl)-4-oxo-7-(3,3,4,4,4-pentafluorobutoxy)-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl) acetamide

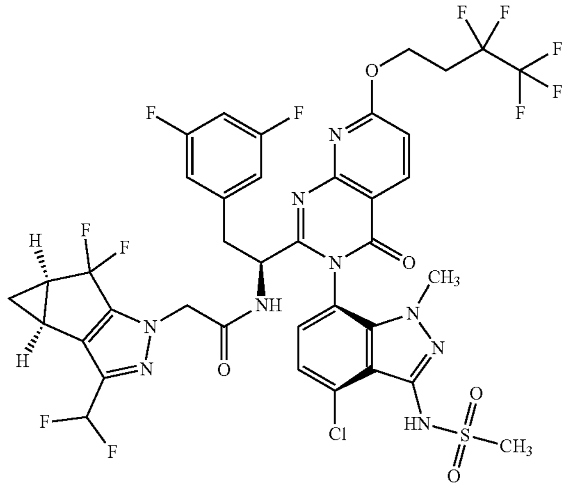

The title compound was prepared according to General Procedure A using 3,3,4,4,4-pentafluorobutan-1-ol as the coupling partner. The experiment afforded the title compound, N-((S)-1-((3P)-3-(4-chloro-1-methyl-3-(methylsulfonamido)-1H-indazol-7-yl)-4-oxo-7-(3,3,4,4,4-pentafluorobutoxy)-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS A: retention time=1.52 min.; observed ion=968.4 (M+H). 1H NMR (500 MHz, METHANOL-d4) δ ppm 8.47-8.58 (m, 1H) 7.16-7.32 (m, 2H) 7.07 (d, J=8.64 Hz, 1H) 6.52-6.83 (m, 4H) 4.82-4.85 (m, 3H) 4.51-4.64 (m, 2H) 3.55-3.63 (m, 3H) 3.41-3.49 (m, 1H) 3.21 (s, 3H) 3.11 (dd, J=14.16, 9.69 Hz, 1H) 2.72-2.92 (m, 2H) 2.35-2.46 (m, 2H) 1.31-1.40 (m, 1H) 0.93-1.02 (m, 1H)

Preparation of Example 20: N-((S)-1-((3P)-3-(4-chloro-1-methyl-3-(methylsulfonamido)-1H-indazol-7-yl)-4-oxo-7-(2-(2,2,3,3,3-pentafluoropropoxy) ethoxy)-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl) acetamide

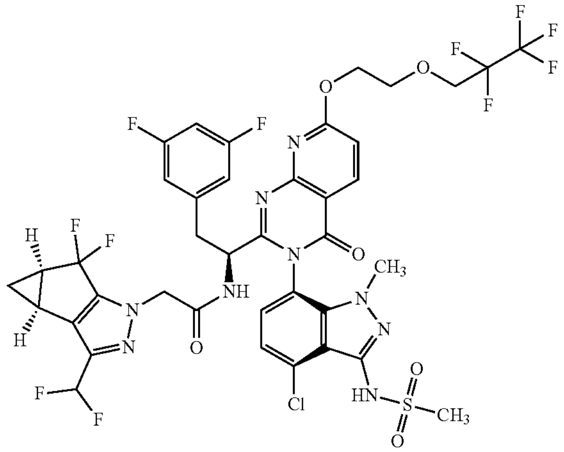

The title compound was prepared according to General Procedure A using 2-(2,2,3,3,3-pentafluoropropoxy)ethan-1-ol as the coupling partner. The experiment afforded the title compound, N-((S)-1-((3P)-3-(4-chloro-1-methyl-3-(methylsulfonamido)-1H-indazol-7-yl)-4-oxo-7-(2-(2,2,3,3,3-pentafluoropropoxy)ethoxy)-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS A: retention time=1.53 min.; observed ion=998.3 (M+H). 1H NMR (500 MHz, METHANOL-d4) δ ppm 8.42-8.54 (m, 1H) 7.25-7.31 (m, 1H) 7.18 (d, J=7.75 Hz, 1H) 7.08 (d, J=8.64 Hz, 1H) 6.51-6.86 (m, 4H) 4.70-4.74 (m, 2H) 4.50-4.59 (m, 2H) 4.12-4.21 (m, 2H) 4.05-4.10 (m, 2H) 3.59 (s, 3H) 3.42-3.47 (m, 1H) 3.21 (s, 3H) 3.10 (dd, J=14.01, 9.54 Hz, 1H) 2.37-2.46 (m, 2H) 1.32-1.38 (m, 1H) 1.19-1.28 (m, 2H) 0.96-1.02 (m, 1H)

Preparation of Example 21: N-((S)-1-((3P)-3-(4-chloro-1-methyl-3-(methylsulfonamido)-1H-indazol-7-yl)-4-oxo-7-((1-(trifluoromethyl)cyclopropyl)methoxy)-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

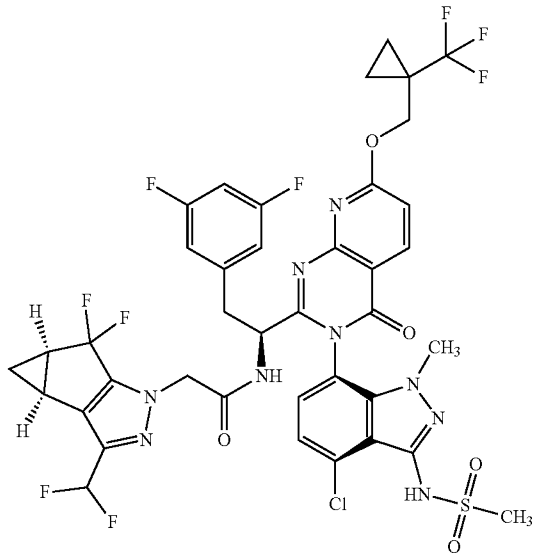

The title compound was prepared according to General Procedure B using (1-(trifluoromethyl)cyclopropyl)methanol as the coupling partner. The experiment afforded the title compound, N-((S)-1-((3P)-3-(4-chloro-1-methyl-3-(methylsulfonamido)-1H-indazol-7-yl)-4-oxo-7-((1-(trifluoromethyl)cyclopropyl)methoxy)-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS B: retention time=1.56 min.; observed ion=944.2 (M+H). 1H NMR (500 MHz, METHANOL-d4) δ ppm 8.30-8.52 (m, 1H) 6.93-7.25 (m, 3H) 6.37-6.74 (m, 4H) 4.71-4.75 (m, 1H) 4.60-4.66 (m, 2H) 4.38-4.49 (m, 2H) 3.45-3.53 (m, 3H) 3.32-3.38 (m, 1H) 3.10-3.15 (m, 3H) 2.97-3.04 (m, 1H) 2.27-2.37 (m, 2H) 1.22-1.28 (m, 1H) 1.08-1.12 (m, 2H) 0.98-1.03 (m, 2H) 0.86-0.92 (m, 1H)

Preparation of Example 22: N-((S)-1-((3P)-3-(4-chloro-1-methyl-3-(methylsulfonamido)-1H-indazol-7-yl)-4-oxo-7-((6-(trifluoromethyl)pyridin-2-yl)methoxy)-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

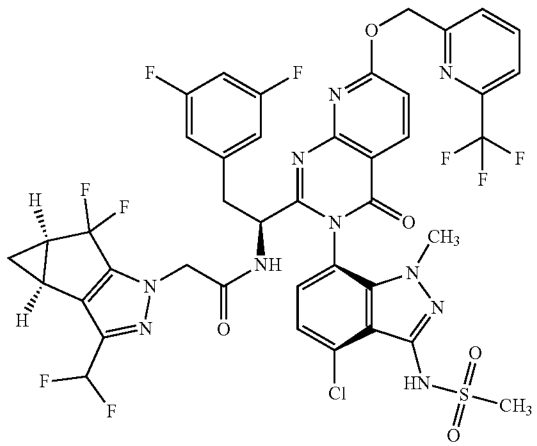

The title compound was prepared according to General Procedure A using (6-(trifluoromethyl)pyridin-2-yl)methanol as the coupling partner. The experiment afforded the title compound, N-((S)-1-((3P)-3-(4-chloro-1-methyl-3-(methylsulfonamido)-1H-indazol-7-yl)-4-oxo-7-((6-(trifluoromethyl)pyridin-2-yl)methoxy)-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS A: retention time=1.49 min.; observed ion=981.2 (M+H). 1H NMR (500 MHz, METHANOL-d4) δ ppm 8.53-8.61 (m, 1H) 8.06-8.16 (m, 1H) 7.75-7.89 (m, 2H) 7.16-7.35 (m, 3H) 6.53-6.85 (m, 4H) 5.74-5.86 (m, 2H) 4.83-4.85 (m, 1H) 4.48-4.63 (m, 2H) 3.58-3.64 (m, 3H) 3.41-3.50 (m, 1H) 3.22-3.27 (m, 3H) 3.03-3.14 (m, 1H) 2.36-2.47 (m, 2H) 1.33-1.40 (m, 1H) 0.95-1.04 (m, 1H)

Preparation of Example 23: N-((S)-1-((3P)-3-(4-chloro-1-methyl-3-(methylsulfonamido)-1H-indazol-7-yl)-4-oxo-7-((4-(trifluoromethyl)thiazol-2-yl)methoxy)-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

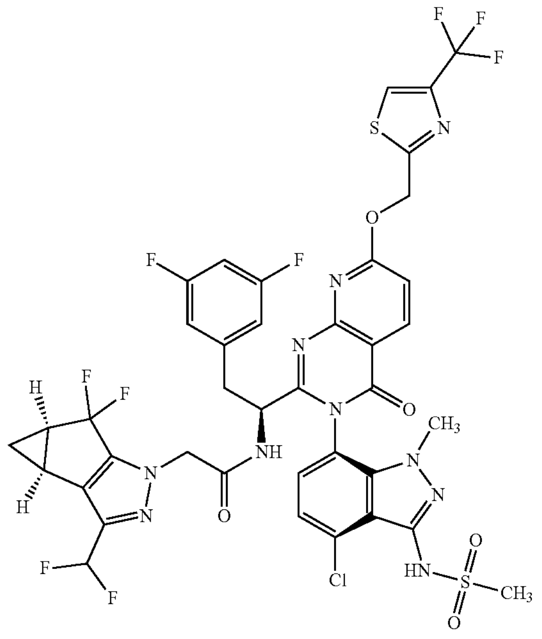

The title compound was prepared according to General Procedure A using (4-(trifluoromethyl)thiazol-2-yl)methanol as the coupling partner. The experiment afforded the title compound, N-((S)-1-((3P)-3-(4-chloro-1-methyl-3-(methylsulfonamido)-1H-indazol-7-yl)-4-oxo-7-((4-(trifluoromethyl)thiazol-2-yl)methoxy)-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS A: retention time=1.49 min.; observed ion=987.2 (M+H).

Preparation of Example 24: N-((S)-1-((3P)-3-(4-chloro-1-methyl-3-(methylsulfonamido)-1H-indazol-7-yl)-4-oxo-7-((1-(2,2,2-trifluoroethyl)-1H-pyrazol-3-yl)methoxy)-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

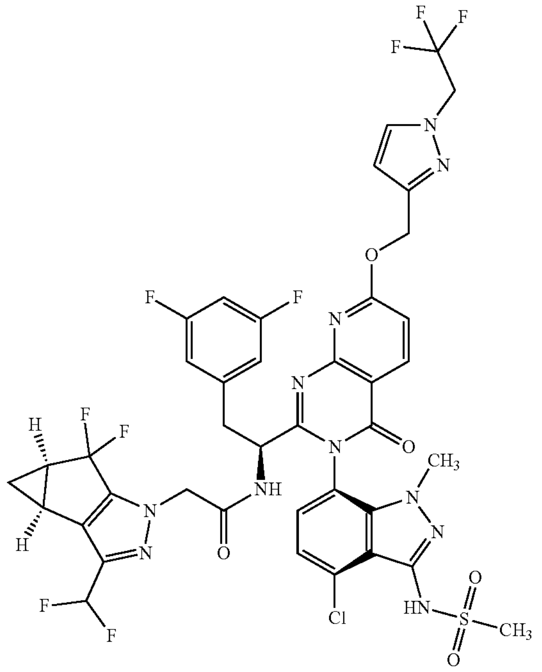

The title compound was prepared according to General Procedure A using (1-(2,2,2-trifluoroethyl)-1H-pyrazol-3-yl)methanol as the coupling partner. The experiment afforded the title compound, N-((S)-1-((3P)-3-(4-chloro-1-methyl-3-(methylsulfonamido)-1H-indazol-7-yl)-4-oxo-7-((1-(2,2,2-trifluoroethyl)-1H-pyrazol-3-yl)methoxy)-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS A: retention time=1.39 min.; observed ion=984.2 (M+H). 1H NMR (500 MHz, METHANOL-d4) δ ppm 8.46-8.52 (m, 1H) 7.80-7.84 (m, 1H) 7.28-7.35 (m, 1H) 7.18-7.24 (m, 1H) 7.03-7.09 (m, 1H) 6.54-6.87 (m, 5H) 5.52-5.62 (m, 2H) 4.93-5.01 (m, 2H) 4.52-4.62 (m, 2H) 3.61-3.67 (m, 3H) 3.47-3.52 (m, 1H) 3.25 (s, 3H) 3.12-3.18 (m, 1H) 2.41-2.50 (m, 2H) 1.35-1.41 (m, 1H) 0.99-1.05 (m, 1H)

Preparation of Example 25: N-((S)-1-((3P)-3-(4-chloro-1-methyl-3-(methylsulfonamido)-1H-indazol-7-yl)-4-oxo-7-(2-((2,2,2-trifluoroethyl)amino)ethoxy)-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

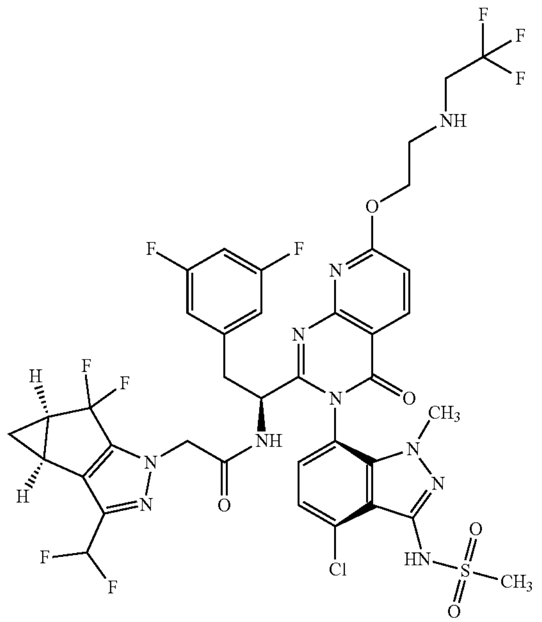

The title compound was prepared according to General Procedure A using 2-((2,2,2-trifluoroethyl)amino)ethan-1-ol as the coupling partner. The experiment afforded the title compound, N-((S)-1-((3P)-3-(4-chloro-1-methyl-3-(methylsulfonamido)-1H-indazol-7-yl)-4-oxo-7-(2-((2,2,2-trifluoroethyl)amino)ethoxy)-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS A: retention time=1.31 min.; observed ion=947.2 (M+H). 1H NMR (500 MHz, METHANOL-d4) δ ppm 8.09-8.17 (m, 1H) 7.29-7.37 (m, 2H) 6.55-6.87 (m, 6H) 4.44-4.79 (m, 5H) 3.64 (s, 3H) 3.44-3.48 (m, 1H) 3.36-3.38 (m, 2H) 3.25-3.26 (m, 4H) 3.13-3.18 (m, 3H) 2.43-2.48 (m, 2H) 1.36-1.41 (m, 1H) 0.97-1.02 (m, 1H)

Preparation of Example 26: N-((S)-1-((3P)-3-(4-chloro-1-methyl-3-(methylsulfonamido)-1H-indazol-7-yl)-4-oxo-7-(2-(2,2,2-trifluoroethoxy)ethoxy)-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

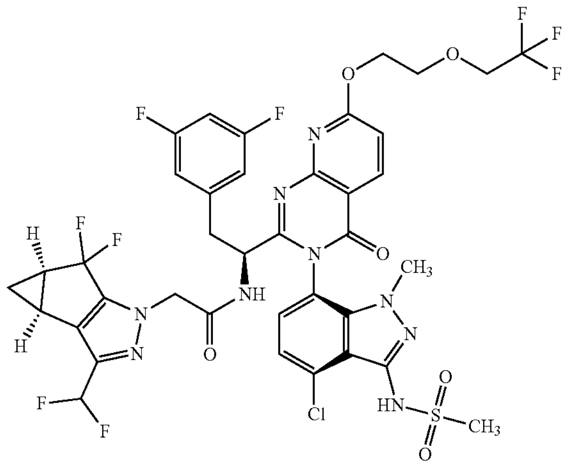

The title compound was prepared according to General Procedure A using 2-(2,2,2-trifluoroethoxy)ethan-1-ol as the coupling partner. The experiment afforded the title compound, N-((S)-1-((3P)-3-(4-chloro-1-methyl-3-(methylsulfonamido)-1H-indazol-7-yl)-4-oxo-7-(2-(2,2,2-trifluoroethoxy)ethoxy)-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS A: retention time=1.43 min.; observed ion=948.4 (M+H). 1H NMR (500 MHz, METHANOL-d4) δ ppm 8.44-8.52 (m, 1H) 7.27 (br d, J=8.05 Hz, 1H) 7.18 (d, J=7.75 Hz, 1H) 7.09 (d, J=8.64 Hz, 1H) 6.53-6.82 (m, 4H) 4.83 (t, J=4.77 Hz, 1H) 4.70-4.75 (m, 2H) 4.50-4.61 (m, 2H) 4.02-4.13 (m, 4H) 3.59 (s, 3H) 3.41-3.49 (m, 1H) 3.21 (s, 3H) 3.10 (dd, J=14.16, 9.69 Hz, 1H) 2.41 (ddd, J=11.55, 7.53, 4.17 Hz, 2H) 1.33-1.38 (m, 1H) 0.96-1.03 (m, 1H)

Preparation of Example 27: N-((S)-1-((3P,3P)-3-(4-chloro-1-methyl-3-(methylsulfonamido)-1H-indazol-7-yl)-4-oxo-7-(2,2,3,3-tetrafluoropropoxy)-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl) acetamide

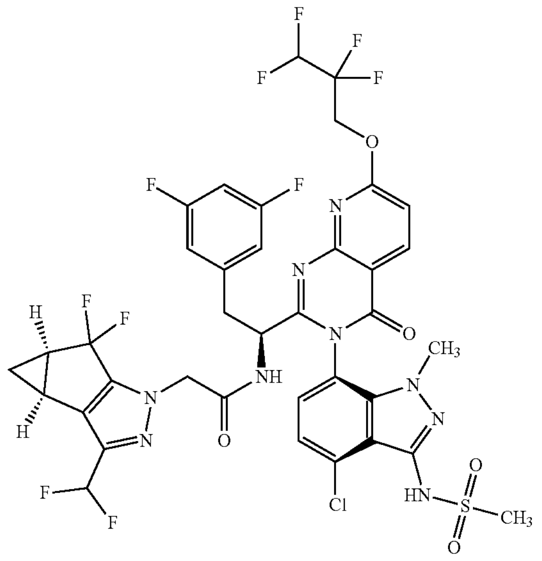

To a stirred solution of (S)-N-((6P)-7-((3P)-2-(1-amino-2-(3,5-difluorophenyl)ethyl)-4-oxo-7-(2,2,3,3-tetrafluoropropoxy)pyrido[2,3-d]pyrimidin-3(4H)-yl)-4-chloro-1-methyl-1H-indazol-3-yl)-N-(methylsulfonyl)acetamide (0.05 g, 0.068 mmol) in Tetrahydrofuran (THF) (1 mL) were added 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (0.018 g, 0.068 mmol), DIPEA (0.036 mL, 0.205 mmol) and 2,4,6-tripropyl-1,3,5,2,4,6-trioxatriphosphinane 2,4,6-trioxide (50% wt. in EtOAc, 0.081 mL, 0.137 mmol). The reaction mixture was stirred at rt for 3 h. To the mixture was added ammonia in methanol (2.0 M, 1 mL) and the mixture was stirred for 2 h. The mixture was concentrated under reduced pressure; the residue was dissolved in DMF, then filtered, and the filtrate was subjected to HPLC purification to afford the title compound, N-((S)-1-((3P,3P)-3-(4-chloro-1-methyl-3-(methylsulfonamido)-1H-indazol-7-yl)-4-oxo-7-(2,2,3,3-tetrafluoropropoxy)-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS A: retention time=1.45 min.; observed ion=936.4 (M+H). 1H NMR (500 MHz, METHANOL-d4) δ ppm 8.57 (d, J=8.64 Hz, 1H) 7.30 (d, J=7.75 Hz, 1H) 7.23 (d, J=7.75 Hz, 1H) 7.18 (d, J=8.64 Hz, 1H) 6.54-6.82 (m, 4H) 6.27-6.52 (m, 1H) 5.05 (t, J=13.11 Hz, 2H) 4.82-4.85 (m, 1H) 4.48-4.61 (m, 2H) 3.60 (s, 3H) 3.45 (dd, J=14.01, 4.77 Hz, 1H) 3.23 (s, 3H) 3.11 (dd, J=14.16, 9.69 Hz, 1H) 2.38-2.46 (m, 2H) 1.31-1.39 (m, 1H) 0.96-1.02 (m, 1H)

Preparation of Example 28: N-((S)-1-((3P)-3-(4-chloro-1-methyl-3-(methylsulfonamido)-1H-indazol-7-yl)-7-((1-(difluoromethyl)-1H-imidazol-2-yl)methoxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl) acetamide

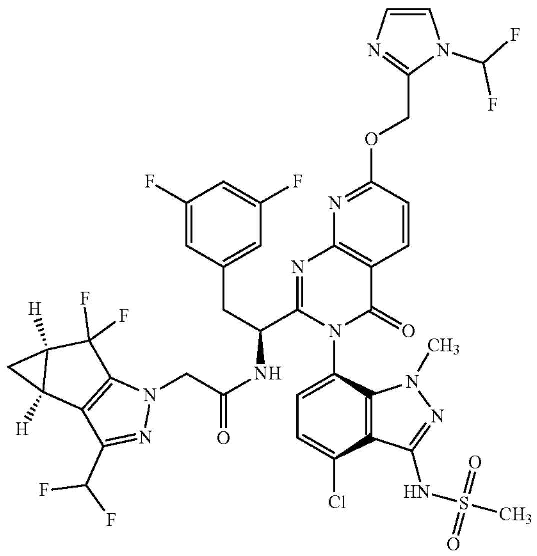

The title compound was prepared according to General Procedure A using (1-(difluoromethyl)-1H-imidazol-2-yl) methanol as the coupling partner. The experiment afforded the title compound, N-((S)-1-((3P)-3-(4-chloro-1-methyl-3-(methylsulfonamido)-1H-indazol-7-yl)-7-((1-(difluoromethyl)-1H-imidazol-2-yl)methoxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS A: retention time=1.31 min.; observed ion=952.2 (M+H). 1H NMR (500 MHz, METHANOL-d4) δ ppm 8.14-8.21 (m, 1H) 7.83-8.11 (m, 1H) 7.52 (d, J=1.49 Hz, 1H) 7.23-7.29 (m, 1H) 7.03-7.13 (m, 2H) 6.53-6.86 (m, 5H) 5.92-6.03 (m, 2H) 4.80-4.84 (m, 2H) 4.41-4.55 (m, 2H) 3.65-3.71 (m, 3H) 3.23-3.27 (m, 3H) 2.99-3.08 (m, 1H) 2.40-2.50 (m, 2H) 1.35-1.42 (m, 1H) 0.95-1.03 (m, 1H)

Preparation of Example 29: N-((S)-1-((3P)-3-(4-chloro-1-methyl-3-(methylsulfonamido)-1H-indazol-7-yl)-7-(2-(difluoromethoxy)ethoxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl) acetamide

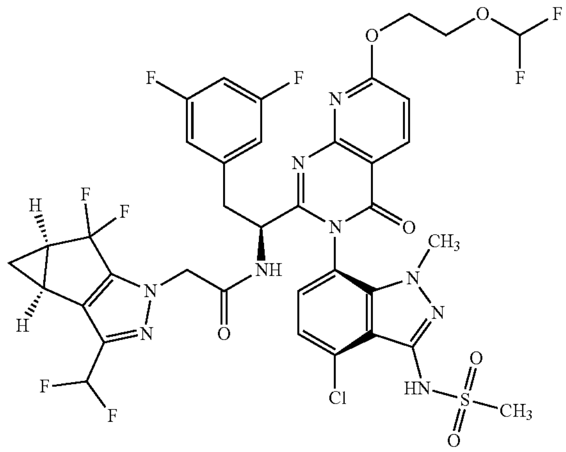

The title compound was prepared according to General Procedure A using 2-(difluoromethoxy)ethan-1-ol as the coupling partner. The experiment afforded the title compound, N-((S)-1-((3P)-3-(4-chloro-1-methyl-3-(methylsulfonamido)-1H-indazol-7-yl)-7-(2-(difluoromethoxy) ethoxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS A: retention time=1.4 min.; observed ion=916.2 (M+H). 1H NMR (500 MHz, METHANOL-d4) δ ppm 8.49-8.55 (m, 1H) 7.31 (d, J=8.05 Hz, 1H) 7.21-7.25 (m, 1H) 7.10-7.14 (m, 1H) 6.77-6.83 (m, 1H) 6.34-6.69 (m, 4H) 4.85 (s, 1H) 4.76-4.81 (m, 2H) 4.50-4.62 (m, 2H) 4.29-4.35 (m, 2H) 3.61-3.64 (m, 3H) 3.45-3.50 (m, 1H) 3.23-3.25 (m, 3H) 3.09-3.16 (m, 1H) 2.39-2.48 (m, 2H) 1.34-1.40 (m, 1H) 0.97-1.04 (m, 1H)

Preparation of Example 30: N-((S)-1-((3P)-3-(4-chloro-1-methyl-3-(methylsulfonamido)-1H-indazol-7-yl)-7-((4,6-dimethylpyrimidin-2-yl)methoxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl) acetamide

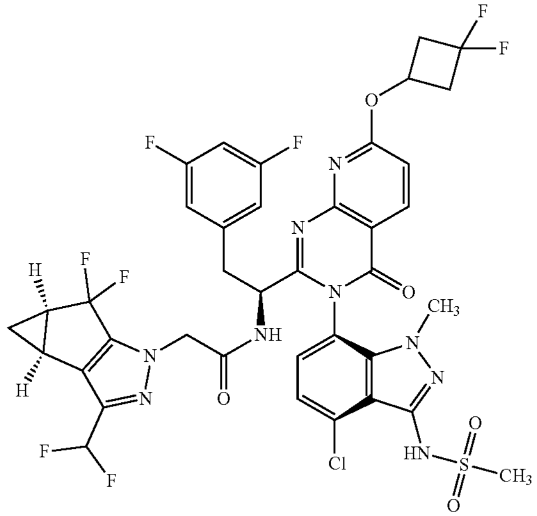

The title compound was prepared according to General Procedure B using 3,3-difluorocyclobutan-1-ol as the coupling partner. The experiment afforded the title compound, N-((S)-1-((3P)-3-(4-chloro-1-methyl-3-(methylsulfonamido)-1H-indazol-7-yl)-7-((4,6-dimethylpyrimidin-2-yl) methoxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS B: retention time=1.44 min.; observed ion=912.2 (M+H). 1H NMR (500 MHz, METHANOL-d4) δ ppm 8.50-8.59 (m, 1H) 7.29-7.33 (m, 1H) 7.19-7.26 (m, 2H) 6.51-6.82 (m, 4H) 5.69-5.77 (m, 2H) 4.82-4.86 (m, 2H) 4.49-4.61 (m, 2H) 3.57-3.64 (m, 3H) 3.39-3.46 (m, 1H) 3.21-3.25 (m, 3H) 3.02-3.13 (m, 1H) 2.33-2.54 (m, 8H) 1.34-1.41 (m, 1H) 0.97-1.04 (m, 1H)

Preparation of Example 31: N-((S)-1-((3P)-3-(4-chloro-1-methyl-3-(methylsulfonamido)-1H-indazol-7-yl)-7-((3,3-difluorocyclobutyl)methoxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

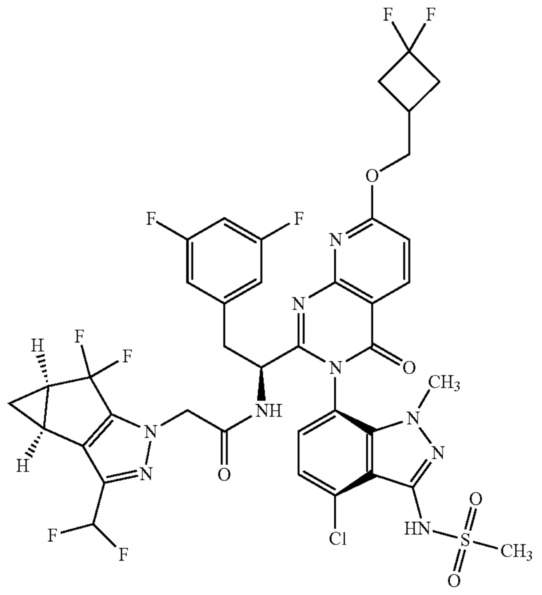

The title compound was prepared according to General Procedure A using (3,3-difluorocyclobutyl)methanol as the coupling partner. The experiment afforded the title compound, N-((S)-1-((3P)-3-(4-chloro-1-methyl-3-(methylsulfonamido)-1H-indazol-7-yl)-7-((3,3-difluorocyclobutyl)methoxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS A: retention time=1.47 min.; observed ion=926.2 (M+H). 1H NMR (500 MHz, METHANOL-d4) δ ppm 8.48-8.54 (m, 1H) 7.25-7.31 (m, 1H) 7.17-7.22 (m, 1H) 7.05-7.11 (m, 1H) 6.56-6.83 (m, 4H) 4.89-4.91 (m, 1H) 4.52-4.69 (m, 4H) 3.58-3.63 (m, 3H) 3.44-3.50 (m, 1H) 3.21-3.25 (m, 3H) 3.09-3.16 (m, 1H) 2.73-2.83 (m, 3H) 2.49-2.62 (m, 2H) 2.40-2.47 (m, 2H) 1.35-1.40 (m, 1H) 0.99-1.04 (m, 1H)

Preparation of Example 32: N-((S)-1-((3P,3P)-3-(4-chloro-1-methyl-3-(methylsulfonamido)-1H-indazol-7-yl)-7-(2-(3,3-difluorocyclobutyl)ethoxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

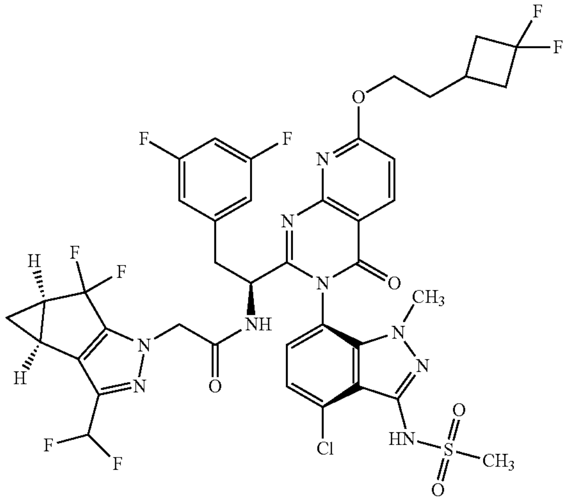

The title compound was prepared according to General Procedure A using 2-(3,3-difluorocyclobutyl)ethan-1-ol as the coupling partner. The experiment afforded the title compound, N-((S)-1-((3P,3P)-3-(4-chloro-1-methyl-3-(methylsulfonamido)-1H-indazol-7-yl)-7-(2-(3,3-difluorocyclobutyl)ethoxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS A: retention time=1.43 min.; observed ion=940.2 (M+H). 1H NMR (500 MHz, METHANOL-d4) δ ppm 8.44-8.52 (m, 1H) 7.27-7.33 (m, 1H) 7.17-7.22 (m, 1H) 7.01-7.09 (m, 1H) 6.54-6.84 (m, 4H) 4.86-4.88 (m, 1H) 4.51-4.62 (m, 4H) 3.60-3.62 (m, 3H) 3.45-3.49 (m, 1H) 3.22-3.24 (m, 3H) 3.09-3.15 (m, 1H) 2.70-2.80 (m, 2H) 2.28-2.48 (m, 5H) 2.07-2.14 (m, 2H) 1.34-1.41 (m, 1H) 0.97-1.03 (m, 1H)

Preparation of Example 33: N-((1S)-1-((3P)-3-(4-chloro-1-methyl-3-(methylsulfonamido)-1H-indazol-7-yl)-7-((2,2-difluorocyclopropyl)methoxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

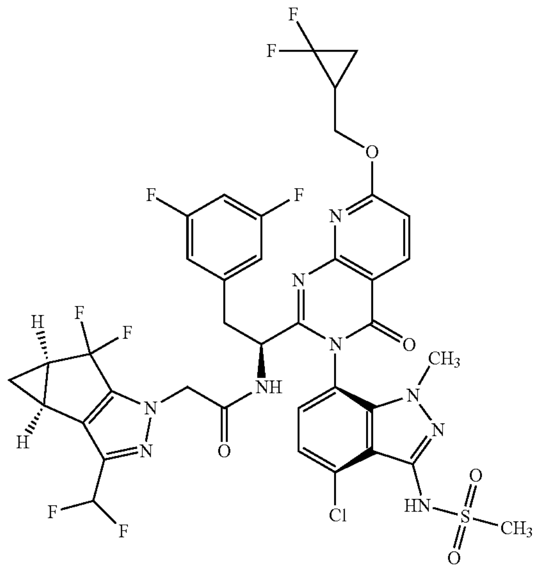

The title compound was prepared according to General Procedure A using (2,2-difluorocyclopropyl)methanol as the coupling partner. The experiment afforded the title compound, N-((1S)-1-((3P)-3-(4-chloro-1-methyl-3-(methylsulfonamido)-1H-indazol-7-yl)-7-((2,2-difluorocyclopropyl)methoxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS A: retention time=1.44 min.; observed ion=912.4 (M+H). 1H NMR (500 MHz, METHANOL-d4) δ ppm 8.47-8.56 (m, 1H) 7.30-7.36 (m, 1H) 7.22-7.29 (m, 1H) 7.07-7.14 (m, 1H) 6.56-6.84 (m, 4H) 4.70-4.81 (m, 1H) 4.51-4.64 (m, 3H) 3.61-3.65 (m, 3H) 3.44-3.51 (m, 1H) 3.26 (s, 3H) 3.10-3.17 (m, 1H) 2.48 (s, 3H) 1.64-1.76 (m, 1H) 1.44-1.53 (m, 1H) 1.30-1.40 (m, 2H) 0.98-1.04 (m, 1H)

Preparation of Example 34: N-((1S)-1-((3P,3P)-3-(4-chloro-1-methyl-3-(methylsulfonamido)-1H-indazol-7-yl)-7-(2-(2,2-difluorocyclopropoxy)ethoxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

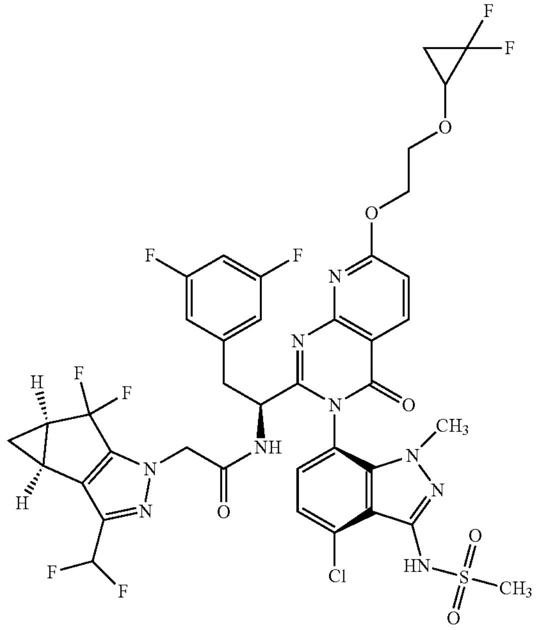

The title compound was prepared according to General Procedure A using 2-(2,2-difluorocyclopropoxy)ethan-1-ol as the coupling partner. The experiment afforded the title compound, N-((1S)-1-((3P,3P)-3-(4-chloro-1-methyl-3-(methylsulfonamido)-1H-indazol-7-yl)-7-(2-(2,2-difluorocyclopropoxy)ethoxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS A: retention time=1.41 min.; observed ion=942.2 (M+H). 1H NMR (500 MHz, METHANOL-d4) δ ppm 8.48 (d, J=8.64 Hz, 1H) 7.25-7.33 (m, 1H) 7.20 (dd, J=7.75, 1.79 Hz, 1H) 7.08 (d, J=8.64 Hz, 1H) 6.52-6.83 (m, 4H) 4.69-4.75 (m, 2H) 4.50-4.59 (m, 2H) 4.05 (t, J=4.62 Hz, 2H) 3.83-3.93 (m, 1H) 3.60 (s, 3H) 3.39-3.50 (m, 1H) 3.23 (s, 3H) 3.11 (dd, J=13.86, 9.39 Hz, 1H) 2.38-2.45 (m, 2H) 1.57-1.66 (m, 1H) 1.43-1.52 (m, 1H) 1.32-1.38 (m, 1H) 0.97-1.02 (m, 1H)

Preparation of Example 35: N-((S)-1-((3P)-3-(4-chloro-1-methyl-3-(methylsulfonamido)-1H-indazol-7-yl)-7-((4,4-difluorocyclohexyl)oxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

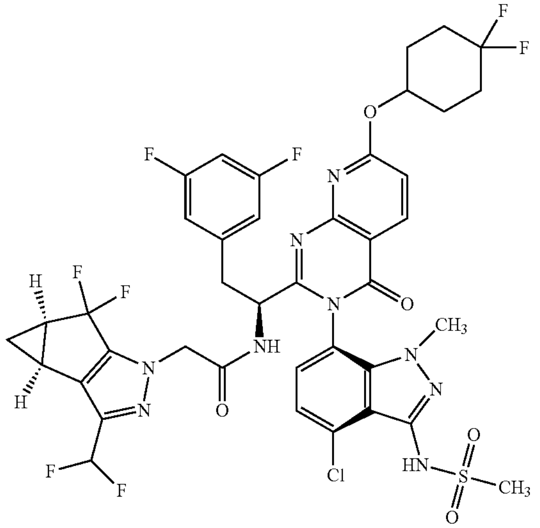

The title compound was prepared according to General Procedure A using 4,4-difluorocyclohexan-1-ol as the coupling partner. The experiment afforded the title compound, N-((S)-1-((3P)-3-(4-chloro-1-methyl-3-(methylsulfonamido)-1H-indazol-7-yl)-7-((4,4-difluorocyclohexyl)oxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS A: retention time=1.54 min.; observed ion=940.4 (M+H). 1H NMR (500 MHz, METHANOL-d4) δ ppm 8.44-8.53 (m, 1H) 7.17-7.33 (m, 2H) 7.05 (d, J=8.64 Hz, 1H) 6.53-6.83 (m, 4H) 5.49-5.58 (m, 1H) 4.82-4.84 (m, 1H) 4.49-4.62 (m, 2H) 3.59 (s, 3H) 3.42-3.51 (m, 1H) 3.21 (s, 3H) 3.10 (dd, J=14.16, 9.69 Hz, 1H) 2.37-2.46 (m, 2H) 2.02-2.22 (m, 8H) 1.32-1.38 (m, 1H) 0.96-1.01 (m, 1H)

Preparation of Example 36: N-((S)-1-((3P)-3-(4-chloro-1-methyl-3-(methylsulfonamido)-1H-indazol-7-yl)-7-(2,4-difluorophenoxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

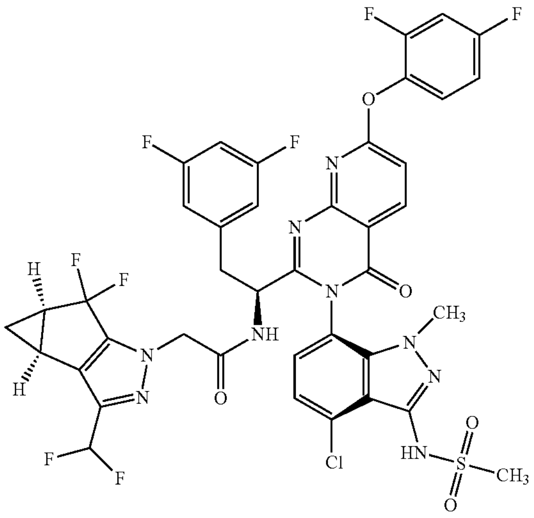

To a stirred solution of (S)-N-(7-(2-(1-amino-2-(3,5-difluorophenyl)ethyl)-7-(2,4-difluorophenoxy)-4-oxopyrido[2,3-d]pyrimidin-3(4H)-yl)-4-chloro-1-methyl-1H-indazol-3-yl)-N-(methylsulfonyl)acetamide (0.055 g, 0.076 mmol) in Tetrahydrofuran (THF) (1 mL) were added 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (0.02 g, 0.076 mmol), DIPEA (0.040 mL, 0.227 mmol) and 2,4,6-tripropyl-1,3,5,2,4,6-trioxatriphosphinane 2,4,6-trioxide (50% wt. in EtOAc, 0.090 mL, 0.151 mmol). The reaction mixture was stirred at rt for 18 h. To the reaction mixture was added ammonia in methanol (2.0 M, 1 mL) and reaction mixture was then stirred for 2 h. The mixture was concentrated under reduced pressure. The residue was dissolved in DMF (2 mL); filtered; and the filtrate was subjected to HPLC purification to afford the title compound, N-((S)-1-((3P)-3-(4-chloro-1-methyl-3-(methylsulfonamido)-1H-indazol-7-yl)-7-(2,4-difluorophenoxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS A: retention time=1.5 min.; observed ion=934.4 (M+H). 1H NMR (500 MHz, METHANOL-d4) δ ppm 8.66 (d, J=8.64 Hz, 1H) 7.41 (td, J=8.87, 5.51 Hz, 1H) 7.36 (d, J=8.64 Hz, 1H) 7.29-7.33 (m, 1H) 7.18-7.26 (m, 2H) 7.06-7.12 (m, 1H) 6.49-6.79 (m, 4H) 4.79 (dd, J=9.98, 4.62 Hz, 1H) 4.46-4.59 (m, 2H) 3.58 (s, 3H) 3.33-3.37 (m, 1H) 3.22 (s, 3H) 3.01 (dd, J=14.16, 9.98 Hz, 1H) 2.37-2.43 (m, 2H) 1.30-1.41 (m, 1H) 0.90-1.00 (m, 1H)

Preparation of Example 37: N-((S)-1-((3P)-3-(4-chloro-1-methyl-3-(methylsulfonamido)-1H-indazol-7-yl)-7-(2-fluorophenoxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

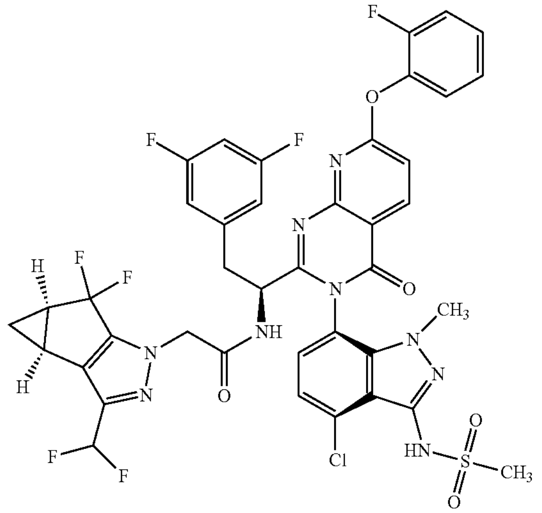

To a stirred solution of (S)-N-(7-(2-(1-amino-2-(3,5-difluorophenyl)ethyl)-7-(2-fluorophenoxy)-4-oxopyrido[2,3-d]pyrimidin-3(4H)-yl)-4-chloro-1-methyl-1H-indazol-3-yl)-N-(methylsulfonyl)acetamide (0.054 g, 0.076 mmol) in Tetrahydrofuran (THF) (1 mL) were added 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (0.02 g, 0.076 mmol), DIPEA (0.040 mL, 0.227 mmol) and 2,4,6-tripropyl-1,3,5,2,4,6-trioxatriphosphinane 2,4,6-trioxide (50% wt. in EtOAc, 0.090 mL, 0.151 mmol). The reaction mixture was stirred at rt for 18 h. To the reaction mixture was added ammonia in methanol (2.0 M, 1 mL) and the reaction mixture was then stirred for 2 h. The mixture was concentrated under reduced pressure. The residue was dissolved in DMF (2 mL); filtered; and the filtrate was subjected to HPLC purification to afford the title compound, N-((S)-1-((3P)-3-(4-chloro-1-methyl-3-(methylsulfonamido)-1H-indazol-7-yl)-7-(2-fluorophenoxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS A: retention time=1.49 min.; observed ion=916.4 (M+H). 1H NMR (500 MHz, METHANOL-d4) δ ppm 8.66 (d, J=8.64 Hz, 1H) 7.20-7.47 (m, 7H) 6.47-6.78 (m, 4H) 4.79 (dd, J=9.84, 4.47 Hz, 1H) 4.46-4.58 (m, 2H) 3.58 (s, 3H) 3.33-3.37 (m, 1H) 3.22 (s, 3H) 3.00 (dd, J=14.16, 9.69 Hz, 1H) 2.40 (ddd, J=11.18, 7.75, 4.02 Hz, 2H) 1.31-1.36 (m, 1H) 0.93-0.98 (m, 1H)

Preparation of Example 38: N-((1S)-1-((3P,3P)-3-(4-chloro-1-methyl-3-(methylsulfonamido)-1H-indazol-7-yl)-7-(2-(2,2-difluorocyclopropyl)ethoxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

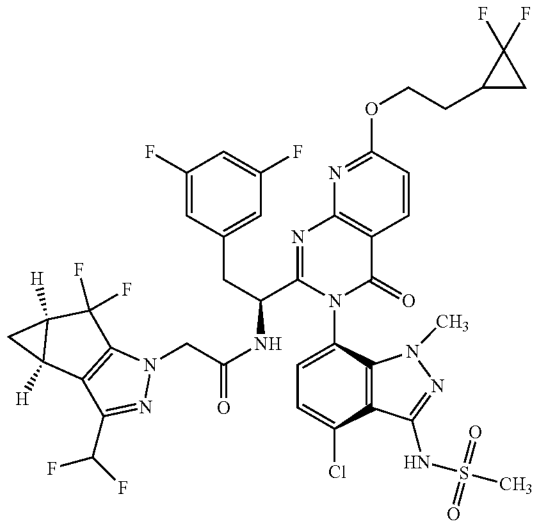

The title compound was prepared according to General Procedure A using 2-(2,2-difluorocyclopropyl)ethan-1-ol as the coupling partner. The experiment afforded the title compound, N-((1S)-1-((3P,3P)-3-(4-chloro-1-methyl-3-(methylsulfonamido)-1H-indazol-7-yl)-7-(2-(2,2-difluorocyclopropyl)ethoxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS A: retention time=1.49 min.; observed ion=926.4 (M+H). 1H NMR (500 MHz, METHANOL-d4) δ ppm 8.37-8.56 (m, 1H) 7.02-7.32 (m, 3H) 6.49-6.89 (m, 4H) 4.49-4.71 (m, 4H) 3.59 (s, 3H) 3.45 (dd, J=13.71, 4.77 Hz, 1H) 3.21 (s, 3H) 3.10 (dd, J=14.01, 9.54 Hz, 1H) 2.41 (br d, J=3.58 Hz, 2H) 1.97-2.14 (m, 2H) 1.76-1.86 (m, 1H) 1.52 (br d, J=11.92 Hz, 1H) 1.31-1.40 (m, 2H) 1.13 (dt, J=9.16, 3.32 Hz, 2H) 0.97-1.02 (m, 1H)

Preparation of Example 39: N-((S)-1-((3P,3P)-3-(4-chloro-1-methyl-3-(methylsulfonamido)-1H-indazol-7-yl)-7-(2,2,3,3,4,4,4-heptafluorobutoxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl) acetamide

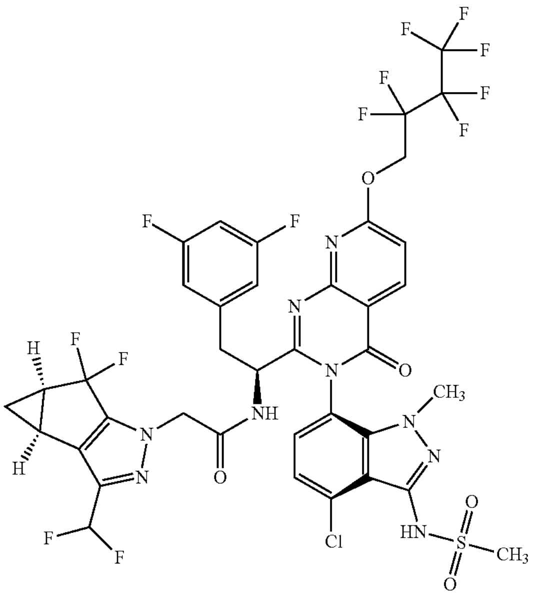

To a stirred solution of (S)-N-(7-(2-(1-amino-2-(3,5-difluorophenyl)ethyl)-7-(2,2,3,3,4,4,4-heptafluorobutoxy)-4-oxopyrido[2,3-d]pyrimidin-3(4H)-yl)-4-chloro-1-methyl-1H-indazol-3-yl)-N-(methylsulfonyl)acetamide (0.045 g, 0.057 mmol) in N,N-Dimethylformamide (1 mL) were added 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (0.015 g, 0.057 mmol), N-ethyl-N-isopropylpropan-2-amine (0.030 mL, 0.170 mmol) and 2,4,6-tripropyl-1,3,5,2,4,6-trioxatriphosphinane 2,4,6-trioxide ("T3P", 50% wt. in EtOAc, 0.068 mL, 0.114 mmol). The reaction mixture was stirred at rt for 1.5 h. To the mixture was added 2M ammonia in methanol (1 mL) and the mixture was then stirred for 1.5 h at RT. The mixture was filtered and the filtrate was subjected to HPLC purification to afford N-((S)-1-((3P,3P)-3-(4-chloro-1-methyl-3-(methylsulfonamido)-1H-indazol-7-yl)-7-(2,2,3,3,4,4,4-heptafluorobutoxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (0.0326 g, 0.029 mmol, 51.3% yield). $^{1}$H NMR (500 MHz, METHANOL-d4) δ ppm 8.59 (d, J=8.64 Hz, 1H) 7.14-7.32 (m, 3H) 6.52-6.83 (m, 4H) 5.28 (t, 3-14.01 Hz, 2H) 4.47-4.61 (m, 2H) 3.59 (s, 3H) 3.43-3.47 (m, 1H) 3.20-3.23 (m, 3H) 3.11 (dd, 3-14.16, 9.69 Hz, 1H) 2.37-2.44 (m, 2H) 1.32-1.37 (m, 1H) 0.96-1.01 (m, 1H) LC/MS retention time=1.55, 1.58 min; m/z=1004.2 $[M+H]^+$ Preparation of Example 40: N-((S)-1-((3P,3P)-3-(4-chloro-1-methyl-3-(methylsulfonamido)-1H-indazol-7-yl)-7-((2,2,3,3,4,4,5,5,5-nonafluoropentyl)oxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl) acetamide

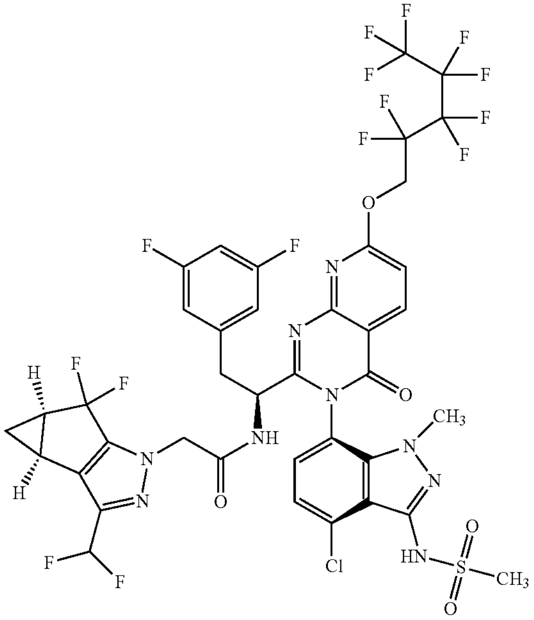

To a stirred solution of 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (0.04 g, 0.151 mmol) in tetrahydrofuran (1 mL) were added (S)-N-(7-(2-(1-amino-2-(3,5-difluorophenyl)ethyl)-7-((2,2,3,3,4,4,5,5,5-nonafluoropentyl)oxy)-4-oxopyrido[2,3-d]pyrimidin-3(4H)-yl)-4-chloro-1-methyl-1H-indazol-3-yl)-N-(methylsulfonyl)acetamide (0.129 g, 0.151 mmol), DIPEA (0.079 mL, 0.454 mmol) and 2,4,6-tripropyl-1,3,5,2,4,6-trioxatriphosphinane 2,4,6-trioxide (0.188 mL, 0.303 mmol). The reaction mixture was stirred at rt for 1.5 h, 1 mL of 2 M ammonia in methanol was added and stirring was continued for 1.5 h. The reaction mixture was concentrated, taken up in DMF (2 mL), filtered and purified by HPLC. Column: Zorbax Eclipse Plus C18, 21.2×100 mm, 5 μm particles; Solvent A=0.1% Formic Acid in 100% Water. Solvent B=Acetonitrile. Flow Rate=40 mL/min. Start % B=63.7 Final % B=83.7 Gradient Time=7 min, then a 2 min hold at 98% B. Wavelength=215 and 254 nm. ESI+Range: 150 to 1500 Dalton. Sample was loaded at 25% B and afforded N-((S)-1-((3P,3P)-3-(4-chloro-1-methyl-3-(methylsulfonamido)-1H-indazol-7-yl)-7-((2,2,3,3,4,4,5,5,5-nonafluoropentyl)oxy)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (0.0776 g, 0.069 mmol, 45.8% yield). LC/MS retention time=1.63 min; m/z=1054.2$[M+H]^+$Column: Acquity BEH C18, 2.1×30 mm, 1.7 μm particles; Solvent A=0.1% Formic acid in 100% Water. Solvent B=0.1% Formic Acid in 100% Acetonitrile. Flow Rate=0.8 mL/min. Start % B=5. Final %

B=95. Gradient Time=1.7 min, then a 0.2 min hold at 95% B. Wavelength=215 and 254 nm. ESI+Range: 150 to 1500 Dalton. System: Agilent 1290 Infinity II Preparation of Example 41: N-((S)-1-((3P, 3P)-3-(4-chloro-1-methyl-3-(methylsulfonamido)-1H-indazol-7-yl)-4-oxo-7-(2,2,3,3,3-pentafluoropropoxy)-3,4-dihydropyrido[2,3-d]pyrimidin-2-yl)-2-(3,5-difluorophenyl)ethyl)-2-((3bS,4aR)-3-cyclopropyl-5,5-difluoro-3b,4,4a,5-tetrahydro-1H-cyclopropa[3,4]cyclopenta[1,2-c]pyrazol-1-yl)acetamide

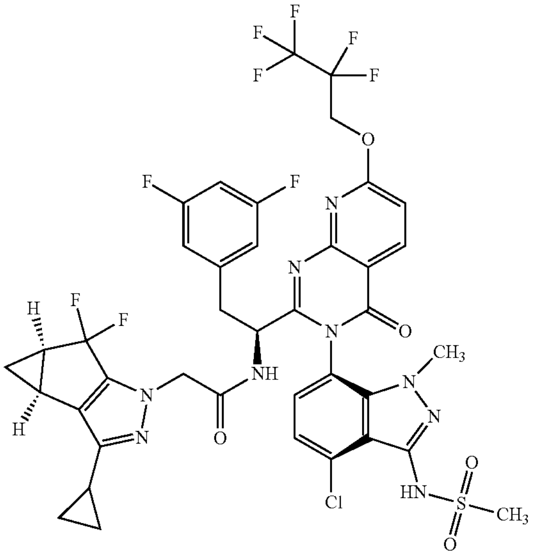

To a stirred solution of (S)-N-((6P)-7-((3P)-2-(1-amino-2-(3,5-difluorophenyl)ethyl)-4-oxo-7-(2,2,3,3,3-pentafluoropropoxy)pyrido[2,3-d]pyrimidin-3(4H)-yl)-4-chloro-1-methyl-1H-indazol-3-yl)-N-(methylsulfonyl)acetamide (0.12 g, 0.160 mmol) in Tetrahydrofuran (2.388 mL) were added 2-((3bS,4aR)-3-cyclopropyl-5,5-difluoro-3b,4,4a,5-tetrahydro-1H-cyclopropa[3,4]cyclopenta[1,2-c]pyrazol-1-yl)acetic acid (0.043 g, 0.168 mmol), N-ethyl-N-isopropylpropan-2-amine (0.084 mL, 0.480 mmol) and 2,4,6-tripropyl-1,3,5,2,4,6-trioxatriphosphinane 2,4,6-trioxide ("T3P", 50% wt. in EtOAc, 0.095 mL, 0.320 mmol). The reaction mixture was stirred at rt for 1.5 h. To the mixture was added ammonia in methanol (2M, 1 mL). The mixture was stirred for 1 h and then concentrated under reduced pressure.

The resulting residue was subjected to silica gel chromatography (40 g RediSep Gold column) eluting with 10-70% ethyl acetate in hexanes over 20 CV. Fractions containing the pure desired product were pooled and then concentrated under reduced pressure to afford N-((S)-1-((3P, 3P)-3-(4-chloro-1-methyl-3-(methylsulfonamido)-1H-indazol-7-yl)-4-oxo-7-(2,2,3,3,3-pentafluoropropoxy)-3,4-dihydropyrido[2,3-d]pyrimidin-2-yl)-2-(3,5-difluorophenyl)ethyl)-2-((3bS,4aR)-3-cyclopropyl-5,5-difluoro-3b,4,4a,5-tetrahydro-1H-cyclopropa[3,4]cyclopenta[1,2-c]pyrazol-1-yl)acetamide (0.11 g, 0.116 mmol, 72.2% yield) as a white solid. $^1$H NMR (500 MHz, METHANOL-d4) δ ppm 8.58 (d, J=8.64 Hz, 1H) 7.31 (d, J=8.05 Hz, 1H) 7.22 (d, J=7.75 Hz, 1H) 7.18 (d, J=8.64 Hz, 1H) 6.75-6.81 (m, 1H) 6.54-6.61 (m, 2H) 5.24 (t, J=13.26 Hz, 2H) 4.38-4.46 (m, 2H) 3.61 (s, 3H) 3.40-3.46 (m, 1H) 3.25 (s, 3H) 3.05-3.11 (m, 1H) 2.19-2.33 (m, 2H) 1.78-1.85 (m, 1H) 1.25-1.30 (m, 1H) 0.86-0.93 (m, 3H) 0.74-0.79 (m, 2H). LC/MS: m/z=944.0 [M+1]+.

IUPAC Chemical Names:

The IUPAC chemical names for each example are listed below. At this time these names are not recognized by common software tools such tools such as ChemDraw or JChem. Therefore, the chemical names used throughout the Examples section above were generated with ChemDraw with P/M nomenclature manually inserted. The chemical names can be converted to chemical structures using ChemDraw after the P/M nomenclature—e.g., "(3P)-"—is removed.

| Example | IUPAC Name |
|---|---|
| Example 1 | N-[(1S)-1-[(3P)-3-(4-chloro-3-methanesulfonamido-1-methyl-1H-indazol-7-yl)-7-(cyclopent-3-en-1-yloxy)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 2 | N-[(1S)-1-[(3P,3P)-3-(4-chloro-3-methanesulfonamido-1-methyl-1H-indazol-7-yl)-4-oxo-7-[(pyridin-4-yl)methoxy]-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 3 | N-[(1S)-1-[(3P)-3-(4-chloro-3-methanesulfonamido-1-methyl-1H-indazol-7-yl)-4-oxo-7-[(pyridin-3-yl)methoxy]-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 4 | N-[(1S)-1-[(3P)-3-(4-chloro-3-methanesulfonamido-1-methyl-1H-indazol-7-yl)-4-oxo-7-(4,4,4-trifluoro-3,3-dimethylbutoxy)-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 5 | N-[(1S)-1-[(3P)-3-(4-chloro-3-methanesulfonamido-1-methyl-1H-indazol-7-yl)-7-(3-methyl-3-phenylbutoxy)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 6 | N-[(1S)-1-[(3P,3P)-3-(4-chloro-3-methanesulfonamido-1-methyl-1H-indazol-7-yl)-7-[(4,6-dimethylpyrimidin-2-yl)methoxy]-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 7 | N-[(1S)-1-[(3P,3P)-3-(4-chloro-3-methanesulfonamido-1-methyl-1H-indazol-7-yl)-7-[(4-methylpyrimidin-2-yl)methoxy]-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |

-continued

| Example | IUPAC Name |
|---|---|
| Example 8 | N-[(1S)-1-[(3P,3P)-3-(4-chloro-3-methanesulfonamido-1-methyl-1H-indazol-7-yl)-7-[(5-methylpyrimidin-2-yl)methoxy]-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 9 | N-[(1S)-1-[(3P)-3-(4-chloro-3-methanesulfonamido-1-methyl-1H-indazol-7-yl)-7-{2-[methyl(2,2,2-trifluoroethyl)amino]ethoxy}-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 10 | N-[(1S)-1-[(3P)-3-(4-chloro-3-methanesulfonamido-1-methyl-1H-indazol-7-yl)-7-[2-(N-methylmethanesulfonamido)ethoxy]-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 11 | N-[(1S)-1-[(3P)-3-(4-chloro-3-methanesulfonamido-1-methyl-1H-indazol-7-yl)-7-{3-[methyl(2,2,2-trifluoroethyl)amino]propoxy}-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 12 | N-[(1S)-1-[(3P,3P)-3-(4-chloro-3-methanesulfonamido-1-methyl-1H-indazol-7-yl)-7-[2-(1-methyl-1H-pyrazol-4-yl)ethoxy]-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 13 | N-[(1S)-1-[(3P)-3-(4-chloro-3-methanesulfonamido-1-methyl-1H-indazol-7-yl)-7-{[1-methyl-5-(trifluoromethyl)-1H-pyrazol-3-yl]methoxy}-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 14 | N-[(1S)-1-[(3P,3P)-3-(4-chloro-3-methanesulfonamido-1-methyl-1H-indazol-7-yl)-7-[2-(1-methyl-1H-pyrazol-5-yl)ethoxy]-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 15 | N-[(1S)-1-[(3P)-3-(4-chloro-3-methanesulfonamido-1-methyl-1H-indazol-7-yl)-7-(3-methoxy-3-methylbutoxy)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 16 | N-[(1S)-1-[(3P,3P)-3-(4-chloro-3-methanesulfonamido-1-methyl-1H-indazol-7-yl)-7-[2-(1-methoxycyclobutyl)ethoxy]-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 17 | N-[(1S)-1-[(3P)-3-(4-chloro-3-methanesulfonamido-1-methyl-1H-indazol-7-yl)-7-[(5-methoxypentyl)oxy]-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 18 | N-[(1S)-1-[(3P,3P)-3-(4-chloro-3-methanesulfonamido-1-methyl-1H-indazol-7-yl)-4-oxo-7-(2,2,3,3,3-pentafluoropropoxy)-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 19 | N-[(1S)-1-[(3P)-3-(4-chloro-3-methanesulfonamido-1-methyl-1H-indazol-7-yl)-4-oxo-7-(3,3,4,4,4-pentafluorobutoxy)-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 20 | N-[(1S)-1-[(3P)-3-(4-chloro-3-methanesulfonamido-1-methyl-1H-indazol-7-yl)-4-oxo-7-[2-(2,2,3,3,3-pentafluoropropoxy)ethoxy]-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 21 | N-[(1S)-1-[(3P)-3-(4-chloro-3-methanesulfonamido-1-methyl-1H-indazol-7-yl)-4-oxo-7-{[1-(trifluoromethyl)cyclopropyl]methoxy}-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 22 | N-[(1S)-1-[(3P)-3-(4-chloro-3-methanesulfonamido-1-methyl-1H-indazol-7-yl)-4-oxo-7-{[6-(trifluoromethyl)pyridin-2-yl]methoxy}-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 23 | N-[(1S)-1-[(3P)-3-(4-chloro-3-methanesulfonamido-1-methyl-1H-indazol-7-yl)-4-oxo-7-{[4-(trifluoromethyl)-1,3-thiazol-2-yl]methoxy}-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 24 | N-[(1S)-1-[(3P)-3-(4-chloro-3-methanesulfonamido-1-methyl-1H-indazol-7-yl)-4-oxo-7-{[1-(2,2,2-trifluoroethyl)-1H-pyrazol-3-yl]methoxy}-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 25 | N-[(1S)-1-[(3P)-3-(4-chloro-3-methanesulfonamido-1-methyl-1H-indazol-7-yl)-4-oxo-7-{2-[(2,2,2-trifluoroethyl)amino]ethoxy}-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |

-continued

| Example | IUPAC Name |
|---|---|
| Example 26 | N-[(1S)-1-[(3P)-3-(4-chloro-3-methanesulfonamido-1-methyl-1H-indazol-7-yl)-4-oxo-7-[2-(2,2,2-trifluoroethoxy)ethoxy]-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 27 | N-[(1S)-1-[(3P,3P)-3-(4-chloro-3-methanesulfonamido-1-methyl-1H-indazol-7-yl)-4-oxo-7-(2,2,3,3-tetrafluoropropoxy)-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 28 | N-[(1S)-1-[(3P)-3-(4-chloro-3-methanesulfonamido-1-methyl-1H-indazol-7-yl)-7-{[1-(difluoromethyl)-1H-imidazol-2-yl]methoxy}-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 29 | N-[(1S)-1-[(3P)-3-(4-chloro-3-methanesulfonamido-1-methyl-1H-indazol-7-yl)-7-[2-(difluoromethoxy)ethoxy]-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 30 | N-[(1S)-1-[(3P)-3-(4-chloro-3-methanesulfonamido-1-methyl-1H-indazol-7-yl)-7-(3,3-difluorocyclobutoxy)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 31 | N-[(1S)-1-[(3P)-3-(4-chloro-3-methanesulfonamido-1-methyl-1H-indazol-7-yl)-7-[(3,3-difluorocyclobutyl)methoxy]-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 32 | N-[(1S)-1-[(3P,3P)-3-(4-chloro-3-methanesulfonamido-1-methyl-1H-indazol-7-yl)-7-[2-(3,3-difluorocyclobutyl)ethoxy]-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 33 | N-[(1S)-1-[(3P)-3-(4-chloro-3-methanesulfonamido-1-methyl-1H-indazol-7-yl)-7-[(2,2-difluorocyclopropyl)methoxy]-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 34 | N-[(1S)-1-[(3P,3P)-3-(4-chloro-3-methanesulfonamido-1-methyl-1H-indazol-7-yl)-7-[2-(2,2-difluorocyclopropoxy)ethoxy]-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 35 | N-[(1S)-1-[(3P)-3-(4-chloro-3-methanesulfonamido-1-methyl-1H-indazol-7-yl)-7-[(4,4-difluorocyclohexyl)oxy]-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 36 | N-[(1S)-1-[(3P)-3-(4-chloro-3-methanesulfonamido-1-methyl-1H-indazol-7-yl)-7-(2,4-difluorophenoxy)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 37 | N-[(1S)-1-[(3P)-3-(4-chloro-3-methanesulfonamido-1-methyl-1H-indazol-7-yl)-7-(2-fluorophenoxy)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 38 | N-[(1S)-1-[(3P,3P)-3-(4-chloro-3-methanesulfonamido-1-methyl-1H-indazol-7-yl)-7-[2-(2,2-difluorocyclopropyl)ethoxy]-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 39 | N-[(1S)-1-[(3P,3P)-3-(4-chloro-3-methanesulfonamido-1-methyl-1H-indazol-7-yl)-7-(2,2,3,3,4,4,4-heptafluorobutoxy)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 40 | N-[(1S)-1-[(3P,3P)-3-(4-chloro-3-methanesulfonamido-1-methyl-1H-indazol-7-yl)-7-[(2,2,3,3,4,4,5,5,5-nonafluoropentyl)oxy]-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 41 | N-[(1S)-1-[(3P,3P)-3-(4-chloro-3-methanesulfonamido-1-methyl-1H-indazol-7-yl)-4-oxo-7-(2,2,3,3,3-pentafluoropropoxy)-3H,4H-pyrido[2,3-d]pyrimidin-2-yl]-2-(3,5-difluorophenyl)ethyl]-2-[(2S,4R)-9-cyclopropyl-5,5-difluoro-7,8-diazatricyclo[4.3.0.0$^{2,4}$]nona-1(6),8-dien-7-yl]acetamide |

Biological Methods

HIV cell culture assay—MT-2 cells, 293T cells and the proviral DNA clone of $NL_{4-3}$ virus were obtained from the NIH AIDS Research and Reference Reagent Program. MT-2 cells were propagated in RPMI 1640 media supplemented with 10% heat inactivated fetal bovine serum (FBS), 100 μg/ml penicillin G and up to 100 units/mL streptomycin. The 293T cells were propagated in DMEM media supplemented with 10% heat inactivated FBS, 100 μg/mL penicillin G and 100 μg/mL streptomycin. A recombinant $NL_{4-3}$ proviral clone, in which a section of the nef gene was replaced with the Renilla luciferase gene, was used to make the reference virus used in these studies. The recombinant virus was prepared through transfection of the recombinant $NL_{4-3}$ proviral clone into 293T cells using Transit-293 Transfection Reagent from Mirus Bio LLC (Madison, WI). Supernatant was harvested after 2-3 days and the amount of virus present was titered in MT-2 cells using luciferase enzyme activity as a marker by measuring luciferase enzyme activity. Luciferase was quantitated using the EnduRen Live Cell Substrate from Promega (Madison, WI). Antiviral activities of compounds toward the recombinant virus were quantified by measuring luciferase activity in MT-2 cells infected for 4-5 days with the recombinant virus in the presence of serial dilutions of the compound.

The 50% effective concentration ($EC_{50}$) was calculated by using the exponential form of the median effect equation where (Fa)=1/[1+($ED_{50}$/drug conc.)m] (Johnson VA, Byington RT. Infectivity Assay. In Techniques in HIV Research. ed. Aldovini A, Walker BD. 71-76. New York: Stockton Press.1990). Curve fitting and analysis were performed with ActivityBase XE Runner software version 9.1.0.4 using model 203 (ID Business Solutions, LTD, Guildford, UK).

Compound cytotoxicity and the corresponding $CC_{50}$ values were determined using the same protocol as described in the antiviral assay except that uninfected cells were used. Cytotoxicity was assessed on day 4 in uninfected MT2 cells by using an XTT (2,3-bis[2-Methoxy-4-nitro-5-sulfophenyl]-2H-tetrazolium-5-carboxyanilide inner salt)-based colorimetric assay (Sigma-Aldrich, St Louis, Mo).

| Example | $EC_{50}$ nM | $CC_{50}$ μM |
|---|---|---|
| Example 1 | 0.024 | >0.1 |
| Example 2 | 0.060 | >0.1 |
| Example 3 | 0.048 | >0.1 |
| Example 4 | 0.078 | >0.2 |
| Example 5 | 0.43 | >0.1 |
| Example 6 | 0.036 | >0.5 |
| Example 7 | 0.059 | >0.5 |
| Example 8 | 0.049 | >0.1 |
| Example 9 | 0.018 | >0.1 |
| Example 10 | 0.041 | >0.5 |
| Example 11 | 0.027 | >0.1 |
| Example 12 | 0.14 | >0.1 |
| Example 13 | 0.058 | >0.1 |
| Example 14 | 0.061 | >0.5 |
| Example 15 | 0.019 | >0.5 |
| Example 16 | 0.030 | >0.1 |
| Example 17 | 0.046 | >0.1 |
| Example 18 | 0.031 | >0.1 |
| Example 19 | 0.044 | >0.1 |
| Example 20 | 0.045 | >0.1 |
| Example 21 | 0.046 | >0.5 |
| Example 22 | 0.055 | >0.1 |
| Example 23 | 0.100 | >0.1 |
| Example 24 | 0.057 | >0.1 |
| Example 25 | 0.057 | >0.1 |
| Example 26 | 0.024 | >0.1 |
| Example 27 | 0.022 | >0.1 |
| Example 28 | 0.87 | >0.1 |
| Example 29 | 0.033 | >0.1 |
| Example 30 | 0.031 | >0.5 |
| Example 31 | 0.035 | >0.1 |
| Example 32 | 0.000 | >0.1 |
| Example 33 | 0.037 | >0.1 |
| Example 34 | 0.035 | >0.1 |
| Example 35 | 0.054 | >0.1 |
| Example 36 | 0.081 | >0.1 |
| Example 37 | 0.081 | >0.1 |
| Example 38 | 0.037 | >0.1 |
| Example 39 | 0.122 | >0.1 |
| Example 40 | 0.31 | >0.1 |
| Example 41 | 0.043 | >0.1 |

The disclosure is not limited to the foregoing illustrative examples and the examples should be considered in all respects as illustrative and not restrictive, reference being made to the appended claims, rather than to the foregoing examples, and all changes which come within the meaning and range of equivalency of the claims are therefore intended to be embraced.

What is claimed is:

1. A compound of Formula (I), or a pharmaceutically acceptable salt thereof:

Formula (I)

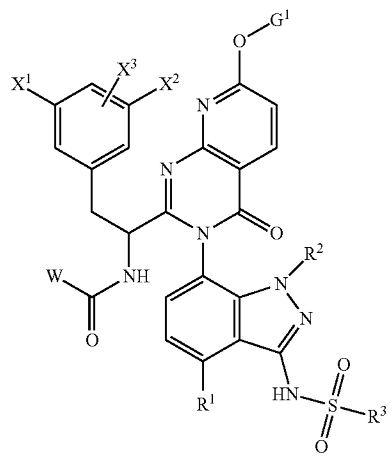

wherein:

$X^1$ and $X^2$ are independently selected from H, F, Cl, or —$CH_3$ and $X^3$ is H, F, Cl, —$CH_3$, —$OCH_3$, —$OCHF_2$, or —$OCF_3$ with the proviso that within the group $X^1$, $X^2$, and $X^3$ the substituent Cl is not used more than twice and the substituent —$CH_3$ is not used more than twice;

$R^1$ is hydrogen, Cl, F, or $CH_3$;

$R^2$ is hydrogen, $C_1$-$C_3$alkyl optionally substituted with 1-3 fluorines, or $C_3$-$C_6$cycloalkyl optionally substituted with 1-2 fluorines;

$R^3$ is $C_1$-$C_3$alkyl or $C_3$-$C_4$cycloalkyl;

$G^1$ is phenyl substituted with 1-5 fluorines, or $G^1$ is $C_1$-$C_3$ alkyl substituted once with either $G^2$, $G^3$, or $G^4$, or $G^1$ is $C_2$-$C_6$ alkyl substituted with 4-9 fluorines, $C_2$-$C_3$alkyl substituted once with $G^5$, $C_4$-Csalkyl substituted once with $G^6$, $C_3$-$C_6$cycloalkyl substituted with 1-4 fluorines, cyclohexene, or cyclopentene;

$G^2$ is 5-6 membered heteroaryl independently substituted one or two times with $C_1$-$C_2$alkyl wherein $C_1$-$C_2$alkyl is optionally substituted with 1-3 fluorines;

$G^3$ is 6-membered heteroaryl excluding 2-pyridine, 2-pyrazine, and 2-pyrimidine;

$G^4$ is $C_3$-$C_6$cycloalkyl substituted with 1-4 fluorines, $C_3$-$C_6$cycloalkyl substituted with $C_1$-$C_2$alkyl optionally substituted with 1-3 fluorines, or $C_3$-$C_6$cycloalkyl substituted with —O—$C_1$-$C_2$alkyl optionally substituted with 1-3 fluorines;

$G^5$ is —O($C_1$-$C_4$alkyl substituted with 1-5 fluorines), —O($C_3$-$C_4$cycloalkyl substituted with 1-4 fluorines), —N(H)($C_1$-$C_2$alkyl substituted with 1-5 fluorines), —N($C_1$-$C_2$alkyl substituted with 1-5 fluorines) ($C_1$-$C_3$alkyl optionally substituted with 1-3 fluorines), —N(H)($SO_2$($C_1$-$C_3$alkyl)), or —N($C_1$-$C_3$alkyl)($SO_2$($C_1$-$C_3$alkyl));

$G^6$ is phenyl or —O—$C_1$-$C_2$alkyl optionally substituted with 1-3 fluorines;

W is:

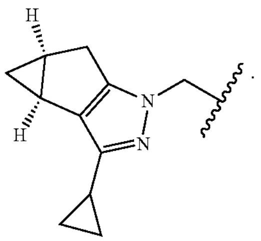 [SMILES: *Cn1nc(C2CC2)c2c1C[C@@H]1C[C@H]21]

2. The compound or pharmaceutically acceptable salt thereof according to claim 1 wherein $R^1$ is Cl; $R^2$ is methyl, 2,2-difluoroethyl, or 2,2,2-trifluoroethyl; and $R^3$ is methyl or cyclopropyl.

3. The compound or pharmaceutically acceptable salt thereof according to claim 1 wherein $X^1$ is F, $X^2$ is F, and $X^3$ is H.

4. The compound or pharmaceutically acceptable salt thereof according to claim 1 wherein if $X^3$ is H then at least one of $X^1$ and $X^2$ is other than F.

5. The compound or pharmaceutically acceptable salt thereof according to claim 1 wherein —O-$G^1$ is one of the following:

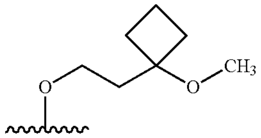
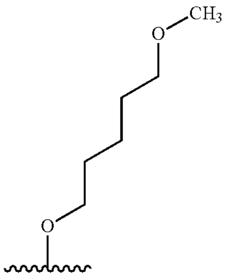
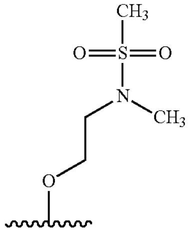
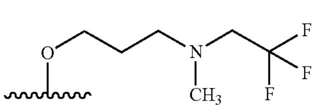
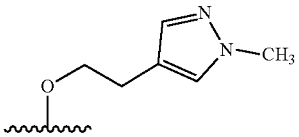
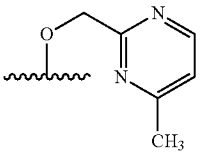
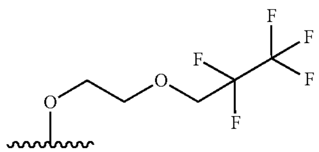
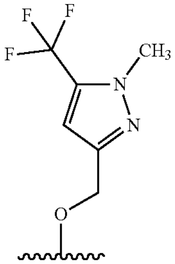

-continued

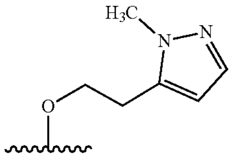
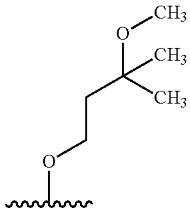
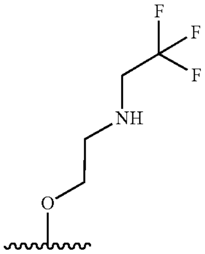
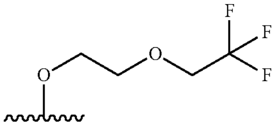
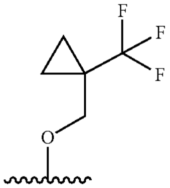
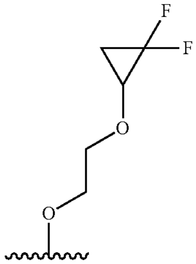
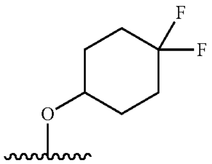
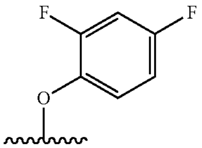
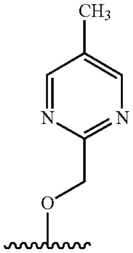
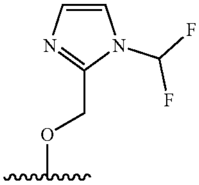
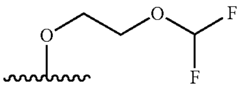
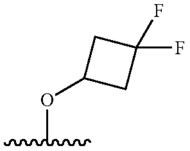
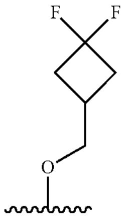
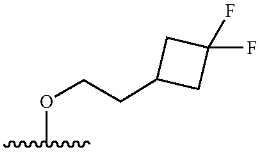
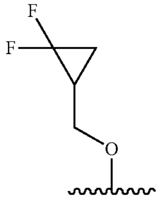
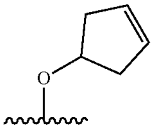
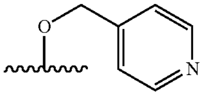

-continued

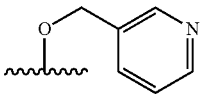
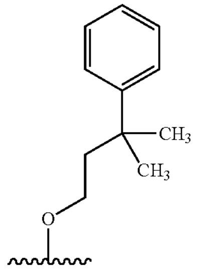
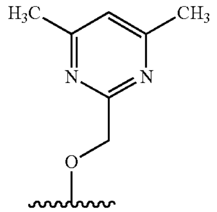
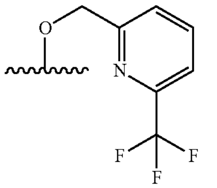
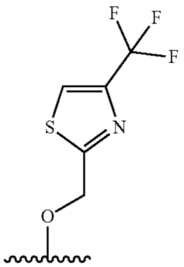
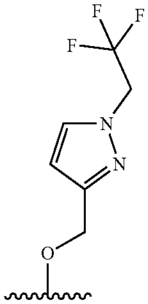
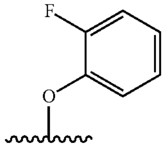
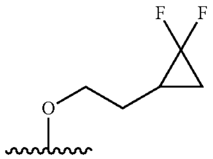
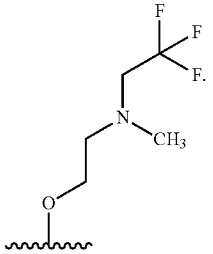

6. The compound or pharmaceutically acceptable salt thereof according to claim 1 wherein —O-$G^1$ is one of the following:

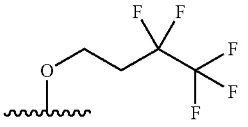
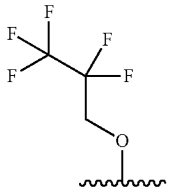
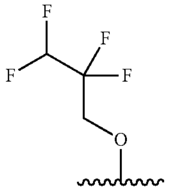
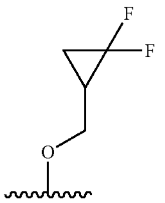
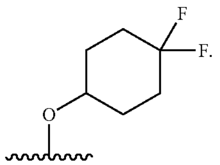

7. The compound or pharmaceutically acceptable salt thereof according to claim 1 wherein the stereochemistry is as depicted below:

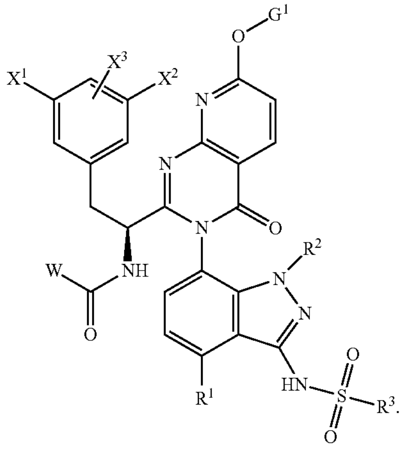

8. The compound or pharmaceutically acceptable salt thereof according to claim 1 wherein the stereochemistry is as depicted below:

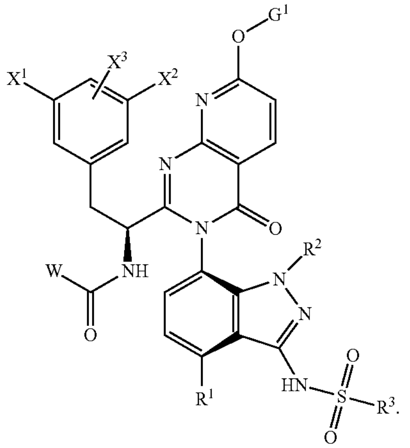

9. A pharmaceutical composition comprising the compound or pharmaceutically acceptable salt thereof according to claim 1, further comprising a pharmaceutically acceptable excipient.

10. The composition according to claim 9 suitable for oral administration, for intramuscular injection, or for subcutaneous injection.

11. A method of treating HIV infection in a human comprising administration of a therapeutically effective amount of the compound or pharmaceutically acceptable salt thereof according to claim 1.

12. The method of claim 11 wherein said administration is oral.

13. The method of claim 11 wherein said administration is intramuscular injection or subcutaneous injection.

14. The method of claim 11 wherein said method further comprises administration of at least one other agent used for treatment of HIV infection in a human, wherein said at least one other agent is selected from the group consisting of abacavir, atazanavir, bictegravir, cabotegravir, darunavir, delavirdine, didanosine, dideoxyinosine, dolutegravir, doravirine, efavirenz, elvitegravir, emtricitabine, etavirine, fosamprenavir, fostemsavir, indinavir, slatravir, lamivudine, lopinavir, maraviroc, nelfinavir, nevirapine, raltegravir, rilpiverine, ritonavir, saquinavir, stavudine, tipranavir, tenofovir, tenofovir alafenamide, tenofovir disoproxil fumarate, zalcitabine, zidovudine, GSK4000422, GSK4023991, GSK3640254, GSK3739937, and N6LS.

15. The method of claim 14 wherein said at least one other agent is selected from the group consisting of dolutegravir, bictegravir, lamivudine, fostemsavir, and cabotegravir.

16. The method of claim 14 wherein said at least one other agent is selected from the group consisting of GSK4000422, GSK4023991, GSK3640254, GSK3739937, and N6LS.

17. A compound of Formula (I), or a pharmaceutically acceptable salt thereof:

Formula (I)

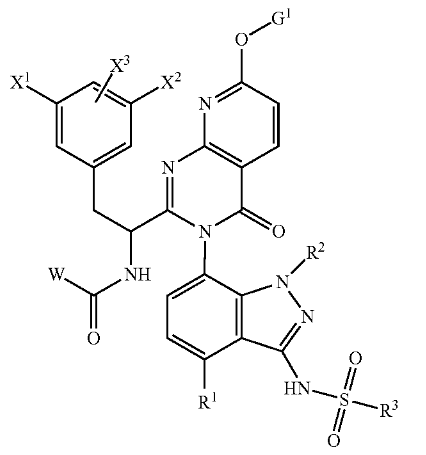

wherein:

$X^1$ and $X^2$ are independently selected from H, F, $C_1$, or $-CH_3$ and $X^3$ is H, F, Cl, $-CH_3$, $-OCH_3$, $-OCHF_2$, or $-OCF_3$ with the proviso that within the group $X^1$, $X^2$, and $X^3$ the substituent $C_1$ is not used more than twice and the substituent-$CH_3$ is not used more than twice and with the proviso that if $X^3$ is H, then at least one of $X^1$ and $X^2$ is other than F;

$R^1$ is hydrogen, $C_1$, F, or $CH_3$;

$R^2$ is hydrogen, $C_1$-$C_3$alkyl optionally substituted with 1-3 fluorines, or $C_3$-Cocycloalkyl optionally substituted with 1-2 fluorines;

$R^3$ is $C_1$-$C_3$alkyl or $C_3$-$C_4$cycloalkyl;

$G^1$ is phenyl substituted with 1-5 fluorines, or $G^1$ is $C_1$-$C_3$ alkyl substituted once with either $G^2$, $G^3$, or $G^4$, or $G^1$ is $C_2$-$C_6$ alkyl substituted with 4-9 fluorines, $C_2$-$C_3$alkyl substituted once with $G^5$, $C_4$-Csalkyl substituted once with $G^6$, $C_3$-$C_6$cycloalkyl substituted with 1-4 fluorines, cyclohexene, or cyclopentene;

$G^2$ is 5-6 membered heteroaryl independently substituted one or two times with $C_1$-$C_2$alkyl wherein $C_1$-$C_2$alkyl is optionally substituted with 1-3 fluorines;

$G^3$ is 6-membered heteroaryl excluding 2-pyridine, 2-pyrazine, and 2-pyrimidine;

$G^4$ is $C_3$-Cócycloalkyl substituted with 1-4 fluorines, $C_3$-$C_6$cycloalkyl substituted with $C_1$-$C_2$alkyl optionally substituted with 1-3 fluorines, or $C_3$-$C_6$cycloalkyl substituted with $-O-C_1$-$C_2$alkyl optionally substituted with 1-3 fluorines;

$G^5$ is $-O(C_1$-$C_4$alkyl substituted with 1-5 fluorines), $-O(C_3$-$C_4$cycloalkyl substituted with 1-4 fluorines), $-N(H)$ ($C_1$-$C_2$alkyl substituted with 1-5 fluorines), $-N(C_1$-$C_2$alkyl substituted with 1-5 fluorines) ($C_1$-$C_3$alkyl optionally substituted with 1-3 fluorines), $-N(H)$ ($SO_2$ ($C_1$-$C_3$alkyl)), or $-N(C_1$-$C_3$alkyl) ($SO_2$ ($C_1$-$C_3$alkyl));

$G^6$ is phenyl or $-O-C_1$-$C_2$alkyl optionally substituted with 1-3 fluorines;

W is selected from:

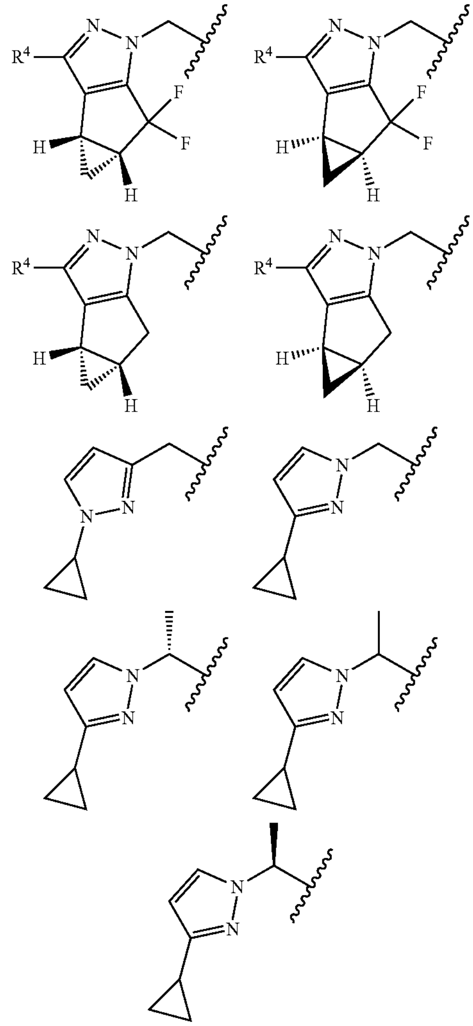

wherein $R^4$ is methyl optionally substituted with 1-3 fluorines or $R^4$ is cyclopropyl.

18. A compound selected from the group consisting of:

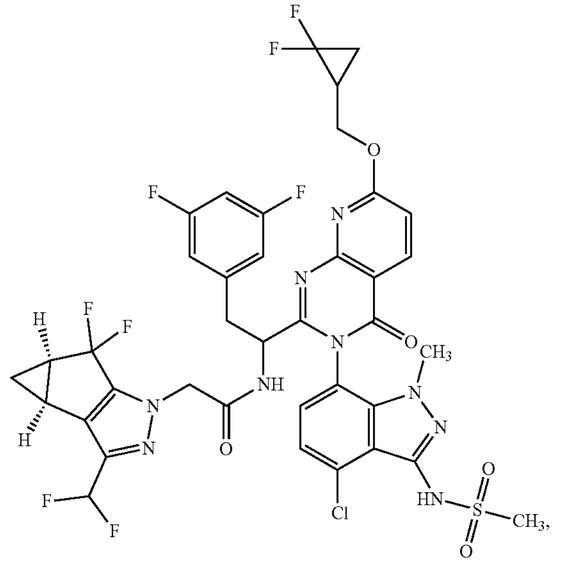

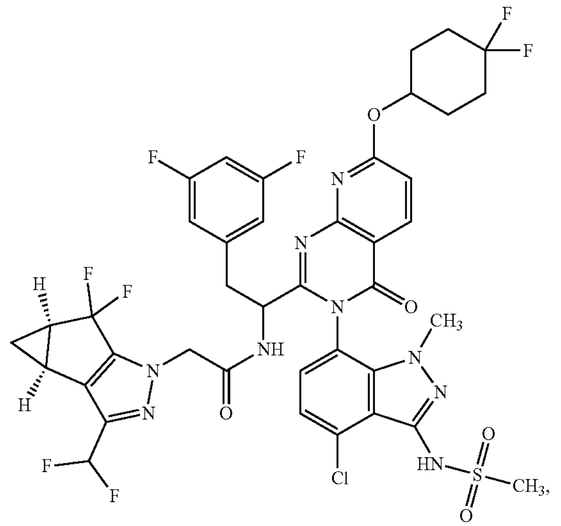

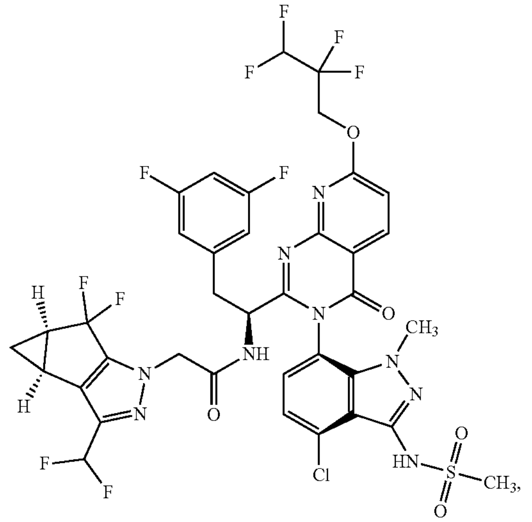

and

-continued

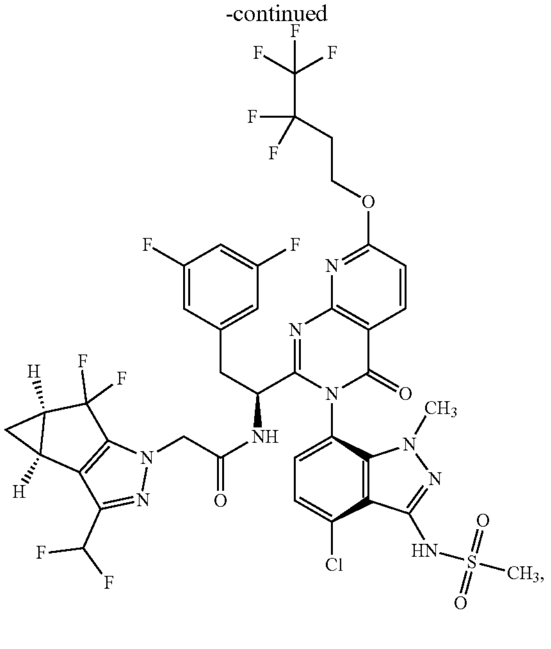

or a pharmaceutically acceptable salt thereof.

19. The compound or pharmaceutically acceptable salt according to claim 18, wherein the compound or pharmaceutically acceptable salt is:

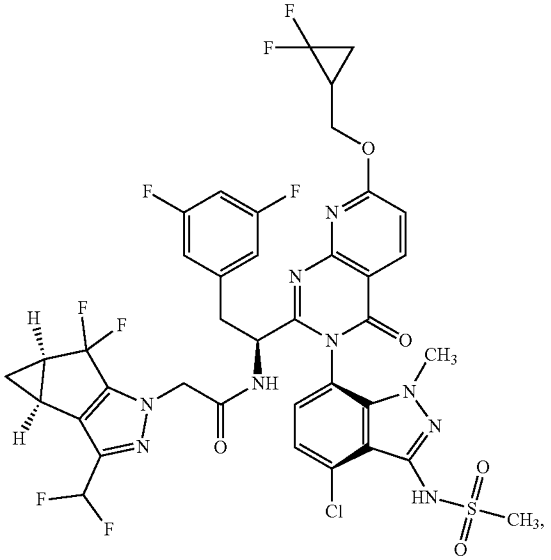

or a pharmaceutically acceptable salt thereof.

20. The compound or pharmaceutically acceptable salt according to claim 18, wherein the compound or pharmaceutically acceptable salt is:

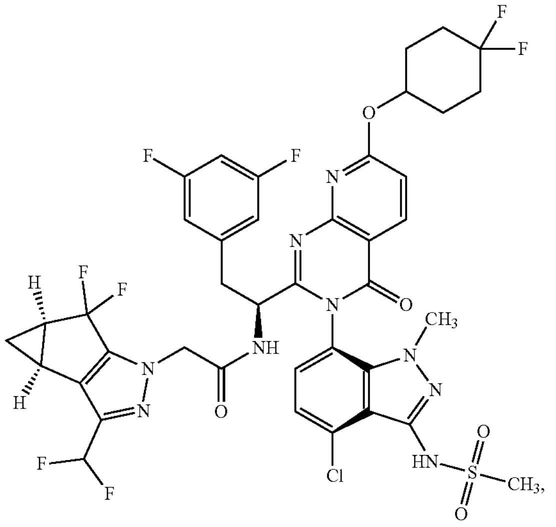

or a pharmaceutically acceptable salt thereof.

21. The compound or pharmaceutically acceptable salt according to claim 18, wherein the compound or pharmaceutically acceptable salt is:

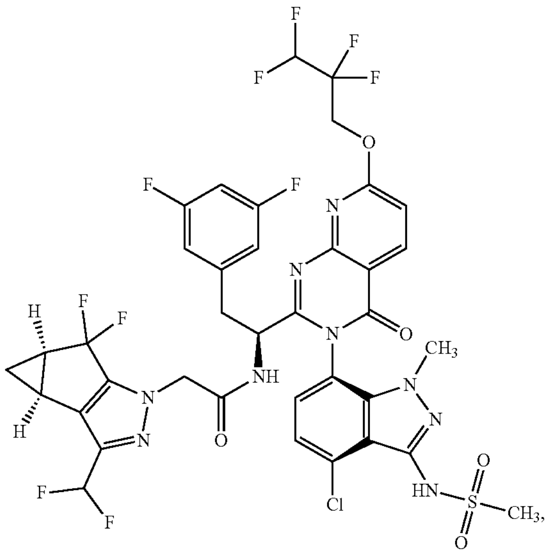

or a pharmaceutically acceptable salt thereof.

22. The compound or pharmaceutically acceptable salt according to claim 18, wherein the compound or pharmaceutically acceptable salt is:

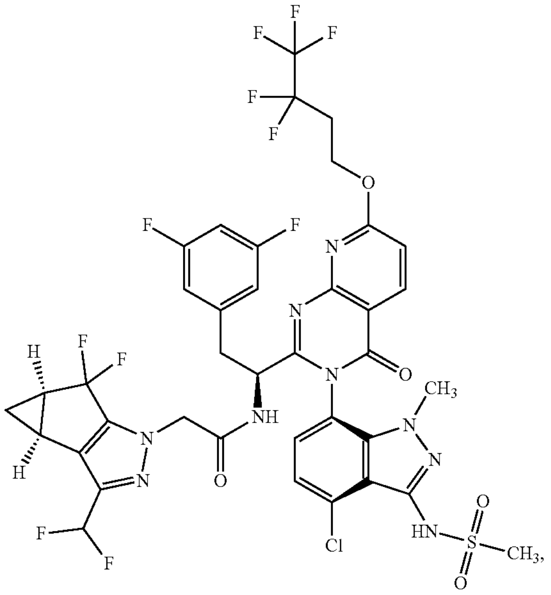

or a pharmaceutically acceptable salt thereof.

23. The compound, or a pharmaceutically acceptable salt thereof according to claim 18 wherein the compound is:

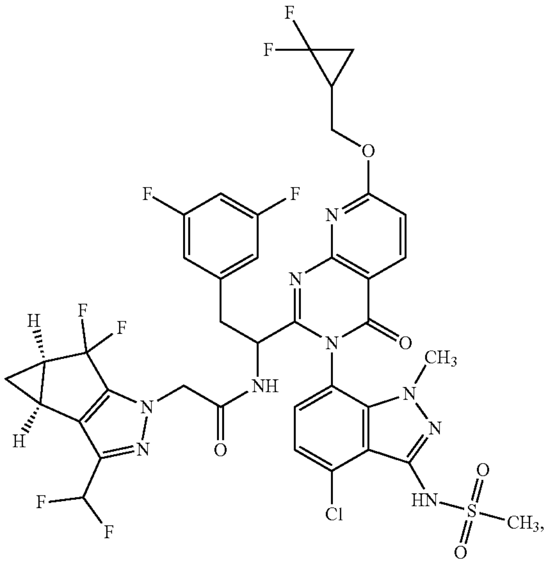 [SMILES: Cn1nc(NS(C)(=O)=O)c2c(Cl)ccc(-n3c(C(Cc4cc(F)cc(F)c4)NC(=O)Cn4nc(C(F)F)c5c4C(F)(F)[C@@H]4C[C@H]54)nc4nc(OCC5CC5(F)F)ccc4c3=O)c21]

or a pharmaceutically acceptable salt thereof.

24. The compound, or a pharmaceutically acceptable salt thereof according to claim 18 wherein the compound is:

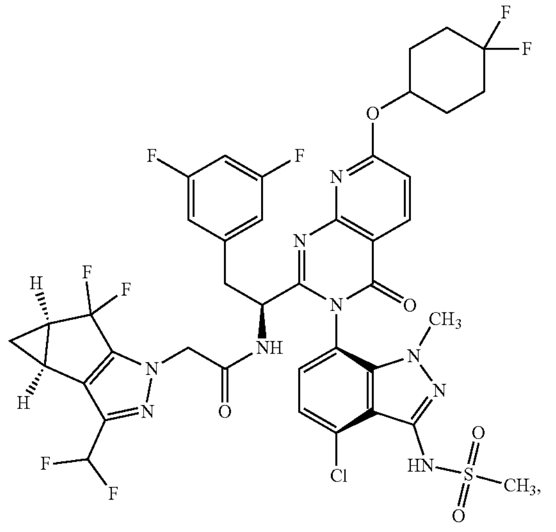

or a pharmaceutically acceptable salt thereof.

25. A pharmaceutical composition comprising the compound or pharmaceutically acceptable salt thereof according to claim 18, further comprising a pharmaceutically acceptable excipient.

26. The composition according to claim 25 suitable for oral administration, for intramuscular injection, or for subcutaneous injection.

27. A method of treating HIV infection in a human comprising administration of a therapeutically effective amount of the compound or pharmaceutically acceptable salt thereof according to claim 18.

28. The method of claim 27 wherein said administration is oral.

29. The method of claim 27 wherein said administration is intramuscular injection or subcutaneous injection.

30. The method of claim 27 wherein said method further comprises administration of at least one other agent used for treatment of HIV infection in a human, wherein said at least one other agent is selected from the group consisting of abacavir, atazanavir, bictegravir, cabotegravir, darunavir, delavirdine, didanosine, dideoxyinosine, dolutegravir, doravirine, efavirenz, elvitegravir, emtricitabine, etavirine, fosamprenavir, fostemsavir, indinavir, slatravir, lamivudine, lopinavir, maraviroc, nelfinavir, nevirapine, raltegravir, rilpiverine, ritonavir, saquinavir, stavudine, tipranavir, tenofovir, tenofovir alafenamide, tenofovir disoproxil fumarate, zalcitabine, zidovudine, GSK4000422, GSK4023991, GSK3640254, GSK3739937, and N6LS.

31. The method of claim 30 wherein said at least one other agent is selected from the group consisting of dolutegravir, bictegravir, lamivudine, fostemsavir, and cabotegravir.

32. The method of claim 30 wherein said at least one other agent is selected from the group consisting of GSK4000422, GSK4023991, GSK3640254, GSK3739937, and N6LS.

* * * * *